US009624289B2

(12) United States Patent
Tusche et al.

(10) Patent No.: US 9,624,289 B2
(45) Date of Patent: Apr. 18, 2017

(54) METHODS AND COMPOSITIONS FOR MODULATING TOSO ACTIVITY

(71) Applicant: University Health Network, Toronto (CA)

(72) Inventors: Michael W. Tusche, Toronto (CA); Tak W. Mak, Toronto (CA); Pamela S. Ohashi, Toronto (CA); Philipp Lang, Duesseldorf (DE); Karl Lang, Essen (DE); Dirk Brenner, Toronto (CA); Gloria Lin, Toronto (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 14/539,884

(22) Filed: Nov. 12, 2014

(65) Prior Publication Data

US 2015/0197551 A1 Jul. 16, 2015

Related U.S. Application Data

(60) Division of application No. 14/539,872, filed on Nov. 12, 2014, which is a continuation of application No. 13/831,031, filed on Mar. 14, 2013, now Pat. No. 9,228,006.

(60) Provisional application No. 61/612,183, filed on Mar. 16, 2012, provisional application No. 61/646,143, filed on May 11, 2012, provisional application No. 61/731,428, filed on Nov. 29, 2012.

(51) Int. Cl.
*C07K 14/705* (2006.01)
*A61K 38/17* (2006.01)

(52) U.S. Cl.
CPC .... *C07K 14/70503* (2013.01); *A61K 38/1709* (2013.01); *A61K 38/1774* (2013.01); *C07K 14/705* (2013.01); *C07K 2319/02* (2013.01); *C07K 2319/30* (2013.01)

(58) Field of Classification Search
CPC ............ A61K 38/1709; A61K 38/1774; C07K 14/705; C07K 14/70503; C07K 2319/02; C07K 2319/30
See application file for complete search history.

(56) References Cited

U.S. PATENT DOCUMENTS

| | | | |
|---|---|---|---|
| 6,683,168 B1 | 1/2004 | Rothstein et al. | |
| 6,727,350 B2 | 4/2004 | Nolan et al. | |
| 6,855,495 B1 | 2/2005 | Payan | |
| 7,645,449 B2 | 1/2010 | Stassi et al. | |
| 2008/0295190 A1 | 11/2008 | Wong et al. | |
| 2010/0099742 A1 | 4/2010 | Stassi et al. | |
| 2012/0148581 A1 | 6/2012 | Xiong et al. | |
| 2013/0281356 A1 | 10/2013 | Tusche et al. | |

FOREIGN PATENT DOCUMENTS

| | | |
|---|---|---|
| WO | WO 91/04055 A1 | 4/1991 |
| WO | WO 93/10138 A1 | 5/1993 |
| WO | WO 00/61132 A1 | 10/2000 |
| WO | WO 01/62905 A2 | 8/2001 |
| WO | WO 2008/154351 A1 | 12/2008 |
| WO | WO 2009/134633 A1 | 11/2009 |
| WO | WO 2013/136193 A2 | 9/2013 |

OTHER PUBLICATIONS

Aggarwal, A. et al., "Gene Expression Profiling Reveals Dysregulation of Innate Immune Genes in Synovial Fluid Mononuclear Cells of Patients With Enthesitis Related Arthritis," *Arthritis & Rheumatism*, Nov. 2011, vol. 63, Abstract Supplement, 1 page.
Dharmadhikari, G. et al., "The Fas apoptotic inhibitory protein TOSO induces proliferation in human beta cells," *Diabetologia*, 2009, vol. 52 (Suppl 1) S1-S550, Abstract No. 199, p. S88.
Evan, G.I. et al., "Isolation of Monoclonal Antibodies Specific for Human c-*myc* Proto-Oncogene Product," *Molecular and Cellular Biology*, Dec. 1985, vol. 5, No. 12, pp. 3610-3616.
Field, J. et al., "Purification of a *RAS*-Responsive Adenylyl Cyclase Complex from *Saccharomyces cerevisiae* by Use of n Epitope Addition Method," *Molecular and Cellular Biology*, May 1988, vol. 8, No. 5, pp. 2159-2165.
GenBank Accession No. NM000632, "*Homo sapiens* integrin, alpha M (complement component 3 receptor 3 subunit) (ITGAM), transcript variant 2 mRNA," Sep. 14, 2013, 7 pages.
GenBank Accession No. NM001014843, "Rattus norvegicus Fas apoptotic inhibitory molecule 3 (Faim3), mRNA," Sep. 1, 2013, 2 pages.
GenBank Accession No. NM001142473, "*Homo sapiens* Fas apoptotic inhibitory molecule 3 (FAIM3), transcript variant 3, mRNA," Aug. 19, 2013, 4 pages.
GenBank Accession No. NM001193338, "*Homo sapiens* Fas apoptotic inhibitory molecule 3 (FAIM3), transcript variant 4, mRNA," Aug. 25, 2013, 4 pages.
GenBank Accession No. NM005449, "*Homo sapiens* Fas apoptotic inhibitory molecule 3 (FAIM3), transcript variant 1, mRNA," Aug. 19, 2013, 5 pages.
GenBank Accession No. NM026976, "Mus musculus Fas apoptotic inhibitory molecule 3 (Faim3), mRNA," Aug. 22, 2013, 3 pages.
GenBank Accession No. NP000623, integrin alpha-M isoform 2 precursor [*Homo sapiens*], Sep. 14, 2013, 4 pages.
GenBank Accession No. NP00104843, fas apoptotic inhibitory molecule 3 precursor [Rattus norvegicus], Sep. 1, 2013, 2 pages.
GenBank Accession No. NP001135945, "fas apoptotic inhibitory molecule 3 isoform b [*Homo sapiens*]," Aug. 19, 2013, 3 pages.
GenBank Accession No. NP001180267, "fas apoptotic inhibitory molecule 3 isoform c precursor [*Homo sapiens*]," Aug. 25, 2013, 3 pages.

(Continued)

*Primary Examiner* — Hasan Ahmed
*Assistant Examiner* — Erinne Dabkowski

(57) ABSTRACT

The present invention is further directed to methods and compositions for modulating the activity of the Toso protein. The invention further encompasses treatment of disorders associated with inflammation, autoimmune disorders, and cancer using compositions that include a soluble Toso protein.

5 Claims, 42 Drawing Sheets

(56) References Cited

OTHER PUBLICATIONS

GenBank Accession No. NP005440, "fas apoptotic inhibitory molecule 3 isoform a precursor [Homo sapiens]," Aug. 19, 2013, 3 pages.

GenBank Accession No. NP081252, "fas apoptotic inhibitory molecule 3 precursor [Mus musculus]," Aug. 22, 2013, 2 pages.

Hirano, N. et al., "Engagement of CD83 ligand induces prolonged expansion of CD8+T cells and preferential enrichment for antigen specificity," Blood, Feb. 15, 2006, vol. 107, No. 4, pp. 1528-1536.

Hopp, T.P, et al., "A Short Polypeptide Marker Sequence Useful for Recombinant Protein Identification and Purification," Bio/Technology, Oct. 1988, vol. 6, pp. 1204-1210.

International Search Report mailed Oct. 22, 2013, for International Patent Application No. PCT/IB2013/001179, 5 pages.

Lang, P.A. et al., "Aggravation of viral hepatitis by platelet-derived serotonin," Nature Medicine, Jul. 2008, vol. 14, No. 7, pp. 756-761.

Lutz-Freyermuth, C. et al., "Quantitative determination that one of two potential RNA-binding domains of the A protein component of the U1 small nuclear ribonucleoprotein complex binds with high affinity to stem-loop II of U1 RNA," Proc. Natl. Acad. Sci. USA, Aug. 1990, vol. 87, pp. 6393-6397.

Martin, G.A. et al., "GAP Domains Responsible for Ras p21-Dependent Inhibition of Muscarinic Atrial K+Channel Currents," Science, Jan. 10, 1992, vol. 255, pp. 192-194.

Nguyen, X-H. et al., "Toso regulates the balance between apoptotic and nonapoptotic receptor signaling by facilitating RIP1 ubiquitination," Blood, Jul. 21, 2011, vol. 118, No. 3, pp. 598-608.

Oettgen, H.C. et al., "IgE regulation and roles in asthma pathogenesis," J Allergy Clin Immunol, 2001, vol. 107, pp. 429-440.

Paborsky, L.R. et al., "Mammalian cell transient expression of tissue factor for the production of antigen," Protein Engineering, 1990, vol. 3, No. 6, pp. 547-553.

Shima, H. et al., "Identification of TOSO/FAIM3 as an Fc receptor for IGM," International Immunology, 2009, vol. 22, No. 3, pp. 149-156.

Skinner, R.H. et al., "Use of the Glu-Glu-Phe C-terminal Epitope for Rapid Purification of the Catalytic Domain of Normal and Mutant ras GTPase-activating Proteins," The Journal of Biological Chemistry, Aug. 5, 1991, vol. 266, No. 22, pp. 14163-14166.

Zhang, L. et al., "Alteration in the IL-2 signal peptide affects secretion of proteins in vitro and in vivo," The Journal of Gene Medicine, 2005, vol. 7, pp. 354-365.

Dharmadhikari, G. et al., "TOSO promotes β-cell proliferation and protects from apoptosis," Molecular Metabolism, 2012, vol. 1, pp. 70-78.

Hitoshi, Y. et al., "Toso, a Cell Surface, Specific Regulator of Fas-Induced Apoptosis in T Cells," Immunity, Apr. 1998, vol. 8, pp. 461-471.

Honjo, K. et al., "Is Toso an antiapoptotic protein or an Fc receptor for IgM?" Blood, Feb. 16, 2012, vol. 119, No. 7, pp. 1789-1790.

Honjo, K. et al., "Is Toso/IgM Fc receptor (FcµR) expressed by innate immune cells," PNAS, Jul. 9, 2013, vol. 110, No. 28, pp. E2540-E2541.

Kubagawa, H. et al., "The Old but New IgM Fc Receptor (FcµR)," in Fc Receptors, Current Topics in Microbiology and Immunology 382, 2014, Daëron, M. et al. (eds.), Springer International Publishing Switzerland, pp. 3-28.

Lang, K.S. et al., "Reply to Honjo et al.: Functional relevant expression of Toso on granulocytes," PNAS, Jul. 9, 2013, vol. 110, No. 28, pp. E2542-E2543.

MedlinePlus, "Autoimmune disorders: MedlinePlus Medical Encyclopedia," located at <http:www.nlm.nig.gov/medlineplus/ency/article/000816.htm>, 4 pages.

Nguyen, X-H. et al., "Antiapoptotic function of Toso (Faim3) in death receptor signaling," Blood, Feb. 16, 2012, vol. 119, No. 7, pp. 1790-1791.

Sriram, S. et al., "Experimental Allergic Encephalomyelitis: A Misleading Model of Multiple Sclerosis," Ann Neurol, 2005, vol. 58, pp. 939-945.

Steinman, L., et al., "How to Successfully Apply Animal Studies in Experimental Allergic Encephalomyelitis to Research on Multiple Sclerosis," Ann Neurol, 2006, vol. 60, pp. 12-21.

Stern, B. et al., "Improving mammalian cell factories: The selection of signal peptide has a major impact on recombinant protein synthesis and secretion in mammalian cells," Trends in Cell & Molecular Biology, 2007, vol. 2, pp. 1-17.

Topalian, S.L. et al., "Safety, Activity, and Immune Correlates of Anti-PD-1 Antibody in Cancer," The New England Journal of Medicine, Jun. 28, 2012, vol. 366, No. 26, pp. 2443-2454.

Bellone, M. et al., "Ways to enhance lymphocyte trafficking into tumors and fitness of tumor infiltrating lymphocytes," Frontiers in Oncology, Sep. 11, 2013, vol. 3, Article 231, pp. 1-15.

Brenner, D. et al., "Toso controls encephalitogenic immune responses by dendritic cells and regulatory T cells," PNAS, Jan. 11, 2014, vol. 111, No. 3, pp. 1060-1065.

Burkholder, B. et al., "Tumor-induced perturbations of cytokines and immune cell networks," Biochimica et Biophysica Acta, 2014, vol. 1845, pp. 182-201.

Callahan, M.K. et al., "At the Bedside: CTLA-4- and PD-1-blocking antibodies in cancer immunotherapy," Journal of Leukocyte Biology, Jul. 2013, vol. 94, pp. 41-53.

Fan, C-W., et al, "Blockade of phospholipid scramblase 1 with its N-terminal domain antibody reduces tumorigenesis of colorectal carcinomas in vitro and in vivo," Journal of Translational Medicine, 2012, vol. 10, No. 254, pp. 1-13.

International Search Report for International Patent Application No. PCT/IB2015/001033, mailed on Oct. 9, 2015, 4 pages.

Vire, B. et al., "TOSO, the Fcµ Receptor, Is Highly Expressed on Chronic Lymphocytic Leukemia B Cells, Internalizes upon IgM Binding, Shuttles to the Lysosome, and Is Downregulated in Response to TLR Activation," The Journal of Immunology, 2011, vol. 187, pp. 4040-4050.

Walsh, D. et al., "Pattern recognition receptors—Molecular orchestrators of inflammation in inflammatory bowel disease," Cytokine & Growth Factor Reviews, 2013, vol. 24, pp. 91-104.

U.S. Appl. No. 14/539,872, filed Nov. 12, 2014.
U.S. Appl. No. 14/539,879, filed Nov. 12, 2014.
U.S. Appl. No. 14/322,551, filed Jul. 2, 2014.
U.S. Appl. No. 14/640,318, filed Mar. 6, 2015.

Achiron, A. et al., "Impaired Expression of Peripheral Blood Apoptotic-Related Gene Transcripts in Acute Multiple Sclerosis Relapse," Ann. N.Y. Acad. Sci., 2007, vol. 1107, pp. 155-167.

Casset, F. et al., "A peptide mimetic of an anti-CD4 monoclonal antibody by rational design," Biochemical and Biophysical Research Communications, 2003, vol. 307, pp. 198-205.

Colman, P.M., "Effects of amino acid sequence changes on antibody-antigen interactions," Research in Immunology, 1994, vol. 145, pp. 33-36.

De Pascalis, R. et al., "Grafting of 'Abbreviated' Complementary-Determining Regions Containing Specificity-Determining Residues Essential for Ligand Contact to Engineer a Less Immunogenic Humanized Monolconal Antibody," The Journal of Immunology, 2002, vol. 169, pp. 3076-3084.

MacCallum, R.M. et al., "Antibody-antigen Interactions: Contact Analysis and Binding Site Topography," J. Mol. Biol., 1996, vol. 262, pp. 732-745.

Paul, W.E. ed., "Fundamental Immunology Third Edition," Raven Press, NY, 1993, pp. 292-295.

Rudikoff, S., et al., "Single amino acid substitution altering antigen-binding specificity," Proc. Natl. Acad. Sci. USA, Mar. 1982, vol. 79, pp. 1979-1983.

Kubagawa, H. et al., "Identity of the elusive IgM Fc Receptor (FcµR) in humans," J. Exp. Med., 2009, vol. 206, No. 12, pp. 149-156.

FIG. 8A

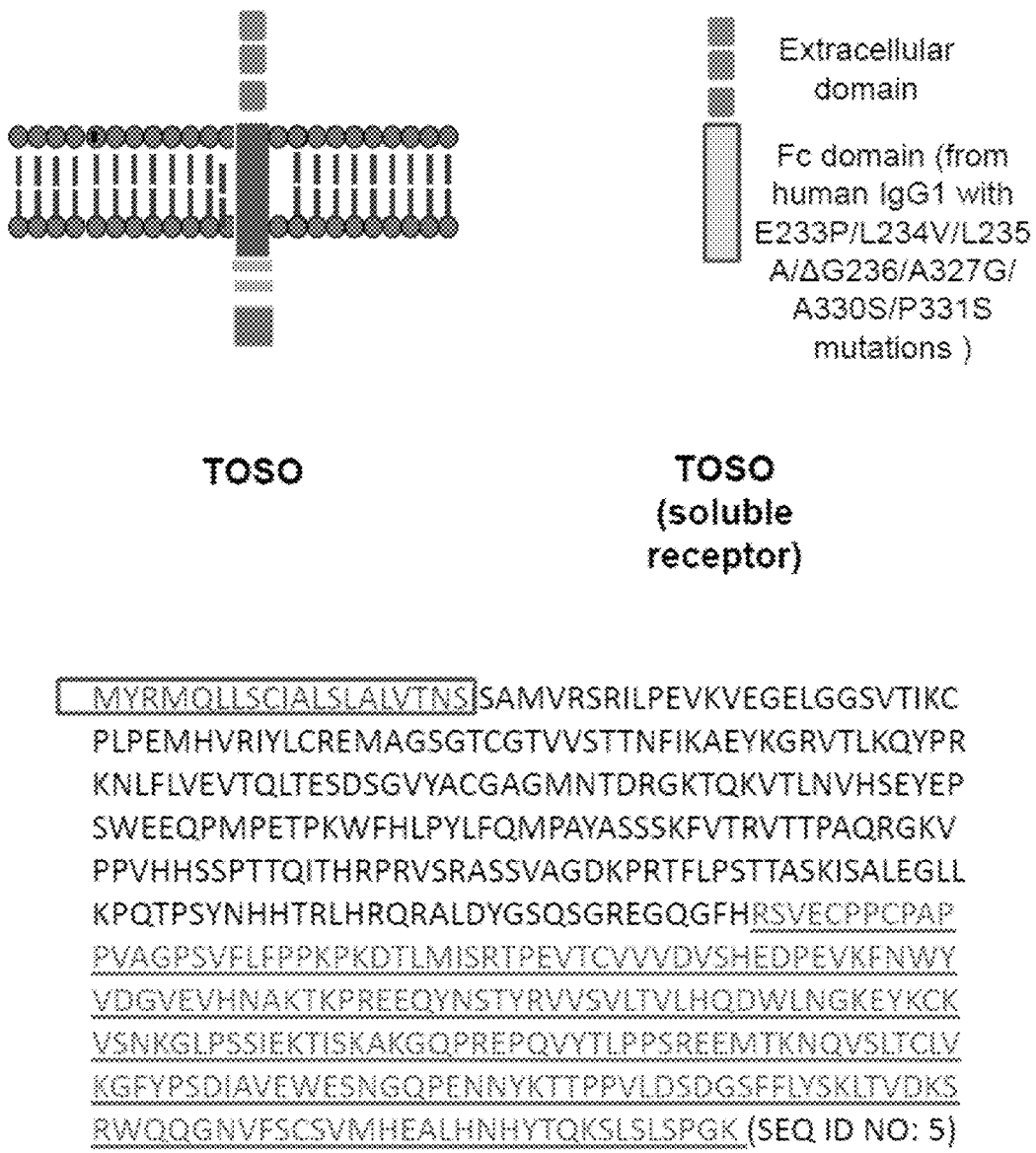

TOSO

TOSO
(soluble
receptor)

Extracellular
domain

Fc domain (from
human IgG1 with
E233P/L234V/L235
A/ΔG236/A327G/
A330S/P331S
mutations )

MYRMQLLSCIALSLALVTNS SAMVRSRILPEVKVEGELGGSVTIKC
PLPEMHVRIYLCREMAGSGTCGTVVSTTNFIKAEYKGRVTLKQYPR
KNLFLVEVTQLTESDSGVYACGAGMNTDRGKTQKVTLNVHSEYEP
SWEEQPMPETPKWFHLPYLFQMPAYASSSKFVTRVTTPAQRGKV
PPVHHSSPTTQITHRPRVSRASSVAGDKPRTFLPSTTASKISALEGLL
KPQTPSYNHHTRLHRQRALDYGSQSGREGQGFHRSVECPPCPAP
PVAGPSVFLFPPKPKDTLMISRTPEVTCVVVDVSHEDPEVKFNWY
VDGVEVHNAKTKPREEQYNSTYRVVSVLTVLHQDWLNGKEYKCK
VSNKGLPSSIEKTISKAKGQPREPQVYTLPPSREEMTKNQVSLTCLV
KGFYPSDIAVEWESNGQPENNYKTTPPVLDSDGSFFLYSKLTVDKS
RWQQGNVFSCSVMHEALHNHYTQKSLSLSPGK (SEQ ID NO: 5)

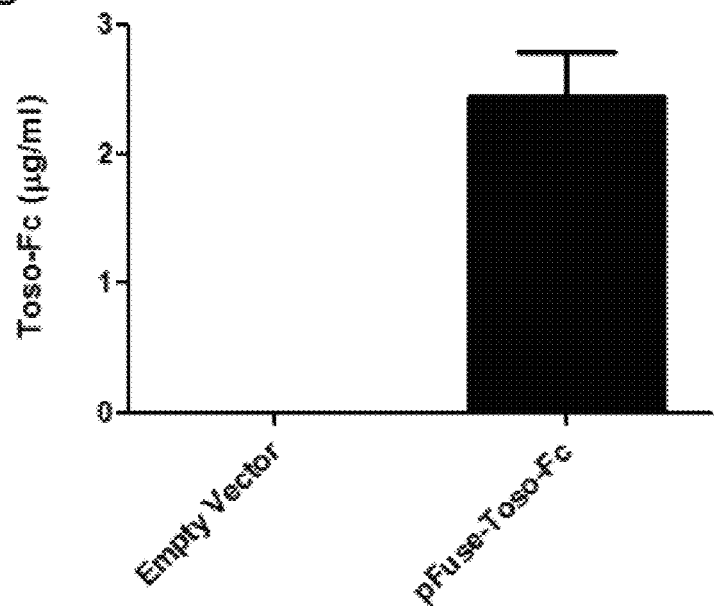
FIG. 8B
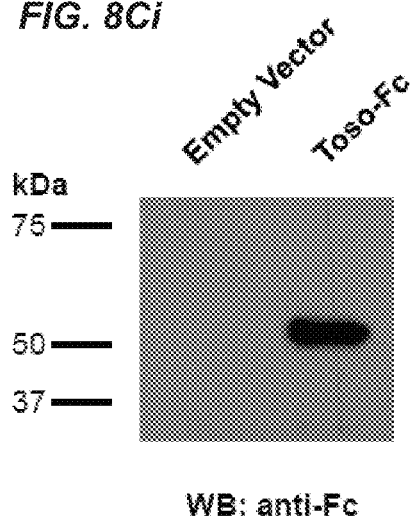
FIG. 8Ci
WB: anti-Fc
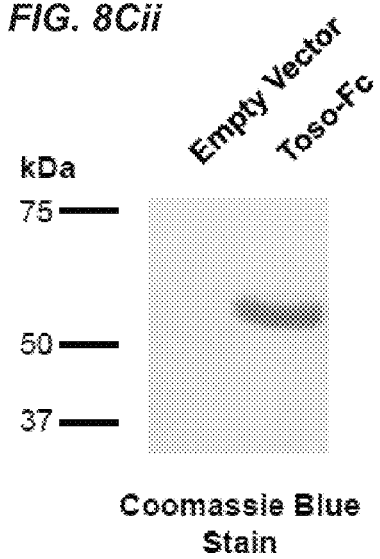
FIG. 8Cii
Coomassie Blue Stain

ISAMVRSRILPEVKVEGELGGSVTIKCPLPEMHVRIYLCREMAG
SGTCGTVVSTTNFIKAEYKGRVTLKQYPRKNLFLVEVTQLTESD
SGVYACGAGMNTDRGKTQKVTLNVHSEYEPSWEEQPMPET
PKWFHLPYLFQMPAYASSSKFVTRVTTPAQRGKVPPVHHSSPT
TQITHRPRVSRASSVAGDKPRTFLPSTTASKISALEGLLKPQTPS
YNHHTRLHRQRALDYGSQSGREGQGFH (SEQ ID NO: 1)

FIG. 10B

MYRMQLLSCIALSLALVTNS (SEQ ID NO: 2)

FIG. 10C

RSVECPPCPAPPVAGPSVFLFPPKPKDTLMISRTPEVTCVVV
DVSHEDPEVKFNWYVDGVEVHNAKTKPREEQYNSTYRVV
SVLTVLHQDWLNGKEYKCKVSNKGLPSSIEKTISKAKGQPRE
PQVYTLPPSREEMTKNQVSLTCLVKGFYPSDIAVEWESNGQ
PENNYKTTPPVLDSDGSFFLYSKLTVDKSRWQQGNVFSCSV
MHEALHNHYTQKSLSLSPGK (SEQ ID NO: 3)

FIG. 10D

AGKPTHVNVSVVMAEVDGTCY (SEQ ID NO: 4)

FIG. 11A

SYRMQLLSCIALSLALVTNSPEVKVEGELGGSVTIKCPLPEMHVRIYLCREMAGSGTCGTVVSTTNFIKAEYKGR
VTLKQYPRKNLFLVEVTQLTESDSGVYACGAGMNTDRGKTQKVTLNVHSEYEPSWEEQPMPETPKWFHLPYL
FQMPAYASSSKFVTRVTTPAQRGKVPPVHHSSPTTQITHRPRVSRASSVAGDKPRTFLPSTTASKISALEGLLKP
QTPSYNHHTRLHRQRALDYGSQSGREGQGFHRSVECPPCPAPPVAGPSVFLFPPKPKDTLMISRTPEVTCVVV
DVSHEDPEVKFNWYVDGVEVHNAKTKPREEQYNSTYRVVSVLTVLHQDWLNGKEYKCKVSNKGLPSSIEKTIS
KAKGQPREPQVYTLPPSREEMTKNQVSLTCLVKGFYPSDIAVEWESNGQPENNYKTTPPVLDSDGSFFLYSKLT
VDKSRWQQGNVFSCSVMHEALHNHYTQKSLSLSPGKAGKPTHVNVSVVMAEVDGTCY (SEQ ID NO: 6)

FIG. 11B

1    MDFWLWPLYF LPVSGALRIL PEVKVEGELG GSVTIKCPLP EMHVRIYLCR EMAGSGTCGT
61   VVSTTNFIKA EYKGRVTLKQ YPRKNLFLVE VTQLTESDSG VYACGAGMNT DRGKTQKVTL
121  NVHSEYEPSW EEQPMPETPK WFHLPYLFQM PAYASSSKFV TRVTTPAQRG KVPPVHHSSP
181  TTQITHRPRV SRASSVAGDK PRTFLPSTTA SKISALEGLL KPQTPSYNHH TRLHRQRALD
241  YGSQSGREGQ GFHILIPTIL GLFLLALLGL VVKRAVERRK ALSRRARRLA VRMRALESSQ
301  RPRGSPRPRS QNNIYSACPR RARGADAAGT GEAPVPGPGA PLPPAPLQVS ESPWLHAPSL
361  KTSCEYVSLY HQPAAMMEDS DSDDYINVPA (SEQ ID NO: 7)

Before sToso Treatment
GTT male

After sToso Treatment
GTT male n=5 per group

FIG. 27A

Extracellular domain

PEVKVEGELGGSVTIKCPLPEMHVRIYLCREMAGSGTCGTVVSTTNFIKAEYKGRVTLKQYPRKNLFLVEVTQLTESDSG
VYACGAGMNTDRGKTQKVTLNVHSEYEPSWEEQPMPETPKWFHLPYLFQMPAYASSSKFVTRVTTPAQRGKVPPVH
HSSPTTQITHRPRVSRASSVAGDKPRTFLPSTTASKISALEGLLKPQTPSYNHHTRLHRQRALDYGSQSGREGQG (SEQ
ID NO. 8)

Delta 21

EMHVRIYLCREMAGSGTCGTVVSTTNFIKAEYKGRVTLKQYPRKNLFLVEVTQLTESDSGVYACGAGMNTDRGKTQKV
TLNVHSEYEPSWEEQPMPETPKWFHLPYLFQMPAYASSSKFVTRVTTPAQRGKVPPVHHSSPTTQITHRPRVSRASSV
AGDKPRTFLPSTTASKISALEGLLKPQTPSYNHHTRLHRQRALDYGSQSGREGQG (SEQ ID NO. 9)

MYRMQLLSCIALSLALVTNSISAMVRSEMHVRIYLCREMAGSGTCGTVVSTTNFIKAEYKGRVTLKQYPRKNLFLVEVTQ
LTESDSGVYACGAGMNTDRGKTQKVTLNVHSEYEPSWEEQPMPETPKWFHLPYLFQMPAYASSSKFVTRVTTPAQR
GKVPPVHHSSPTTQITHRPRVSRASSVAGDKPRTFLPSTTASKISALEGLLKPQTPSYNHHTRLHRQRALDYGSQSGREG
QGFHRSVECPPCPAPPVAGPSVFLFPPKPKDTLMISRTPEVTCVVVDVSHEDPEVKFNWYVDGVEVHNAKTKPREEQY
NSTYRVVSVLTVLHQDWLNGKEYKCKVSNKGLPSSIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSLSLSPGK (SEQ ID
NO: 10)

Delta 35

GTCGTVVSTTNFIKAEYKGRVTLKQYPRKNLFLVEVTQLTESDSGVYACGAGMNTDRGKTQKVTLNVHSEYEPSWEEQ
PMPETPKWFHLPYLFQMPAYASSSKFVTRVTTPAQRGKVPPVHHSSPTTQITHRPRVSRASSVAGDKPRTFLPSTTASKI
SALEGLLKPQTPSYNHHTRLHRQRALDYGSQSGREGQG (SEQ ID NO: 11)

MYRMQLLSCIALSLALVTNSISAMVRSGTCGTVVSTTNFIKAEYKGRVTLKQYPRKNLFLVEVTQLTESDSGVYACGAG
MNTDRGKTQKVTLNVHSEYEPSWEEQPMPETPKWFHLPYLFQMPAYASSSKFVTRVTTPAQRGKVPPVHHSSPTTQI
THRPRVSRASSVAGDKPRTFLPSTTASKISALEGLLKPQTPSYNHHTRLHRQRALDYGSQSGREGQGFHRSVECPPCPAP
PVAGPSVFLFPPKPKDTLMISRTPEVTCVVVDVSHEDPEVKFNWYVDGVEVHNAKTKPREEQYNSTYRVVSVLTVLHQ
DWLNGKEYKCKVSNKGLPSSIEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPGK (SEQ ID NO: 12)

FIG. 27B

Delta 87

GMNTDRGKTQKVTLNVHSEYEPSWEEQPMPETPKWFHLPYLFQMPAYASSSKFVTRVTTPAQRGKVPPVHHSSPTT
QITHRPRVSRASSVAGDKPRTFLPSTTASKISALEGLLKPQTPSYNHHTRLHRQRALDYGSQSGREGQG (SEQ ID NO: 13)

MYRMQLLSCIALSLALVTNSISAMVRSGMNTDRGKTQKVTLNVHSEYEPSWEEQPMPETPKWFHLPYLFQMPAYASS
SKFVTRVTTPAQRGKVPPVHHSSPTTQITHRPRVSRASSVAGDKPRTFLPSTTASKISALEGLLKPQTPSYNHHTRLHRQR
ALDYGSQSGREGQGFHRSVECPPCPAPPVAGPSVFLFPPKPKDTLMISRTPEVTCVVVDVSHEDPEVKFNWYVDGVEV
HNAKTKPREEQYNSTYRVVSVLTVLHQDWLNGKEYKCKVSNKGLPSSIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSVMHEALHNHYTQKSL
SLSPGK (SEQ ID NO: 14)

Delta 21 to 210

EMHVRIYLCREMAGSGTCGTVVSTTNFIKAEYKGRVTLKQYPRKNLFLVEVTQLTESDSGVYACGAGMNTDRGKTQKV
TLNVHSEYEPSWEEQPMPETPKWFHLPYLFQMPAYASSSKFVTRVTTPAQRGKVPPVHHSSPTTQITHRPRVSRASSV
AGDKPRTFLPSTTASKISALEGLLKPQTPSYNHHTR (SEQ ID NO: 15)

MYRMQLLSCIALSLALVTNSISAMVRSEMHVRIYLCREMAGSGTCGTVVSTTNFIKAEYKGRVTLKQYPRKNLFLVEVTQ
LTESDSGVYACGAGMNTDRGKTQKVTLNVHSEYEPSWEEQPMPETPKWFHLPYLFQMPAYASSSKFVTRVTTPAQR
GKVPPVHHSSPTTQITHRPRVSRASSVAGDKPRTFLPSTTASKISALEGLLKPQTPSYNHHTRRSVECPPCPAPPVAGPSV
FLFPPKPKDTLMISRTPEVTCVVVDVSHEDPEVKFNWYVDGVEVHNAKTKPREEQYNSTYRVVSVLTVLHQDWLNGKE
YKCKVSNKGLPSSIEKTISKAKGQPREPQVYTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK (SEQ ID NO: 16)

1 to 210

RILPEVKVEGELGGSVTIKCPLPEMHVRIYLCREMAGSGTCGTVVSTTNFIKAEYKGRVTLKQYPRKNLFLVEVTQLTESD
SGVYACGAGMNTDRGKTQKVTLNVHSEYEPSWEEQPMPETPKWFHLPYLFQMPAYASSSKFVTRVTTPAQRGKVPP
VHHSSPTTQITHRPRVSRASSVAGDKPRTFLPSTTASKISALEGLLKPQTPSYNHHTR (SEQ ID NO: 17)

MYRMQLLSCIALSLALVTNSISAMVRSRILPEVKVEGELGGSVTIKCPLPEMHVRIYLCREMAGSGTCGTVVSTTNFIKAE
YKGRVTLKQYPRKNLFLVEVTQLTESDSGVYACGAGMNTDRGKTQKVTLNVHSEYEPSWEEQPMPETPKWFHLPYLF
QMPAYASSSKFVTRVTTPAQRGKVPPVHHSSPTTQITHRPRVSRASSVAGDKPRTFLPSTTASKISALEGLLKPQTPSYN
HHTRRSVECPPCPAPPVAGPSVFLFPPKPKDTLMISRTPEVTCVVVDVSHEDPEVKFNWYVDGVEVHNAKTKPREEQY
NSTYRVVSVLTVLHQDWLNGKEYKCKVSNKGLPSSIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSLSLSPGK (SEQ ID NO: 18)

RILPEVKVEGELGGSVTIKCPLPEMHVRIYLCREMAGSGTCGTVVSTTNFIKAEYKGRVTLKQYPRKNLFLVEVTQLTESD
SGVYACGAGMNTDRGKTQKVTLNVHSEYEPSWEEQPMPETPKWFHLPYLFQMPAYASSSKFVTRVTTPAQRGKV
(SEQ ID NO: 19)

MYRMQLLSCIALSLALVTNSISAMVRSRILPEVKVEGELGGSVTIKCPLPEMHVRIYLCREMAGSGTCGTVVSTTNFIKAE
YKGRVTLKQYPRKNLFLVEVTQLTESDSGVYACGAGMNTDRGKTQKVTLNVHSEYEPSWEEQPMPETPKWFHLPYLF
QMPAYASSSKFVTRVTTPAQRGKVRSVECPPCPAPPVAGPSVFLFPPKPKDTLMISRTPEVTCVVVDVSHEDPEVKFN
WYVDGVEVHNAKTKPREEQYNSTYRVVSVLTVLHQDWLNGKEYKCKVSNKGLPSSIEKTISKAKGQPREPQVYTLPPSR
EEMTKNQVSLTCLVKGFYPSDIAVEWESNGQPENNYKTTPPVLDSDGSFFLYSKLTVDKSRWQQGNVFSCSVMHEAL
HNHYTQKSLSLSPGK (SEQ ID NO: 20)

1 to 104

RILPEVKVEGELGGSVTIKCPLPEMHVRIYLCREMAGSGTCGTVVSTTNFIKAEYKGRVTLKQYPRKNLFLVEVTQLTESD
SGVYACGAGMNTDRGKTQKVTLNVH (SEQ ID NO: 21)

MYRMQLLSCIALSLALVTNSISAMVRSRILPEVKVEGELGGSVTIKCPLPEMHVRIYLCREMAGSGTCGTVVSTTNFIKAE
YKGRVTLKQYPRKNLFLVEVTQLTESDSGVYACGAGMNTDRGKTQKVTLNVHRSVECPPCPAPPVAGPSVFLFPPKPK
DTLMISRTPEVTCVVVDVSHEDPEVKFNWYVDGVEVHNAKTKPREEQYNSTYRVVSVLTVLHQDWLNGKEYKCKVSN
KGLPSSIEKTISKAKGQPREPQVYTLPPSREEMTKNQVSLTCLVKGFYPSDIAVEWESNGQPENNYKTTPPVLDSDGSFFL
YSKLTVDKSRWQQGNVFSCSVMHEALHNHYTQKSLSLSPGK (SEQ ID NO: 22)

1 to 92

RILPEVKVEGELGGSVTIKCPLPEMHVRIYLCREMAGSGTCGTVVSTTNFIKAEYKGRVTLKQYPRKNLFLVEVTQLTESD
SGVYACGAGMNTD (SEQ ID NO: 23)

MYRMQLLSCIALSLALVTNSISAMVRSRILPEVKVEGELGGSVTIKCPLPEMHVRIYLCREMAGSGTCGTVVSTTNFIKAE
YKGRVTLKQYPRKNLFLVEVTQLTESDSGVYACGAGMNTDRSVECPPCPAPPVAGPSVFLFPPKPKDTLMISRTPEVTC
VVVDVSHEDPEVKFNWYVDGVEVHNAKTKPREEQYNSTYRVVSVLTVLHQDWLNGKEYKCKVSNKGLPSSIEKTISKA
KGQPREPQVYTLPPSREEMTKNQVSLTCLVKGFYPSDIAVEWESNGQPENNYKTTPPVLDSDGSFFLYSKLTVDKSRW
QQGNVFSCSVMHEALHNHYTQKSLSLSPGK (SEQ ID NO: 24)

SEQUENCE LISTING

<160> NUMBER OF SEQ ID NOS: 30

<210> SEQ ID NO 1
<211> LENGTH: 243
<212> TYPE: PRT
<213> ORGANISM: Artificial Sequence
<220> FEATURE:
<223> OTHER INFORMATION: soluble Toso protein

<400> SEQUENCE: 1

Ile Ser Ala Met Val Arg Ser Arg Ile Leu Pro Glu Val Lys Val Glu
1               5                   10                  15

Gly Glu Leu Gly Gly Ser Val Thr Ile Lys Cys Pro Leu Pro Glu Met
                20                  25                  30

His Val Arg Ile Tyr Leu Cys Arg Glu Met Ala Gly Ser Gly Thr Cys
            35                  40                  45

Gly Thr Val Val Ser Thr Thr Asn Phe Ile Lys Ala Glu Tyr Lys Gly
        50                  55                  60

Arg Val Thr Leu Lys Gln Tyr Pro Arg Lys Asn Leu Phe Leu Val Glu
65                  70                  75                  80

Val Thr Gln Leu Thr Glu Ser Asp Ser Gly Val Tyr Ala Cys Gly Ala
                85                  90                  95

Gly Met Asn Thr Asp Arg Gly Lys Thr Gln Lys Val Thr Leu Asn Val
            100                 105                 110

His Ser Glu Tyr Glu Pro Ser Trp Glu Glu Gln Pro Met Pro Glu Thr
        115                 120                 125

Pro Lys Trp Phe His Leu Pro Tyr Leu Phe Gln Met Pro Ala Tyr Ala
130                 135                 140

Ser Ser Ser Lys Phe Val Thr Arg Val Thr Thr Pro Ala Gln Arg Gly
145                 150                 155                 160

Lys Val Pro Pro Val His His Ser Ser Pro Thr Thr Gln Ile Thr His
                165                 170                 175

Arg Pro Arg Val Ser Arg Ala Ser Ser Val Ala Gly Asp Lys Pro Arg
            180                 185                 190

Thr Phe Leu Pro Ser Thr Thr Ala Ser Lys Ile Ser Ala Leu Glu Gly
        195                 200                 205

Leu Leu Lys Pro Gln Thr Pro Ser Tyr Asn His His Thr Arg Leu His
210                 215                 220

Arg Gln Arg Ala Leu Asp Tyr Gly Ser Gln Ser Gly Arg Glu Gly Gln
225                 230                 235                 240

Gly Phe His

<210> SEQ ID NO 2
<211> LENGTH: 20
<212> TYPE: PRT
<213> ORGANISM: Artificial Sequence
<220> FEATURE:
<223> OTHER INFORMATION: soluble Toso protein

<400> SEQUENCE: 2

Met Tyr Arg Met Gln Leu Leu Ser Cys Ile Ala Leu Ser Leu Ala Leu
1               5                   10                  15

Val Thr Asn Ser
            20

-continued

```
<210> SEQ ID NO 3
<211> LENGTH: 225
<212> TYPE: PRT
<213> ORGANISM: Artificial Sequence
<220> FEATURE:
<223> OTHER INFORMATION: soluble Toso protein

<400> SEQUENCE: 3

Arg Ser Val Glu Cys Pro Pro Cys Pro Ala Pro Pro Val Ala Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Gly Leu Pro Ser Ser Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 4
<211> LENGTH: 21
<212> TYPE: PRT
<213> ORGANISM: Artificial Sequence
<220> FEATURE:
<223> OTHER INFORMATION: soluble Toso protein

<400> SEQUENCE: 4

Ala Gly Lys Pro Thr His Val Asn Val Ser Val Val Met Ala Glu Val
1               5                   10                  15

Asp Gly Thr Cys Tyr
            20

<210> SEQ ID NO 5
<211> LENGTH: 488
<212> TYPE: PRT
<213> ORGANISM: Artificial Sequence
<220> FEATURE:
<223> OTHER INFORMATION: soluble Toso protein
```

```
<400> SEQUENCE: 5

Met Tyr Arg Met Gln Leu Leu Ser Cys Ile Ala Leu Ser Leu Ala Leu
1               5                   10                  15

Val Thr Asn Ser Ile Ser Ala Met Val Arg Ser Arg Ile Leu Pro Glu
            20                  25                  30

Val Lys Val Glu Gly Glu Leu Gly Ser Val Thr Ile Lys Cys Pro
        35                  40                  45

Leu Pro Glu Met His Val Arg Ile Tyr Leu Cys Arg Glu Met Ala Gly
    50                  55                  60

Ser Gly Thr Cys Gly Thr Val Ser Thr Thr Asn Phe Ile Lys Ala
65              70                  75                  80

Glu Tyr Lys Gly Arg Val Thr Leu Lys Gln Tyr Pro Arg Lys Asn Leu
                85                  90                  95

Phe Leu Val Glu Val Thr Gln Leu Thr Glu Ser Asp Ser Gly Val Tyr
            100                 105                 110

Ala Cys Gly Ala Gly Met Asn Thr Asp Arg Gly Lys Thr Gln Lys Val
        115                 120                 125

Thr Leu Asn Val His Ser Glu Tyr Glu Pro Ser Trp Glu Glu Gln Pro
    130                 135                 140

Met Pro Glu Thr Pro Lys Trp Phe His Leu Pro Tyr Leu Phe Gln Met
145                 150                 155                 160

Pro Ala Tyr Ala Ser Ser Ser Lys Phe Val Thr Arg Val Thr Thr Pro
                165                 170                 175

Ala Gln Arg Gly Lys Val Pro Pro Val His Ser Ser Pro Thr Thr
            180                 185                 190

Gln Ile Thr His Arg Pro Arg Val Ser Arg Ala Ser Ser Val Ala Gly
        195                 200                 205

Asp Lys Pro Arg Thr Phe Leu Pro Ser Thr Thr Ala Ser Lys Ile Ser
    210                 215                 220

Ala Leu Glu Gly Leu Leu Lys Pro Gln Thr Pro Ser Tyr Asn His His
225                 230                 235                 240

Thr Arg Leu His Arg Gln Arg Ala Leu Asp Tyr Gly Ser Gln Ser Gly
                245                 250                 255

Arg Glu Gly Gln Gly Phe His Arg Ser Val Glu Cys Pro Pro Cys Pro
            260                 265                 270

Ala Pro Pro Val Ala Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Gly
        355                 360                 365

Leu Pro Ser Ser Ile Glu Lys Thr Ile Ser Lys Ala Lys Gly Gln Pro
    370                 375                 380

Arg Glu Pro Gln Val Tyr Thr Leu Pro Pro Ser Arg Glu Glu Met Thr
385                 390                 395                 400

Lys Asn Gln Val Ser Leu Thr Cys Leu Val Lys Gly Phe Tyr Pro Ser
                405                 410                 415
```

```
Asp Ile Ala Val Glu Trp Glu Ser Asn Gly Gln Pro Glu Asn Asn Tyr
                420                 425                 430

Lys Thr Thr Pro Pro Val Leu Asp Ser Asp Gly Ser Phe Phe Leu Tyr
            435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Lys
                485

<210> SEQ ID NO 6
<211> LENGTH: 499
<212> TYPE: PRT
<213> ORGANISM: Artificial Sequence
<220> FEATURE:
<223> OTHER INFORMATION: soluble Toso protein

<400> SEQUENCE: 6

Ser Tyr Arg Met Gln Leu Leu Ser Cys Ile Ala Leu Ser Leu Ala Leu
1               5                   10                  15

Val Thr Asn Ser Pro Glu Val Lys Val Glu Gly Glu Leu Gly Gly Ser
            20                  25                  30

Val Thr Ile Lys Cys Pro Leu Pro Glu Met His Val Arg Ile Tyr Leu
        35                  40                  45

Cys Arg Glu Met Ala Gly Ser Gly Thr Cys Gly Thr Val Val Ser Thr
    50                  55                  60

Thr Asn Phe Ile Lys Ala Glu Tyr Lys Gly Arg Val Thr Leu Lys Gln
65                  70                  75                  80

Tyr Pro Arg Lys Asn Leu Phe Leu Val Glu Val Thr Gln Leu Thr Glu
                85                  90                  95

Ser Asp Ser Gly Val Tyr Ala Cys Gly Ala Gly Met Asn Thr Asp Arg
            100                 105                 110

Gly Lys Thr Gln Lys Val Thr Leu Asn Val His Ser Glu Tyr Glu Pro
        115                 120                 125

Ser Trp Glu Glu Gln Pro Met Pro Glu Thr Pro Lys Trp Phe His Leu
    130                 135                 140

Pro Tyr Leu Phe Gln Met Pro Ala Tyr Ala Ser Ser Ser Lys Phe Val
145                 150                 155                 160

Thr Arg Val Thr Thr Pro Ala Gln Arg Gly Lys Val Pro Pro Val His
                165                 170                 175

His Ser Ser Pro Thr Thr Gln Ile Thr His Arg Pro Arg Val Ser Arg
            180                 185                 190

Ala Ser Ser Val Ala Gly Asp Lys Pro Arg Thr Phe Leu Pro Ser Thr
        195                 200                 205

Thr Ala Ser Lys Ile Ser Ala Leu Glu Gly Leu Leu Lys Pro Gln Thr
    210                 215                 220

Pro Ser Tyr Asn His His Thr Arg Leu His Arg Gln Arg Ala Leu Asp
225                 230                 235                 240

Tyr Gly Ser Gln Ser Gly Arg Glu Gly Gln Gly Phe His Arg Ser Val
                245                 250                 255

Glu Cys Pro Pro Cys Pro Ala Pro Val Ala Gly Pro Ser Val Phe
            260                 265                 270

Leu Phe Pro Pro Lys Pro Lys Asp Thr Leu Met Ile Ser Arg Thr Pro
        275                 280                 285
```

```
Glu Val Thr Cys Val Val Asp Val Ser His Glu Asp Pro Glu Val
            290                 295                 300
Lys Phe Asn Trp Tyr Val Asp Gly Val Glu Val His Asn Ala Lys Thr
305                 310                 315                 320
Lys Pro Arg Glu Glu Gln Tyr Asn Ser Thr Tyr Arg Val Val Ser Val
                325                 330                 335
Leu Thr Val Leu His Gln Asp Trp Leu Asn Gly Lys Glu Tyr Lys Cys
            340                 345                 350
Lys Val Ser Asn Lys Gly Leu Pro Ser Ser Ile Glu Lys Thr Ile Ser
            355                 360                 365
Lys Ala Lys Gly Gln Pro Arg Glu Pro Gln Val Tyr Thr Leu Pro Pro
370                 375                 380
Ser Arg Glu Glu Met Thr Lys Asn Gln Val Ser Leu Thr Cys Leu Val
385                 390                 395                 400
Lys Gly Phe Tyr Pro Ser Asp Ile Ala Val Glu Trp Glu Ser Asn Gly
                405                 410                 415
Gln Pro Glu Asn Asn Tyr Lys Thr Thr Pro Pro Val Leu Asp Ser Asp
            420                 425                 430
Gly Ser Phe Phe Leu Tyr Ser Lys Leu Thr Val Asp Lys Ser Arg Trp
            435                 440                 445
Gln Gln Gly Asn Val Phe Ser Cys Ser Val Met His Glu Ala Leu His
450                 455                 460
Asn His Tyr Thr Gln Lys Ser Leu Ser Leu Ser Pro Gly Lys Ala Gly
465                 470                 475                 480
Lys Pro Thr His Val Asn Val Ser Val Val Met Ala Glu Val Asp Gly
                485                 490                 495
Thr Cys Tyr

<210> SEQ ID NO 7
<211> LENGTH: 390
<212> TYPE: PRT
<213> ORGANISM: Artificial Sequence
<220> FEATURE:
<223> OTHER INFORMATION: soluble Toso protein

<400> SEQUENCE: 7

Met Asp Phe Trp Leu Trp Pro Leu Tyr Phe Leu Pro Val Ser Gly Ala
1               5                   10                  15
Leu Arg Ile Leu Pro Glu Val Lys Val Glu Gly Glu Leu Gly Gly Ser
                20                  25                  30
Val Thr Ile Lys Cys Pro Leu Pro Glu Met His Val Arg Ile Tyr Leu
            35                  40                  45
Cys Arg Glu Met Ala Gly Ser Gly Thr Cys Gly Thr Val Val Ser Thr
50                  55                  60
Thr Asn Phe Ile Lys Ala Glu Tyr Lys Gly Arg Val Thr Leu Lys Gln
65                  70                  75                  80
Tyr Pro Arg Lys Asn Leu Phe Leu Val Glu Val Thr Gln Leu Thr Glu
                85                  90                  95
Ser Asp Ser Gly Val Tyr Ala Cys Gly Ala Gly Met Asn Thr Asp Arg
            100                 105                 110
Gly Lys Thr Gln Lys Val Thr Leu Asn Val His Ser Glu Tyr Glu Pro
        115                 120                 125
Ser Trp Glu Glu Gln Pro Met Pro Glu Thr Pro Lys Trp Phe His Leu
    130                 135                 140
```

```
Pro Tyr Leu Phe Gln Met Pro Ala Tyr Ala Ser Ser Lys Phe Val
145                 150                 155                 160

Thr Arg Val Thr Thr Pro Ala Gln Arg Gly Lys Val Pro Val His
            165                 170                 175

His Ser Ser Pro Thr Thr Gln Ile Thr His Arg Pro Arg Val Ser Arg
            180                 185                 190

Ala Ser Ser Val Ala Gly Asp Lys Pro Arg Thr Phe Leu Pro Ser Thr
            195                 200                 205

Thr Ala Ser Lys Ile Ser Ala Leu Glu Gly Leu Leu Lys Pro Gln Thr
    210                 215                 220

Pro Ser Tyr Asn His His Thr Arg Leu His Arg Gln Arg Ala Leu Asp
225                 230                 235                 240

Tyr Gly Ser Gln Ser Gly Arg Glu Gly Gln Gly Phe His Ile Leu Ile
                245                 250                 255

Pro Thr Ile Leu Gly Leu Phe Leu Leu Ala Leu Leu Gly Leu Val Val
            260                 265                 270

Lys Arg Ala Val Glu Arg Arg Lys Ala Leu Ser Arg Arg Ala Arg Arg
            275                 280                 285

Leu Ala Val Arg Met Arg Ala Leu Glu Ser Ser Gln Arg Pro Arg Gly
    290                 295                 300

Ser Pro Arg Pro Arg Ser Gln Asn Asn Ile Tyr Ser Ala Cys Pro Arg
305                 310                 315                 320

Arg Ala Arg Gly Ala Asp Ala Ala Gly Thr Glu Ala Pro Val Pro
                325                 330                 335

Gly Pro Gly Ala Pro Leu Pro Ala Pro Leu Gln Val Ser Glu Ser
            340                 345                 350

Pro Trp Leu His Ala Pro Ser Leu Lys Thr Ser Cys Glu Tyr Val Ser
            355                 360                 365

Leu Tyr His Gln Pro Ala Ala Met Met Glu Asp Ser Asp Ser Asp
    370                 375                 380

Tyr Ile Asn Val Pro Ala
385                 390

<210> SEQ ID NO 8
<211> LENGTH: 231
<212> TYPE: PRT
<213> ORGANISM: Artificial Sequence
<220> FEATURE:
<223> OTHER INFORMATION: soluble Toso protein

<400> SEQUENCE: 8

Pro Glu Val Lys Val Glu Gly Glu Leu Gly Gly Ser Val Thr Ile Lys
1               5                   10                  15

Cys Pro Leu Pro Glu Met His Val Arg Ile Tyr Leu Cys Arg Glu Met
                20                  25                  30

Ala Gly Ser Gly Thr Cys Gly Thr Val Val Ser Thr Thr Asn Phe Ile
            35                  40                  45

Lys Ala Glu Tyr Lys Gly Arg Val Thr Leu Lys Gln Tyr Pro Arg Lys
    50                  55                  60

Asn Leu Phe Leu Val Glu Val Thr Gln Leu Thr Glu Ser Asp Ser Gly
65                  70                  75                  80

Val Tyr Ala Cys Gly Ala Gly Met Asn Thr Asp Arg Gly Lys Thr Gln
                85                  90                  95

Lys Val Thr Leu Asn Val His Ser Glu Tyr Glu Pro Ser Trp Glu Glu
                100                 105                 110
```

```
Gln Pro Met Pro Glu Thr Pro Lys Trp Phe His Leu Pro Tyr Leu Phe
            115                 120                 125

Gln Met Pro Ala Tyr Ala Ser Ser Ser Lys Phe Val Thr Arg Val Thr
        130                 135                 140

Thr Pro Ala Gln Arg Gly Lys Val Pro Val His His Ser Ser Pro
145                 150                 155                 160

Thr Thr Gln Ile Thr His Arg Pro Arg Val Ser Arg Ala Ser Ser Val
                165                 170                 175

Ala Gly Asp Lys Pro Arg Thr Phe Leu Pro Ser Thr Thr Ala Ser Lys
            180                 185                 190

Ile Ser Ala Leu Glu Gly Leu Leu Lys Pro Gln Thr Pro Ser Tyr Asn
        195                 200                 205

His His Thr Arg Leu His Arg Gln Arg Ala Leu Asp Tyr Gly Ser Gln
    210                 215                 220

Ser Gly Arg Glu Gly Gln Gly
225                 230

<210> SEQ ID NO 9
<211> LENGTH: 211
<212> TYPE: PRT
<213> ORGANISM: Artificial Sequence
<220> FEATURE:
<223> OTHER INFORMATION: soluble Toso protein

<400> SEQUENCE: 9

Glu Met His Val Arg Ile Tyr Leu Cys Arg Glu Met Ala Gly Ser Gly
1               5                   10                  15

Thr Cys Gly Thr Val Val Ser Thr Thr Asn Phe Ile Lys Ala Glu Tyr
            20                  25                  30

Lys Gly Arg Val Thr Leu Lys Gln Tyr Pro Arg Lys Asn Leu Phe Leu
        35                  40                  45

Val Glu Val Thr Gln Leu Thr Glu Ser Asp Ser Gly Val Tyr Ala Cys
    50                  55                  60

Gly Ala Gly Met Asn Thr Asp Arg Gly Lys Thr Gln Lys Val Thr Leu
65                  70                  75                  80

Asn Val His Ser Glu Tyr Glu Pro Ser Trp Glu Glu Gln Pro Met Pro
                85                  90                  95

Glu Thr Pro Lys Trp Phe His Leu Pro Tyr Leu Phe Gln Met Pro Ala
            100                 105                 110

Tyr Ala Ser Ser Ser Lys Phe Val Thr Arg Val Thr Thr Pro Ala Gln
        115                 120                 125

Arg Gly Lys Val Pro Val His His Ser Ser Pro Thr Thr Gln Ile
    130                 135                 140

Thr His Arg Pro Arg Val Ser Arg Ala Ser Ser Val Ala Gly Asp Lys
145                 150                 155                 160

Pro Arg Thr Phe Leu Pro Ser Thr Thr Ala Ser Lys Ile Ser Ala Leu
                165                 170                 175

Glu Gly Leu Leu Lys Pro Gln Thr Pro Ser Tyr Asn His His Thr Arg
            180                 185                 190

Leu His Arg Gln Arg Ala Leu Asp Tyr Gly Ser Gln Ser Gly Arg Glu
        195                 200                 205

Gly Gln Gly
    210
```

<210> SEQ ID NO 10
<211> LENGTH: 465
<212> TYPE: PRT
<213> ORGANISM: Artificial Sequence
<220> FEATURE:
<223> OTHER INFORMATION: soluble Toso protein

<400> SEQUENCE: 10

```
Met Tyr Arg Met Gln Leu Leu Ser Cys Ile Ala Leu Ser Leu Ala Leu
1               5                   10                  15

Val Thr Asn Ser Ile Ser Ala Met Val Arg Ser Glu Met His Val Arg
            20                  25                  30

Ile Tyr Leu Cys Arg Glu Met Ala Gly Ser Gly Thr Cys Gly Thr Val
        35                  40                  45

Val Ser Thr Thr Asn Phe Ile Lys Ala Glu Tyr Lys Gly Arg Val Thr
    50                  55                  60

Leu Lys Gln Tyr Pro Arg Lys Asn Leu Phe Leu Val Glu Val Thr Gln
65                  70                  75                  80

Leu Thr Glu Ser Asp Ser Gly Val Tyr Ala Cys Gly Ala Gly Met Asn
                85                  90                  95

Thr Asp Arg Gly Lys Thr Gln Lys Val Thr Leu Asn Val His Ser Glu
            100                 105                 110

Tyr Glu Pro Ser Trp Glu Glu Gln Pro Met Pro Glu Thr Pro Lys Trp
        115                 120                 125

Phe His Leu Pro Tyr Leu Phe Gln Met Pro Ala Tyr Ala Ser Ser Ser
    130                 135                 140

Lys Phe Val Thr Arg Val Thr Thr Pro Ala Gln Arg Gly Lys Val Pro
145                 150                 155                 160

Pro Val His His Ser Ser Pro Thr Thr Gln Ile Thr His Arg Pro Arg
                165                 170                 175

Val Ser Arg Ala Ser Ser Val Ala Gly Asp Lys Pro Arg Thr Phe Leu
            180                 185                 190

Pro Ser Thr Thr Ala Ser Lys Ile Ser Ala Leu Glu Gly Leu Leu Lys
        195                 200                 205

Pro Gln Thr Pro Ser Tyr Asn His His Thr Arg Leu His Arg Gln Arg
    210                 215                 220

Ala Leu Asp Tyr Gly Ser Gln Ser Gly Arg Glu Gly Gln Gly Phe His
225                 230                 235                 240

Arg Ser Val Glu Cys Pro Pro Cys Pro Ala Pro Val Ala Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365
```

```
Leu Pro Pro Ser Arg Glu Glu Met Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
            405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
450                 455                 460

Lys
465

<210> SEQ ID NO 11
<211> LENGTH: 196
<212> TYPE: PRT
<213> ORGANISM: Artificial Sequence
<220> FEATURE:
<223> OTHER INFORMATION: soluble Toso protein

<400> SEQUENCE: 11

Gly Thr Cys Gly Thr Val Val Ser Thr Thr Asn Phe Ile Lys Ala Glu
1               5                   10                  15

Tyr Lys Gly Arg Val Thr Leu Lys Gln Tyr Pro Arg Lys Asn Leu Phe
                20                  25                  30

Leu Val Glu Val Thr Gln Leu Thr Glu Ser Asp Ser Gly Val Tyr Ala
            35                  40                  45

Cys Gly Ala Gly Met Asn Thr Asp Arg Gly Lys Thr Gln Lys Val Thr
50                  55                  60

Leu Asn Val His Ser Glu Tyr Glu Pro Ser Trp Glu Glu Gln Pro Met
65                  70                  75                  80

Pro Glu Thr Pro Lys Trp Phe His Leu Pro Tyr Leu Phe Gln Met Pro
                85                  90                  95

Ala Tyr Ala Ser Ser Lys Phe Val Thr Arg Val Thr Thr Pro Ala
                100                 105                 110

Gln Arg Gly Lys Val Pro Pro Val His His Ser Ser Pro Thr Thr Gln
            115                 120                 125

Ile Thr His Arg Pro Arg Val Ser Arg Ala Ser Ser Val Ala Gly Asp
130                 135                 140

Lys Pro Arg Thr Phe Leu Pro Ser Thr Thr Ala Ser Lys Ile Ser Ala
145                 150                 155                 160

Leu Glu Gly Leu Leu Lys Pro Gln Thr Pro Ser Tyr Asn His His Thr
                165                 170                 175

Arg Leu His Arg Gln Arg Ala Leu Asp Tyr Gly Ser Gly Ser Gly Arg
            180                 185                 190

Glu Gly Gln Gly
        195

<210> SEQ ID NO 12
<211> LENGTH: 450
<212> TYPE: PRT
<213> ORGANISM: Artificial Sequence
<220> FEATURE:
<223> OTHER INFORMATION: soluble Toso protein
```

```
<400> SEQUENCE: 12

Met Tyr Arg Met Gln Leu Leu Ser Cys Ile Ala Leu Ser Leu Ala Leu
1               5                   10                  15

Val Thr Asn Ser Ile Ser Ala Met Val Arg Ser Gly Thr Cys Gly Thr
            20                  25                  30

Val Val Ser Thr Thr Asn Phe Ile Lys Ala Glu Tyr Lys Gly Arg Val
        35                  40                  45

Thr Leu Lys Gln Tyr Pro Arg Lys Asn Leu Phe Leu Val Glu Val Thr
    50                  55                  60

Gln Leu Thr Glu Ser Asp Ser Gly Val Tyr Ala Cys Gly Ala Gly Met
65                  70                  75                  80

Asn Thr Asp Arg Gly Lys Thr Gln Lys Val Thr Leu Asn Val His Ser
                85                  90                  95

Glu Tyr Glu Pro Ser Trp Glu Gln Pro Met Pro Glu Thr Pro Lys
            100                 105                 110

Trp Phe His Leu Pro Tyr Leu Phe Gln Met Pro Ala Tyr Ala Ser Ser
            115                 120                 125

Ser Lys Phe Val Thr Arg Val Thr Thr Pro Ala Gln Arg Gly Lys Val
        130                 135                 140

Pro Pro Val His His Ser Ser Pro Thr Thr Gln Ile Thr His Arg Pro
145                 150                 155                 160

Arg Val Ser Arg Ala Ser Ser Val Ala Gly Asp Lys Pro Arg Thr Phe
                165                 170                 175

Leu Pro Ser Thr Thr Ala Ser Lys Ile Ser Ala Leu Glu Gly Leu Leu
            180                 185                 190

Lys Pro Gln Thr Pro Ser Tyr Asn His His Thr Arg Leu His Arg Gln
        195                 200                 205

Arg Ala Leu Asp Tyr Gly Ser Gln Ser Gly Arg Glu Gly Gln Gly Phe
    210                 215                 220

His Arg Ser Val Glu Cys Pro Pro Cys Pro Ala Pro Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 13
<211> LENGTH: 145
<212> TYPE: PRT
<213> ORGANISM: Artificial Sequence
<220> FEATURE:
<223> OTHER INFORMATION: soluble Toso protein

<400> SEQUENCE: 13

Gly Met Asn Thr Asp Arg Gly Lys Thr Gln Lys Val Thr Leu Asn Val
1               5                   10                  15

His Ser Glu Tyr Glu Pro Ser Trp Glu Glu Gln Pro Met Pro Glu Thr
            20                  25                  30

Pro Lys Trp Phe His Leu Pro Tyr Leu Phe Gln Met Pro Ala Tyr Ala
            35                  40                  45

Ser Ser Ser Lys Phe Val Thr Arg Val Thr Thr Pro Ala Gln Arg Gly
    50                  55                  60

Lys Val Pro Pro Val His His Ser Ser Pro Thr Thr Gln Ile Thr His
65                  70                  75                  80

Arg Pro Arg Val Ser Arg Ala Ser Ser Val Ala Gly Asp Lys Pro Arg
                85                  90                  95

Thr Phe Leu Pro Ser Thr Thr Ala Ser Lys Ile Ser Ala Leu Glu Gly
            100                 105                 110

Leu Leu Lys Pro Gln Thr Pro Ser Tyr Asn His His Thr Arg Leu His
            115                 120                 125

Arg Gln Arg Ala Leu Asp Tyr Gly Ser Gln Ser Gly Arg Glu Gly Gln
        130                 135                 140

Gly
145

<210> SEQ ID NO 14
<211> LENGTH: 399
<212> TYPE: PRT
<213> ORGANISM: Artificial Sequence
<220> FEATURE:
<223> OTHER INFORMATION: soluble Toso protein

<400> SEQUENCE: 14

Met Tyr Arg Met Gln Leu Leu Ser Cys Ile Ala Leu Ser Leu Ala Leu
1               5                   10                  15

Val Thr Asn Ser Ile Ser Ala Met Val Arg Ser Gly Met Asn Thr Asp
            20                  25                  30

Arg Gly Lys Thr Gln Lys Val Thr Leu Asn Val His Ser Glu Tyr Glu
            35                  40                  45

Pro Ser Trp Glu Glu Gln Pro Met Pro Glu Thr Pro Lys Trp Phe His
    50                  55                  60

Leu Pro Tyr Leu Phe Gln Met Pro Ala Tyr Ala Ser Ser Ser Lys Phe
65                  70                  75                  80

Val Thr Arg Val Thr Thr Pro Ala Gln Arg Gly Lys Val Pro Pro Val
                85                  90                  95

His His Ser Ser Pro Thr Thr Gln Ile Thr His Arg Pro Arg Val Ser
            100                 105                 110
```

```
Arg Ala Ser Ser Val Ala Gly Asp Lys Pro Arg Thr Phe Leu Pro Ser
            115                 120                 125

Thr Thr Ala Ser Lys Ile Ser Ala Leu Glu Gly Leu Leu Lys Pro Gln
    130                 135                 140

Thr Pro Ser Tyr Asn His His Thr Arg Leu His Arg Gln Arg Ala Leu
145                 150                 155                 160

Asp Tyr Gly Ser Gln Ser Gly Arg Glu Gly Gln Gly Phe His Arg Ser
                165                 170                 175

Val Glu Cys Pro Pro Cys Pro Ala Pro Val Ala Gly Pro Ser Val
            180                 185                 190

Phe Leu Phe Pro Pro Lys Pro Lys Asp Thr Leu Met Ile Ser Arg Thr
        195                 200                 205

Pro Glu Val Thr Cys Val Val Val Asp Val Ser His Glu Asp Pro Glu
    210                 215                 220

Val Lys Phe Asn Trp Tyr Val Asp Gly Val Glu Val His Asn Ala Lys
225                 230                 235                 240

Thr Lys Pro Arg Glu Glu Gln Tyr Asn Ser Thr Tyr Arg Val Val Ser
                245                 250                 255

Val Leu Thr Val Leu His Gln Asp Trp Leu Asn Gly Lys Glu Tyr Lys
            260                 265                 270

Cys Lys Val Ser Asn Lys Gly Leu Pro Ser Ser Ile Glu Lys Thr Ile
        275                 280                 285

Ser Lys Ala Lys Gly Gln Pro Arg Glu Pro Gln Val Tyr Thr Leu Pro
    290                 295                 300

Pro Ser Arg Glu Glu Met Thr Lys Asn Gln Val Ser Leu Thr Cys Leu
305                 310                 315                 320

Val Lys Gly Phe Tyr Pro Ser Asp Ile Ala Val Glu Trp Glu Ser Asn
                325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Lys Leu Thr Val Asp Lys Ser Arg
        355                 360                 365

Trp Gln Gln Gly Asn Val Phe Ser Cys Ser Val Met His Glu Ala Leu
    370                 375                 380

His Asn His Tyr Thr Gln Lys Ser Leu Ser Leu Ser Pro Gly Lys
385                 390                 395

<210> SEQ ID NO 15
<211> LENGTH: 192
<212> TYPE: PRT
<213> ORGANISM: Artificial Sequence
<220> FEATURE:
<223> OTHER INFORMATION: soluble Toso protein

<400> SEQUENCE: 15

Glu Met His Val Arg Ile Tyr Leu Cys Arg Glu Met Ala Gly Ser Gly
1               5                   10                  15

Thr Cys Gly Thr Val Val Ser Thr Thr Asn Phe Ile Lys Ala Glu Tyr
            20                  25                  30

Lys Gly Arg Val Thr Leu Lys Gln Tyr Pro Arg Lys Asn Leu Phe Leu
        35                  40                  45

Val Glu Val Thr Gln Leu Thr Glu Ser Asp Ser Gly Val Tyr Ala Cys
    50                  55                  60

Gly Ala Gly Met Asn Thr Asp Arg Gly Lys Thr Gln Lys Val Thr Leu
65                  70                  75                  80
```

```
Asn Val His Ser Glu Tyr Glu Pro Ser Trp Glu Glu Gln Pro Met Pro
                85                  90                  95

Glu Thr Pro Lys Trp Phe His Leu Pro Tyr Leu Phe Gln Met Pro Ala
           100                 105                 110

Tyr Ala Ser Ser Lys Phe Val Thr Arg Val Thr Thr Pro Ala Gln
       115                 120                 125

Arg Gly Lys Val Pro Pro Val His His Ser Ser Pro Thr Thr Gln Ile
       130                 135                 140

Thr His Arg Pro Arg Val Ser Arg Ala Ser Ser Val Ala Gly Asp Lys
145                 150                 155                 160

Pro Arg Thr Phe Leu Pro Ser Thr Thr Ala Ser Lys Ile Ser Ala Leu
                165                 170                 175

Glu Gly Leu Leu Lys Pro Gln Thr Pro Ser Tyr Asn His His Thr Arg
                180                 185                 190

<210> SEQ ID NO 16
<211> LENGTH: 444
<212> TYPE: PRT
<213> ORGANISM: Artificial Sequence
<220> FEATURE:
<223> OTHER INFORMATION: soluble Toso protein

<400> SEQUENCE: 16

Met Tyr Arg Met Gln Leu Leu Ser Cys Ile Ala Leu Ser Leu Ala Leu
1               5                   10                  15

Val Thr Asn Ser Ile Ser Ala Met Val Arg Ser Glu Met His Val Arg
                20                  25                  30

Ile Tyr Leu Cys Arg Glu Met Ala Gly Ser Gly Thr Cys Gly Thr Val
            35                  40                  45

Val Ser Thr Thr Asn Phe Ile Lys Ala Glu Tyr Lys Gly Arg Val Thr
        50                  55                  60

Leu Lys Gln Tyr Pro Arg Lys Asn Leu Phe Leu Val Glu Val Thr Gln
65                  70                  75                  80

Leu Thr Glu Ser Asp Ser Gly Val Tyr Ala Cys Gly Ala Gly Met Asn
                85                  90                  95

Thr Asp Arg Gly Lys Thr Gln Lys Val Thr Leu Asn Val His Ser Glu
                100                 105                 110

Tyr Glu Pro Ser Trp Glu Glu Gln Pro Met Pro Glu Thr Pro Lys Trp
            115                 120                 125

Phe His Leu Pro Tyr Leu Phe Gln Met Pro Ala Tyr Ala Ser Ser Ser
        130                 135                 140

Lys Phe Val Thr Arg Val Thr Thr Pro Ala Gln Arg Gly Lys Val Pro
145                 150                 155                 160

Pro Val His His Ser Ser Pro Thr Thr Gln Ile Thr His Arg Pro Arg
                165                 170                 175

Val Ser Arg Ala Ser Ser Val Ala Gly Asp Lys Pro Arg Thr Phe Leu
                180                 185                 190

Pro Ser Thr Thr Ala Ser Lys Ile Ser Ala Leu Glu Gly Leu Leu Lys
            195                 200                 205

Pro Gln Thr Pro Ser Tyr Asn His His Thr Arg Arg Ser Val Glu Cys
        210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255
```

-continued

```
Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440
```

<210> SEQ ID NO 17
<211> LENGTH: 215
<212> TYPE: PRT
<213> ORGANISM: Artificial Sequence
<220> FEATURE:
<223> OTHER INFORMATION: soluble Toso protein

<400> SEQUENCE: 17

```
Arg Ile Leu Pro Glu Val Lys Val Glu Gly Glu Leu Gly Gly Ser Val
1               5                   10                  15

Thr Ile Lys Cys Pro Leu Pro Glu Met His Val Arg Ile Tyr Leu Cys
            20                  25                  30

Arg Glu Met Ala Gly Ser Gly Thr Cys Gly Thr Val Val Ser Thr Thr
        35                  40                  45

Asn Phe Ile Lys Ala Glu Tyr Lys Gly Arg Val Thr Leu Lys Gln Tyr
    50                  55                  60

Pro Arg Lys Asn Leu Phe Leu Val Glu Val Thr Gln Leu Thr Glu Ser
65                  70                  75                  80

Asp Ser Gly Val Tyr Ala Cys Gly Ala Gly Met Asn Thr Asp Arg Gly
                85                  90                  95

Lys Thr Gln Lys Val Thr Leu Asn Val His Ser Glu Tyr Glu Pro Ser
            100                 105                 110

Trp Glu Glu Gln Pro Met Pro Glu Thr Pro Lys Trp Phe His Leu Pro
        115                 120                 125

Tyr Leu Phe Gln Met Pro Ala Tyr Ala Ser Ser Lys Phe Val Thr
    130                 135                 140

Arg Val Thr Thr Pro Ala Gln Arg Gly Lys Val Pro Pro Val His His
145                 150                 155                 160

Ser Ser Pro Thr Thr Gln Ile Thr His Arg Pro Arg Val Ser Arg Ala
                165                 170                 175
```

```
Ser Ser Val Ala Gly Asp Lys Pro Arg Thr Phe Leu Pro Ser Thr Thr
            180                 185                 190

Ala Ser Lys Ile Ser Ala Leu Glu Gly Leu Leu Lys Pro Gln Thr Pro
        195                 200                 205

Ser Tyr Asn His His Thr Arg
    210                 215

<210> SEQ ID NO 18
<211> LENGTH: 467
<212> TYPE: PRT
<213> ORGANISM: Artificial Sequence
<220> FEATURE:
<223> OTHER INFORMATION: soluble Toso protein

<400> SEQUENCE: 18

Met Tyr Arg Met Gln Leu Leu Ser Cys Ile Ala Leu Ser Leu Ala Leu
1               5                   10                  15

Val Thr Asn Ser Ile Ser Ala Met Val Arg Ser Arg Ile Leu Pro Glu
            20                  25                  30

Val Lys Val Glu Gly Glu Leu Gly Gly Ser Val Thr Ile Lys Cys Pro
        35                  40                  45

Leu Pro Glu Met His Val Arg Ile Tyr Leu Cys Arg Glu Met Ala Gly
    50                  55                  60

Ser Gly Thr Cys Gly Thr Val Ser Thr Thr Asn Phe Ile Lys Ala
65                  70                  75                  80

Glu Tyr Lys Gly Arg Val Thr Leu Lys Gln Tyr Pro Arg Lys Asn Leu
                85                  90                  95

Phe Leu Val Glu Val Thr Gln Leu Thr Glu Ser Asp Ser Gly Val Tyr
            100                 105                 110

Ala Cys Gly Ala Gly Met Asn Thr Asp Arg Gly Lys Thr Gln Lys Val
        115                 120                 125

Thr Leu Asn Val His Ser Glu Tyr Glu Pro Ser Trp Glu Glu Gln Pro
    130                 135                 140

Met Pro Glu Thr Pro Lys Trp Phe His Leu Pro Tyr Leu Phe Gln Met
145                 150                 155                 160

Pro Ala Tyr Ala Ser Ser Lys Phe Val Thr Arg Val Thr Thr Pro
                165                 170                 175

Ala Gln Arg Gly Lys Val Pro Pro Val His Ser Ser Pro Thr Thr
            180                 185                 190

Gln Ile Thr His Arg Pro Arg Val Ser Arg Ala Ser Ser Val Ala Gly
        195                 200                 205

Asp Lys Pro Arg Thr Phe Leu Pro Ser Thr Thr Ala Ser Lys Ile Ser
    210                 215                 220

Ala Leu Glu Gly Leu Leu Lys Pro Gln Thr Pro Ser Tyr Asn His His
225                 230                 235                 240

Thr Arg Arg Ser Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320
```

```
Arg Val Val Ser Val Leu Thr Val Leu His Gln Asp Trp Leu Asn Gly
            325                 330                 335

Lys Glu Tyr Lys Cys Lys Val Ser Asn Lys Gly Leu Pro Ser Ser Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 19
<211> LENGTH: 155
<212> TYPE: PRT
<213> ORGANISM: Artificial Sequence
<220> FEATURE:
<223> OTHER INFORMATION: soluble Toso protein

<400> SEQUENCE: 19

Arg Ile Leu Pro Glu Val Lys Val Glu Gly Glu Leu Gly Gly Ser Val
1               5                   10                  15

Thr Ile Lys Cys Pro Leu Pro Glu Met His Val Arg Ile Tyr Leu Cys
            20                  25                  30

Arg Glu Met Ala Gly Ser Gly Thr Cys Gly Thr Val Val Ser Thr Thr
        35                  40                  45

Asn Phe Ile Lys Ala Glu Tyr Lys Gly Arg Val Thr Leu Lys Gln Tyr
    50                  55                  60

Pro Arg Lys Asn Leu Phe Leu Val Glu Val Thr Gln Leu Thr Glu Ser
65                  70                  75                  80

Asp Ser Gly Val Tyr Ala Cys Gly Ala Gly Met Asn Thr Asp Arg Gly
                85                  90                  95

Lys Thr Gln Lys Val Thr Leu Asn Val His Ser Glu Tyr Glu Pro Ser
            100                 105                 110

Trp Glu Glu Gln Pro Met Pro Glu Thr Pro Lys Trp Phe His Leu Pro
        115                 120                 125

Tyr Leu Phe Gln Met Pro Ala Tyr Ala Ser Ser Lys Phe Val Thr
    130                 135                 140

Arg Val Thr Thr Pro Ala Gln Arg Gly Lys Val
145                 150                 155

<210> SEQ ID NO 20
<211> LENGTH: 407
<212> TYPE: PRT
<213> ORGANISM: Artificial Sequence
<220> FEATURE:
<223> OTHER INFORMATION: soluble Toso protein
```

<400> SEQUENCE: 20

```
Met Tyr Arg Met Gln Leu Leu Ser Cys Ile Ala Leu Ser Leu Ala Leu
1               5                   10                  15

Val Thr Asn Ser Ile Ser Ala Met Val Arg Ser Arg Ile Leu Pro Glu
            20                  25                  30

Val Lys Val Glu Gly Glu Leu Gly Gly Ser Val Thr Ile Lys Cys Pro
        35                  40                  45

Leu Pro Glu Met His Val Arg Ile Tyr Leu Cys Arg Glu Met Ala Gly
    50                  55                  60

Ser Gly Thr Cys Gly Thr Val Ser Thr Thr Asn Phe Ile Lys Ala
65                  70                  75                  80

Glu Tyr Lys Gly Arg Val Thr Leu Lys Gln Tyr Pro Arg Lys Asn Leu
                85                  90                  95

Phe Leu Val Glu Val Thr Gln Leu Thr Glu Ser Asp Ser Gly Val Tyr
            100                 105                 110

Ala Cys Gly Ala Gly Met Asn Thr Asp Arg Gly Lys Thr Gln Lys Val
        115                 120                 125

Thr Leu Asn Val His Ser Glu Tyr Glu Pro Ser Trp Glu Glu Gln Pro
    130                 135                 140

Met Pro Glu Thr Pro Lys Trp Phe His Leu Pro Tyr Leu Phe Gln Met
145                 150                 155                 160

Pro Ala Tyr Ala Ser Ser Ser Lys Phe Val Thr Arg Val Thr Thr Pro
                165                 170                 175

Ala Gln Arg Gly Lys Val Arg Ser Val Glu Cys Pro Pro Cys Pro Ala
            180                 185                 190

Pro Pro Val Ala Gly Pro Ser Val Phe Leu Phe Pro Pro Lys Pro Lys
        195                 200                 205

Asp Thr Leu Met Ile Ser Arg Thr Pro Glu Val Thr Cys Val Val Val
    210                 215                 220

Asp Val Ser His Glu Asp Pro Glu Val Lys Phe Asn Trp Tyr Val Asp
225                 230                 235                 240

Gly Val Glu Val His Asn Ala Lys Thr Lys Pro Arg Glu Glu Gln Tyr
                245                 250                 255

Asn Ser Thr Tyr Arg Val Val Ser Val Leu Thr Val Leu His Gln Asp
            260                 265                 270

Trp Leu Asn Gly Lys Glu Tyr Lys Cys Lys Val Ser Asn Lys Gly Leu
        275                 280                 285

Pro Ser Ser Ile Glu Lys Thr Ile Ser Lys Ala Lys Gly Gln Pro Arg
    290                 295                 300

Glu Pro Gln Val Tyr Thr Leu Pro Pro Ser Arg Glu Glu Met Thr Lys
305                 310                 315                 320

Asn Gln Val Ser Leu Thr Cys Leu Val Lys Gly Phe Tyr Pro Ser Asp
                325                 330                 335

Ile Ala Val Glu Trp Glu Ser Asn Gly Gln Pro Glu Asn Asn Tyr Lys
            340                 345                 350

Thr Thr Pro Pro Val Leu Asp Ser Asp Gly Ser Phe Phe Leu Tyr Ser
        355                 360                 365

Lys Leu Thr Val Asp Lys Ser Arg Trp Gln Gln Gly Asn Val Phe Ser
    370                 375                 380

Cys Ser Val Met His Glu Ala Leu His Asn His Tyr Thr Gln Lys Ser
385                 390                 395                 400

Leu Ser Leu Ser Pro Gly Lys
                405
```

<210> SEQ ID NO 21
<211> LENGTH: 106
<212> TYPE: PRT
<213> ORGANISM: Artificial Sequence
<220> FEATURE:
<223> OTHER INFORMATION: soluble Toso protein

<400> SEQUENCE: 21

```
Arg Ile Leu Pro Glu Val Lys Val Glu Gly Glu Leu Gly Gly Ser Val
1               5                   10                  15

Thr Ile Lys Cys Pro Leu Pro Glu Met His Val Arg Ile Tyr Leu Cys
            20                  25                  30

Arg Glu Met Ala Gly Ser Gly Thr Cys Gly Thr Val Val Ser Thr Thr
        35                  40                  45

Asn Phe Ile Lys Ala Glu Tyr Lys Gly Arg Val Thr Leu Lys Gln Tyr
    50                  55                  60

Pro Arg Lys Asn Leu Phe Leu Val Glu Val Thr Gln Leu Thr Glu Ser
65                  70                  75                  80

Asp Ser Gly Val Tyr Ala Cys Gly Ala Gly Met Asn Thr Asp Arg Gly
                85                  90                  95

Lys Thr Gln Lys Val Thr Leu Asn Val His
            100                 105
```

<210> SEQ ID NO 22
<211> LENGTH: 358
<212> TYPE: PRT
<213> ORGANISM: Artificial Sequence
<220> FEATURE:
<223> OTHER INFORMATION: soluble Toso protein

<400> SEQUENCE: 22

```
Met Tyr Arg Met Gln Leu Leu Ser Cys Ile Ala Leu Ser Leu Ala Leu
1               5                   10                  15

Val Thr Asn Ser Ile Ser Ala Met Val Arg Ser Arg Ile Leu Pro Glu
            20                  25                  30

Val Lys Val Glu Gly Glu Leu Gly Gly Ser Val Thr Ile Lys Cys Pro
        35                  40                  45

Leu Pro Glu Met His Val Arg Ile Tyr Leu Cys Arg Glu Met Ala Gly
    50                  55                  60

Ser Gly Thr Cys Gly Thr Val Val Ser Thr Thr Asn Phe Ile Lys Ala
65                  70                  75                  80

Glu Tyr Lys Gly Arg Val Thr Leu Lys Gln Tyr Pro Arg Lys Asn Leu
                85                  90                  95

Phe Leu Val Glu Val Thr Gln Leu Thr Glu Ser Asp Ser Gly Val Tyr
            100                 105                 110

Ala Cys Gly Ala Gly Met Asn Thr Asp Arg Gly Lys Thr Gln Lys Val
        115                 120                 125

Thr Leu Asn Val His Arg Ser Val Glu Cys Pro Pro Cys Pro Ala Pro
    130                 135                 140

Pro Val Ala Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205
```

```
Ser Thr Tyr Arg Val Val Ser Val Leu Thr Val Leu His Gln Asp Trp
    210                 215                 220

Leu Asn Gly Lys Glu Tyr Lys Cys Lys Val Ser Asn Lys Gly Leu Pro
225                 230                 235                 240

Ser Ser Ile Glu Lys Thr Ile Ser Lys Ala Lys Gly Gln Pro Arg Glu
                245                 250                 255

Pro Gln Val Tyr Thr Leu Pro Pro Ser Arg Glu Glu Met Thr Lys Asn
            260                 265                 270

Gln Val Ser Leu Thr Cys Leu Val Lys Gly Phe Tyr Pro Ser Asp Ile
            275                 280                 285

Ala Val Glu Trp Glu Ser Asn Gly Gln Pro Glu Asn Asn Tyr Lys Thr
        290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355

<210> SEQ ID NO 23
<211> LENGTH: 94
<212> TYPE: PRT
<213> ORGANISM: Artificial Sequence
<220> FEATURE:
<223> OTHER INFORMATION: soluble Toso protein

<400> SEQUENCE: 23

Arg Ile Leu Pro Glu Val Lys Val Glu Gly Glu Leu Gly Gly Ser Val
1               5                   10                  15

Thr Ile Lys Cys Pro Leu Pro Glu Met His Val Arg Ile Tyr Leu Cys
            20                  25                  30

Arg Glu Met Ala Gly Ser Gly Thr Cys Gly Thr Val Val Ser Thr Thr
        35                  40                  45

Asn Phe Ile Lys Ala Glu Tyr Lys Gly Arg Val Thr Leu Lys Gln Tyr
    50                  55                  60

Pro Arg Lys Asn Leu Phe Leu Val Glu Val Thr Gln Leu Thr Glu Ser
65                  70                  75                  80

Asp Ser Gly Val Tyr Ala Cys Gly Ala Gly Met Asn Thr Asp
                85                  90

<210> SEQ ID NO 24
<211> LENGTH: 346
<212> TYPE: PRT
<213> ORGANISM: Artificial Sequence
<220> FEATURE:
<223> OTHER INFORMATION: soluble Toso protein

<400> SEQUENCE: 24

Met Tyr Arg Met Gln Leu Leu Ser Cys Ile Ala Leu Ser Leu Ala Leu
1               5                   10                  15

Val Thr Asn Ser Ile Ser Ala Met Val Arg Ser Arg Ile Leu Pro Glu
            20                  25                  30

Val Lys Val Glu Gly Glu Leu Gly Gly Ser Val Thr Ile Lys Cys Pro
        35                  40                  45

Leu Pro Glu Met His Val Arg Ile Tyr Leu Cys Arg Glu Met Ala Gly
    50                  55                  60
```

Ser Gly Thr Cys Gly Thr Val Val Ser Thr Thr Asn Phe Ile Lys Ala
 65                  70                  75                  80

Glu Tyr Lys Gly Arg Val Thr Leu Lys Gln Tyr Pro Arg Lys Asn Leu
             85                  90                  95

Phe Leu Val Glu Val Thr Gln Leu Thr Glu Ser Asp Ser Gly Val Tyr
            100                 105                 110

Ala Cys Gly Ala Gly Met Asn Thr Asp Arg Ser Val Glu Cys Pro Pro
        115                 120                 125

Cys Pro Ala Pro Pro Val Gly Pro Ser Val Phe Leu Phe Pro Pro
        130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
                180                 185                 190

Glu Gln Tyr Asn Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
        210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
                245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
        275                 280                 285

Asn Tyr Lys Thr Thr Pro Pro Val Leu Asp Ser Asp Gly Ser Phe Phe
        290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 25
<211> LENGTH: 7
<212> TYPE: PRT
<213> ORGANISM: Artificial Sequence
<220> FEATURE:
<223> OTHER INFORMATION: soluble Toso protein

<400> SEQUENCE: 25

Ile Ser Ala Met Val Arg Ser
1               5

<210> SEQ ID NO 26
<211> LENGTH: 24
<212> TYPE: DNA
<213> ORGANISM: Artificial Sequence
<220> FEATURE:
<223> OTHER INFORMATION: synthetic oligomer

<400> SEQUENCE: 26
gtgaatacgt gagcttgggc tacc                                          24

```
<210> SEQ ID NO 27
<211> LENGTH: 24
<212> TYPE: DNA
<213> ORGANISM: Artificial Sequence
<220> FEATURE:
<223> OTHER INFORMATION: synthetic oligomer

<400> SEQUENCE: 27
caagtgatgg gggattacag tgaa                                          24

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
tgtttaatat gatgtgtcag gctg                                          24

<210> SEQ ID NO 29
<211> LENGTH: 26
<212> TYPE: DNA
<213> ORGANISM: Artificial Sequence
<220> FEATURE:
<223> OTHER INFORMATION: primer

<400> SEQUENCE: 29
agggccagct cattcctccc actcat                                        26

<210> SEQ ID NO 30
<211> LENGTH: 26
<212> TYPE: DNA
<213> ORGANISM: Artificial Sequence
<220> FEATURE:
<223> OTHER INFORMATION: primer

<400> SEQUENCE: 30
aactctgccc ctgctccttc atttcc                                        26
```

METHODS AND COMPOSITIONS FOR MODULATING TOSO ACTIVITY

CROSS REFERENCE TO RELATED APPLICATIONS

The present application is a divisional of U.S. application Ser. No. 14/539,872, filed Nov. 12, 2014, which is a continuation of U.S. application Ser. No. 13/831,031, filed Mar. 14, 2013, which claims the benefit of priority to U.S. Provisional Application No. 61/612,183, filed Mar. 16, 2012, U.S. Provisional Application No. 61/646,143, filed May 11, 2012, and U.S. Provisional Application No. 61/731,428, filed Nov. 29, 2012, the contents of which are expressly incorporated herein by reference in their entirety for all purposes.

BACKGROUND OF THE INVENTION

Toso or Faim3 (Fas Apoptotic inducing molecule 3) is a single membrane spanning cell surface receptor originally characterized through a retroviral overexpression screen in Jurkat cells, a T cell leukemic line, as a mediator of Fas-induced apoptotic cell death (Hitoshi, Y., et al., Toso, a cell surface, specific regulator of Fas-induced apoptosis in T cells. Immunity, 1998. 8(4): p. 461-71). Subsequent studies have suggested that Toso is the elusive receptor for IgM. The expression of Toso also seems to correlate with particularly aggressive forms of Chronic Lymphocytic Leukemia, or CLL.

There is a need for characterization of the in vivo role of Toso in order to identify its use as a therapeutic target and for compositions comprising agents that can bind to Toso and/or modulate its activity.

SUMMARY OF THE INVENTION

Accordingly, the present invention provides methods and compositions for modulating Toso activity and treating diseases and disorders in which Toso is implicated.

In one aspect, the present invention provides a method of treating an autoimmune disorder in a subject, the method including a step of treating the subject with a composition containing a therapeutically effective amount of a soluble Toso protein. In exemplary embodiments, the autoimmune disorder is without limitation rheumatoid arthritis, multiple sclerosis, lupus or Type I diabetes.

In a further aspect, the present invention provides a method of treating Type II diabetes in a subject, the method including a step of treating the subject with a composition comprising a therapeutically effective amount of a soluble Toso protein.

In one aspect, the present invention provides a method of treating asthma in a subject, the method including a step of treating the subject with a composition comprising a therapeutically effective amount of a soluble Toso protein.

In a further aspect, the present invention provides methods of treating diabetes, asthma, multiple sclerosis, or rheumatoid arthritis in a subject by administering a soluble polypeptide having an amino acid sequence of SEQ ID NO: 5 or 6 or a fragment or a deletion variant thereof to that subject. In further embodiments, the Toso activity in the subject is reduced in the subject. In still further embodiments, the present invention provides methods of treating diabetes, asthma, multiple sclerosis, or rheumatoid arthritis in a subject by administering a soluble polypeptide comprising an amino acid sequence of any one or more of SEQ ID NOs. 1-25.

In a further aspect, the present invention provides methods of treating cancer, allergy, COPD, hyper-IgM syndrome, lupus, or a neutrophilia-associated disorder in a subject, the method including a step of treating the subject with a composition comprising a therapeutically effective amount of a soluble Toso protein.

In further embodiments and in accordance with any of the above, the soluble Toso protein of the invention includes amino acid residues amino acids P21 to G251 of NP_005440.1, human Toso isoform a (see Shima et al., Int. Immunol., 2010, which is hereby incorporated in its entirety for all purposes and in particular for all teachings related to the extracellular domain of Toso).

In still further embodiments and in accordance with any of the above, the soluble Toso protein of the invention includes the extracellular domain of a human Toso protein. In further embodiments, the soluble Toso protein of use in the invention includes amino acid residues 18-253 of SEQ ID NO: 7.

In still further embodiments and in accordance with any of the above, the soluble Toso protein used in methods of the present invention comprises an amino acid sequence according to SEQ ID NO: 5 or 6. In yet further embodiments, the soluble Toso protein comprises an amino acid sequence with at least 90% sequence identity to SEQ ID NO: 5 or 6. In yet further embodiments, the soluble Toso protein of the present invention includes deletion variants of SEQ ID NO: 5 or 6. In still further embodiments and in accordance with any of the above, the soluble Toso protein used in methods of the present invention comprises an amino acid sequence of any one or more of SEQ ID NOs. 1-25.

In further embodiments and in accordance with any of the above, the soluble Toso protein of the invention is a multimer. In still further embodiments, the multimer is made up of 6 monomers. In yet further embodiments, each monomer of the multimeric Toso protein comprises a sequence according to SEQ ID NO: 6.

In a further aspect, the present invention provides methods for inhibiting Toso activity that include applying a soluble Toso polypeptide to a cell comprising a membrane-bound Toso receptor.

In a still further aspect, the present invention provides a composition that includes a polypeptide of SEQ ID NO: 5 or SEQ ID NO: 6. In one embodiment, that composition inhibits Toso activity. In a further embodiment, the polypeptide is a multimer. In a still further embodiment, the multimer includes 6 monomers, where each monomer comprises a sequence according to SEQ ID NO: 6.

In a further embodiment, the present invention provides an isolated nucleic acid encoding a soluble Toso protein in accordance with any of the protein described herein. In a still further embodiment, the present invention provides a host cell expressing an isolated nucleic acid encoding a soluble Toso protein in accordance with any of the protein described herein.

In a further aspect, the present invention provides a fusion protein comprising an extracellular domain of a human Toso protein, an Fc region, and a multimerization tag. In a further embodiment, the extracellular domain comprises amino acids 21-251 of a human Toso protein. In a still further embodiment, the multimerization tag comprises SEQ ID NO: 4. In a yet further embodiment, the Fc region comprises SEQ ID NO: 3.

In a further embodiment, the present invention provides an isolated nucleic acid encoding the fusion protein described above. In a still further embodiment, the present invention provides a host cell comprising a nucleic acid encoding the fusion protein described above.

In a further aspect, the present invention provides an isolated, soluble polypeptide comprising an amino acid sequence having at least 90% sequence identity to SEQ ID NOs. 8-24 or to a polypeptide region comprising amino acid residues 18-251 of SEQ ID NO: 7.

In a further aspect, the present invention provides methods for producing a polypeptide encoding any of the soluble Toso proteins described herein, the method including providing a cell comprising a nucleic acid encoding said polypeptide, the cell is cultured under conditions suitable for expression of said polypeptide. In further embodiments, the present invention provides a nucleic acid encoding any of the soluble Toso proteins described herein.

BRIEF DESCRIPTION OF THE DRAWINGS

FIG. 1A shows measures of joint inflammation as measured by the change in ankle thickness using a digital caliper. FIG. 1B shows disease severity scores for each joint based on visible swelling and mobility. FIG. 1C shows flow cytometric analysis of lymphocyte populations in the draining lymph node.

FIG. 2A is a schematic illustration of the induction of the asthma model. FIG. 2B shows data on eosinophil migration into the bronchioalveolar space as assessed by DifQuik staining. FIG. 2C shows data on eosinophils quantified by counting at least 200 leukocytes per slide.

FIGS. 4A and B show total and specific IgE levels in Toso$^{-/-}$ mice, and FIG. 4C shows IgG1 levels between the wildtype and Toso$^{-/-}$ mice.

FIG. 8A is a schematic illustration of the Toso soluble receptor. FIG. 8B shows ELISA data on the soluble receptor. FIG. 8Ci and FIG. 8Cii shows data confirmation of the secretion of the Toso soluble receptor by Western Blot (FIG. 8Ci) and by Coomassie Blue staining (FIG. 8Cii). FIG. 8E-1, FIG. 8E-2, FIG. 8E-3, FIG. 8E-4 and FIG. 8E-5 show further data indicating that Toso-Fc bound most significantly to CD11c+MHChi mature dendritic cells, CD4+ T cells and B220+ B cells in the spleen.

FIG. 10A, FIG. 10B, FIG. 10C and FIG. 10D provide sequences of embodiments of the invention, including that of a soluble Toso protein (FIG. 10A), an IL-2 signal sequence (FIG. 10B), an Fc domain (FIG. 10C) and a hexamerization tag (FIG. 10D).

FIG. 11A provides a sequence of an embodiment of a soluble Toso protein comprising a hexameric tag, allowing for expression of a multimeric form of the soluble receptor. FIG. 11B provides a sequence of a human Toso protein, NP_005440.1 (SEQ ID NO: 7).

FIG. 12A: RNA was isolated from spleens and livers of wildtype (WT) and Toso$^{-/-}$ mice. Toso RNA was analyzed using RT-PCR and expressed as Expression per 18S RNA (n=4). FIG. 12B: Splenocytes from C57BL/6 mice and Toso$^{-/-}$ C mice were stained for CD19 (B cells) and CD3 (T cells) and co-stained with rat anti-mouse Toso antibody or isotype control. Grey areas indicate isotype control, bolded lines indicate staining with anti Toso antibody. One representative histogram of CD19 positive cells (B cells) and CD3 positive cells (T cells) is shown. FIG. 12C: Splenocytes and blood leukocytes from C57BL/6 mice and Toso$^{-/-}$ mice were stained for Gr1 together with rat anti-mouse Toso antibody or isotype control. Grey areas indicate isotype control, bolded lines indicate staining with Toso. One representative histogram of Gr1 positive cells is shown. FIG. 12D: Blood leukocytes from wildtype and Toso$^{-/-}$ mice were analyzed for granulocytes and lymphocytes by forward and side scatter. Leukocytes per μl are shown (n=4). FIG. 12E: Lymphocytes were analyzed for CD4 T cells (CD3$^+$ CD8$^-$ cells) CD8 T cells (CD3$^+$ CD8$^+$ cells) and B cells (B220$^+$ cells, n=4). FIG. 12F: Spleen weight from wildtype and Toso$^{-/-}$ mice were analyzed (n=4).

FIG. 13A: Blood from wildtype or Toso$^{-/-}$ mice was incubated with different concentrations of fMLP for 30 minutes at 37° C. Activation of granulocytes was measured by ROS production (Dihydrorhodamine staining) and degranulation (side-scatter) as described in methods. One representative dot plot of cells gated on granulocytes is shown. Gate is set on activated granulocytes. Percentage of activated granulocytes is given (n=6). FIG. 13B: Blood from WT and Toso$^{-/-}$ mice was incubated with different concentrations of TNF-α. Percentage of activated granulocytes is given (n=6). FIG. 13C: Blood from WT and Toso$^{-/-}$ mice was incubated with different concentrations of lipopolysacharride. Percentage of activated granulocytes is given (n=6). FIG. 13D: Blood from WT and Toso$^{-/-}$ mice was incubated with different concentrations of GM-CSF (given as percent of supernatant form X63O cells). Percentage of activated granulocytes is given (n=6). FIG. 13E: Blood from wildtype and Toso$^{-/-}$ mice was primed with 10% GM-CSF supernatant or 500 ng/ml LPS. After 30 minutes cells were stimulated with 2pM fMLP for 15 minutes. Percentage of activated granulocytes is given (n=6). FIG. 13F: Blood from WT and Toso$^{-/-}$ mice was incubated at different temperatures for 30 minutes. Degranulation was measured using side scatter. Percentage of de-granulated cells is given (n=6).

FIG. 14A: Representative FACS plots of cells gated for Gr1 and stained for CD45.1, CD45.2 and Dihydrorhodamin (ROS) are shown. FIG. 14B: Percentages of granulocytes are quantified for the three different groups of bone marrow chimeras (n=8). FIG. 14C: Percentages of activated granulocytes measured by side scatter and ROS production according to the gate in FIG. 3a was analyzed (n=8). FIG. 14D: The mean fluorescent intensity of side scatter and Dihydrorhodamin (ROS) was analyzed for total and activated granulocytes (n=8).

FIG. 15A: Toso$^{-/-}$ mice and corresponding wildtype mice were infected with 1×10$^4$ CFU of *Listeria*. Survival was monitored (n=8-15). FIG. 15B: Toso$^{-/-}$ mice and corresponding wildtype mice were infected with 1×10$^4$ CFU of *Listeria*. Granulocyte activation (ROS formation) was measured in blood granulocytes d0 and d2 after infection (n=4-5). FIG. 15C: WT and Toso$^{-/-}$ mice were infected with 1×10$^6$ CFU of *Listeria*. Myeloperoxidase was analyzed in plasma of naïve WT mice, and *Listeria* infected WT and Toso$^{-/-}$ mice six hours after infection (n=4). FIG. 15D: Toso$^{-/-}$ mice and corresponding WT mice were infected with 1×10$^6$ CFU of *Listeria monocytogenes*. Liver histology was analyzed 20 hours later. One representative slide is shown (n=4). Scale bar=50 µm. FIG. 15E: Toso$^{-/-}$ mice and corresponding WT mice were infected with 1×10$^4$ CFU of *Listeria*. After one day ROS production was measured in granulocytes of spleen and liver (n=3). FIG. 15F: Toso$^{-/-}$ mice and corresponding WT mice were infected with 1×10$^4$ CFU of *Listeria*. On day 3 and 4 after infection, *Listeria* titers were analyzed in spleen, liver and brain (n=6).

FIG. 16A: Blood granulocytes from Toso$^{-/-}$ mice and corresponding WT mice were formalin fixed and then stained for CD11a, CD11b and CD18. Mean fluorescent expression is shown (n=6). p values are derived from paired students t test. FIG. 16B: Blood from wildtype and Toso$^{-/-}$ mice was stimulated with different concentrations of GM-CSF and LPS. Mean fluorescent expression for CD11b on granulocytes is shown (n=6). FIG. 16C: Blood granulocytes from Cd11b$^{-/-}$ mice and corresponding wildtype mice were stimulated with 2 µM fMLP or with 40% GM-CSF supernatant in addition to 2 µM fMLP. Mean fluorescent intensity is given for CD11b and CD18 (n=4). FIG. 16D: Blood Granulocytes from Cd11b$^{-/-}$ mice and corresponding wildtype mice were stimulated with 2 µM fMLP or with 40% GM-CSF supernatant in addition to 2 µM fMLP. Percentage of activated granulocytes is given (n=4). Mean fluorescent intensity of ROS staining is given for total granulocytes as well as for activated granulocytes (n=4).

FIG. 19A shows body weights of wildtype and Toso$^{-/-}$ male mice, which were monitored since the initiation of a high fat diet starting at 5 weeks of age. FIG. 19B shows measurements of food intake in both sets of mice at 14 weeks post high fat diet.

FIG. 27A, FIG. 27B and FIG. 27C provide sequences of different embodiments of soluble Toso proteins of the invention.

DETAILED DESCRIPTION OF THE INVENTION

Figure 1A:
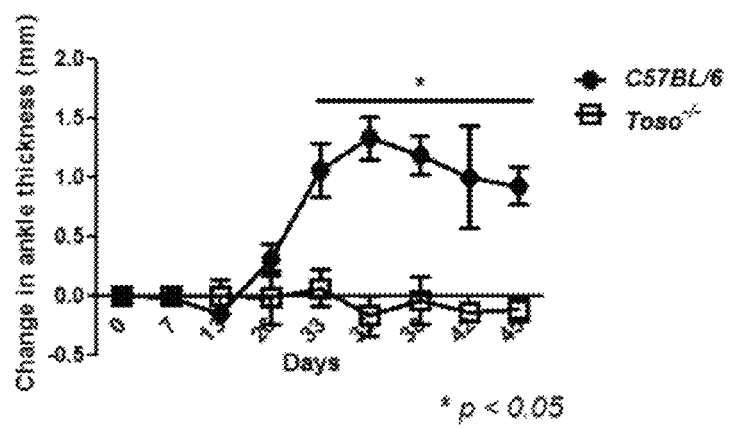
FIG. 1A, FIG. 1B and FIG. 1C show data related to inflammation in Toso$^{-/-}$ mice.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, N.Y., Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, 5th Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

A "composition" may include any substance comprising an agent or compound and is also intended to encompass any combination of an agent or compound and other substances, including a carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term pharmaceutically acceptable carrier (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodible). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

As used herein, the term "patient" or "subject" intends an animal, a mammal or yet further a human patient. For the purpose of illustration only, a mammal includes but is not limited to a human, a simian, a murine, a bovine, an equine, a porcine or an ovine.

As used herein, the term "oligonucleotide" or "polynucleotide" refers to a short polymer composed of deoxyribonucleotides, ribonucleotides or any combination thereof. Oligonucleotides are generally at least about 10, 15, 20, 25, 30, 40, 50, 60, 70, 80, 90, 100 or more nucleotides in length. An oligonucleotide may be used as a primer or as a probe.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

The term "isolated" as used herein refers to molecules or biological or cellular materials being substantially free from other materials, e.g., greater than 70%, or 80%, or 85%, or 90%, or 95%, or 98%. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source and which allow the manipulation of the material to achieve results not achievable where present in its native or natural state, e.g., recombinant replication or manipulation by mutation. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides, e.g., with a purity greater than 70%, or 80%, or 85%, or 90%, or 95%, 98%, or 99%. The term "isolated" is also used herein to refer to cells or tissues that are isolated from other cells or tissues and is meant to encompass both cultured and engineered cells or tissues.

A "recombinant" nucleic acid refers an artificial nucleic acid that is created by combining two or more sequences that would not normally occur together. In one embodiment, it is created through the introduction of relevant DNA into an existing organismal DNA, such as the plasmids of bacteria, to code for or alter different traits for a specific purpose, such as antibiotic resistance. A "recombinant" polypeptide is a polypeptide that is derived from a recombinant nucleic acid.

As used herein, the term "promoter" refers to a nucleic acid sequence sufficient to direct transcription of a gene. Also included in the invention are those promoter elements which are sufficient to render promoter dependent gene expression controllable for cell type specific, tissue specific or inducible by external signals or agents.

In some embodiments, a promoter is an inducible promoter or a discrete promoter. Inducible promoters can be turned on by a chemical or a physical condition such as temperature or light. Examples of chemical promoters include, without limitation, alcohol-regulated, tetracycline-regulated, steroid-regulated, metal-regulated and pathogenesis-related promoters. Examples of discrete promoters can be found in, for examples, Wolfe et al. Molecular Endocrinology 16(3): 435-49.

As used herein, the term "regulatory element" refers to a nucleic acid sequence capable of modulating the transcription of a gene. Non-limiting examples of regulatory element include promoter, enhancer, silencer, poly-adenylation signal, transcription termination sequence. Regulatory element may be present 5' or 3' regions of the native gene, or within an intron.

Various proteins are also disclosed herein with their GenBank Accession Numbers for their human proteins and coding sequences. However, the proteins are not limited to human-derived proteins having the amino acid sequences represented by the disclosed GenBank Accession Nos, but may have an amino acid sequence derived from other animals, particularly, a warm-blooded animal (e.g., rat, guinea pig, mouse, chicken, rabbit, pig, sheep, cow, monkey, etc.).

As used herein, the term "Toso", "FAIM3" or "Fas apoptotic inhibitory molecule 3" refers to a protein having an amino acid sequence substantially identical to any of the representative Toso sequences, including any and all versions of GenBank Accession Nos. NP_001135945 (human isoform b), NP_001180267 (human isoform c), NP_005440 (human isoform a), NP_081252 (mouse) or NP_001014843 (rat). Suitable cDNA encoding Toso are provided at GenBank Accession Nos. NM_001142473, NM_001193338, NM_005449, NM_026976, and NM_001014843.

As used herein, the term "biological activity of Toso" or "Toso activity" refers to any biological activity associated with the full length native Toso protein. In some embodiments, the biological activity of Toso refers to binding to an IgM antibody. In further embodiments, the biological activity of Toso refers to inhibiting CD11 b or CD18 activity. In yet further embodiments, the biological activity of Toso refers to increasing the activation threshold of granulocytes. Activation threshold can be measured by number of activated granulocytes from bone marrow. In further embodiments, the biological activity of Toso includes the activation of dendritic cells and their ability to present antigen to T cells. In further embodiments, the biological activity of Toso includes inhibition of apoptosis or enhancement of TNF signaling. In some embodiments, the Toso biological activity is equivalent to the activity of a protein having an amino acid sequence represented by GenBank Accession No. NP_001135945, NP_001180267, NP_005440, NP_081252 or NP_001014843, including any and all versions of these accession numbers.

As used herein, the term "CD11 b", "ITGAM" or "ITGAM integrin, alpha M (complement component 3 receptor 3 subunit)" refers to a protein having an amino acid sequence substantially identical to the representative CD11 b sequence of GenBank Accession No. NP_000623. A suitable cDNA encoding CD11b is provided at GenBank Accession No. NM_000632.

As used herein, the term "biological activity of CD11b" refers to any biological activity associated with the full length native CD11b protein. In one embodiment, the biological activity of CD11b refers to combining with the beta 2 chain (ITGB2) to form a leukocyte-specific integrin. In suitable embodiments, the CD11b biological activity is equivalent to the activity of a protein having an amino acid sequence represented by GenBank Accession No. NP_000623. Measurement of transcriptional activity can be performed using any known method, such as immunohistochemistry, reporter assay or RT-PCR.

As used herein, the term "CD18", "ITGB2" or "ITGB2 integrin, beta 2 (complement component 3 receptor 3 and 4 subunit)" refers to a protein having an amino acid sequence substantially identical to the representative CD18 sequence of GenBank Accession No. NP_000202. A suitable cDNA encoding CD18 is provided at GenBank Accession No. NM_000211.

As used herein, the term "treating" refers to administering a pharmaceutical composition for the purpose of improving the condition of a patient by reducing, alleviating, reversing, or preventing at least one adverse effect or symptom of a disease or disorder.

As used herein, the term "preventing" refers to identifying a subject (i.e., a patient) having an increased susceptibility to a disease but not yet exhibiting symptoms of the disease, and administering a therapy according to the principles of this disclosure. The preventive therapy is designed to reduce the likelihood that the susceptible subject will later become symptomatic or that the disease will be delay in onset or progress more slowly than it would in the absence of the preventive therapy. A subject may be identified as having an increased likelihood of developing the disease by any appropriate method including, for example, by identifying a family history of the disease or other degenerative brain disorder, or having one or more diagnostic markers indicative of disease or susceptibility to disease.

As used herein, the term "sample" or "test sample" refers to any liquid or solid material containing nucleic acids. In suitable embodiments, a test sample is obtained from a biological source (i.e., a "biological sample"), such as cells in culture or a tissue sample from an animal, most preferably, a human.

As used herein, the term "substantially identical", when referring to a protein or polypeptide, is meant one that has at least 80%, 85%, 90%, 95%, or 99% sequence identity to a reference amino acid sequence. The length of comparison is preferably the full length of the polypeptide or protein, but is generally at least 10, 15, 20, 25, 30, 40, 50, 60, 80, or 100 or more contiguous amino acids. A "substantially identical" nucleic acid is one that has at least 80%, 85%, 90%, 95%, 96%, 97%, 98% or 99% sequence identity to a reference nucleic acid sequence. The length of comparison is preferably the full length of the nucleic acid, but is generally at least 20 nucleotides, 30 nucleotides, 40 nucleotides, 50 nucleotides, 75 nucleotides, 100 nucleotides, 125 nucleotides, or more.

As used herein, an "amino acid substitution" or "substitution" refers to the replacement of an amino acid at a particular position in a starting polypeptide sequence with another amino acid. For example, the substitution M23Y refers to a variant polypeptide in which the methionine at position 23 is replaced with a tyrosine.

A "biological equivalent" of a protein or nucleic acid refers to a protein or nucleic acid that is substantially identical to the protein or nucleic acid by amino acid or nucleic acid sequence or that has an equivalent biological activity.

As used herein, the term "effective amount" refers to a quantity of compound (e.g., a Toso protein or biologically active fragment thereof) delivered with sufficient frequency to provide a medical benefit to the patient. In one embodiment, an effective amount of a protein is an amount sufficient to treat or ameliorate a symptom of a disease.

A population of cells intends a collection of more than one cell that is identical (clonal) or non-identical in phenotype and/or genotype.

"Substantially homogeneous" describes a population of cells in which more than about 50%, or alternatively more than about 60%, or alternatively more than 70%, or alternatively more than 75%, or alternatively more than 80%, or alternatively more than 85%, or alternatively more than 90%, or alternatively, more than 95%, of the cells are of the same or similar phenotype. Phenotype can be determined by a pre-selected cell surface marker or other marker.

The terms autologous transfer, autologous transplantation, autograft and the like refer to treatments wherein the cell donor is also the recipient of the cell replacement therapy. The terms allogeneic transfer, allogeneic transplantation, allograft and the like refer to treatments wherein the cell donor is of the same species as the recipient of the cell replacement therapy, but is not the same individual. A cell transfer in which the donor's cells and have been histocompatibly matched with a recipient is sometimes referred to as a syngeneic transfer. The terms xenogeneic transfer, xenogeneic transplantation, xenograft and the like refer to treatments wherein the cell donor is of a different species than the recipient of the cell replacement therapy.

As used herein, an "antibody" includes whole antibodies and any antigen binding fragment or a single chain thereof. Thus the term "antibody" includes any protein or peptide containing molecule that comprises at least a portion of an immunoglobulin molecule. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein. In general, the term "antibody" includes any polypeptide that includes at least one constant domain, including, but not limited to, CH1, CH2, CH3 and CL. Antibodies that find use in the present invention can take on a number of formats as described herein, including traditional antibodies as well as antibody derivatives, fragments and mimetics.

The antibodies can be polyclonal or monoclonal and can be isolated from any suitable biological source, e.g., murine, rat, sheep and canine.

A monoclonal antibody is an antibody produced by a single clone of cells or a hybridoma, and therefore is a single pure homogeneous type of antibody.

A hybridoma is a cell that is produced in the laboratory from the fusion of an antibody-producing lymphocyte and a non-antibody producing cancer cell, usually a myeloma or lymphoma. A hybridoma proliferates and produces a continuous supply of a specific monoclonal antibody.

The term "human antibody" as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are described herein.

"Isotype" as used herein is meant any of the subclasses of immunoglobulins defined by the chemical and antigenic characteristics of their constant regions. It should be understood that therapeutic antibodies can also comprise hybrids of isotypes and/or subclasses.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

The terms "monoclonal antibody" or "monoclonal antibody composition" as used herein refer to a preparation of antibody molecules of single molecular composition. A monoclonal antibody composition displays a single binding specificity and affinity for a particular epitope.

As used herein, the term "label" intends a directly or indirectly detectable compound or composition that is conjugated directly or indirectly to the composition to be detected, e.g., N-terminal histidine tags (N-His), magnetically active isotopes, e.g., $^{115}Sn$, $^{117}Sn$ and $^{119}Sn$, a non-radioactive isotopes such as $^{13}C$ and $^{15}N$, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals (6th ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals (6th ed.).

In another aspect, the fluorescent label is functionalized to facilitate covalent attachment to a cellular component present in or on the surface of the cell or tissue such as a cell surface marker. Suitable functional groups, including, but not are limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

Although the present invention is described primarily with reference to specific embodiments, it is also envisioned that other embodiments will become apparent to those skilled in the art upon reading the present disclosure, and it is intended that such embodiments be contained within the present inventive methods.

I. Overview of the Invention

The present invention is directed to methods and compositions for modulating the activity of the Toso protein (which is also interchangeably referred to herein as "Toso" or "Toso receptor" or "Faim3" or "FCMR"). In some embodiments, the methods and compositions of the invention increase activity of the Toso protein. In other embodiments, the methods and compositions of the invention inhibit activity of the Toso protein. In some embodiments, compositions for modulating the activity of the Toso protein include agents that bind to the Toso protein or to a ligand of the Toso protein. In further embodiments, the compositions of the invention include a soluble Toso protein. As will be discussed in further detail herein, soluble Toso proteins of the invention include all or part of the extracellular domain of a Toso receptor. Soluble Toso proteins of the invention may further include a signal peptide and/or an Fc domain. Soluble Toso proteins of the invention may further include variant extracellular domains of a Toso protein, including deletion variants (variants in which one or more amino acids of the full extracellular domain are deleted) and variants comprising one or more amino acid substitutions.

The present invention is further directed to methods of treating disorders and diseases by administering a soluble Toso protein (or a variant thereof) to a subject. As will be discussed in further detail herein, soluble Toso proteins of the invention can be used to treat subjects suffering from without limitation an autoimmune disorder (including without limitation Type 1 or Type 2 diabetes, multiple sclerosis, or rheumatoid arthritis), asthma, allergy, chronic obstructive pulmonary disease ("COPD"), hyper-IgM syndrome, CLL, lupus, or a neutrophilia-associated disorder (including without limitation neutropenia, severe congenital neutropenia, cyclical neutropenia, antibody mediated neutropenia, reticular dysgenesis, leukocyte adhesion deficiency, familiar myeloproliferative disease, chronic myelogenous leukemia, familiar cold urticaria and leukocytosis, and chronic granulomatous disease).

II. Soluble Toso Protein

Compositions of the invention include agents that modulate Toso activity. Such compositions, as will be discussed in further detail below, include without limitation a soluble form of the Toso protein.

A soluble Toso protein of the invention (also referred to interchangeably herein as the "soluble Toso receptor," "Toso-Fc", and "soluble Toso polypeptide") includes all or part of an extracellular domain of a Toso receptor. The soluble Toso proteins of the invention in further embodiments include a signal domain and/or an Fc domain. As will be discussed in further detail herein, these components of the soluble Toso protein may be combined in any way with or without additional components and/or modifications to provide a soluble Toso protein of the invention.

In one aspect, the soluble Toso protein of the invention comprises an extracellular domain of Toso. In a still further embodiments, the soluble Toso protein comprises the extracellular domain of human Toso isoform a. The extracellular domain of human Toso is predicted to span amino acids P21 to G251 of NP_005440.1, human Toso isoform a (see Shima et al., Int. Immunol., 2010, which is hereby incorporated in its entirety for all purposes and in particular for all teachings related to the extracellular domain of Toso). For the sake of clarity, the majority of the discussion herein is directed to soluble Toso proteins comprising all or part of an extracellular domain of a human Toso protein. However, it will be appreciated that the extracellular domain of a Toso protein from any species can be used to produce soluble Toso proteins in accordance with the description herein, and it would be well within the ability of one of skill in the art to identify the regions of the Toso protein from another species that correspond to the regions of the human Toso protein discussed herein.

In one embodiment, the soluble Toso protein comprises an extracellular domain sequence according to SEQ ID NO: 1, which is shown in FIG. 10. In a further embodiment, the soluble Toso protein has a sequence identity of about 70%, 75%, 80%, 85%, 90%, 91%, 92%, 93%, 94%, 95%, 96%, 97%, 98%, 99% and 100% identity to SEQ ID NO: 1. In a still further embodiment, the soluble Toso protein comprises a polypeptide with 1-75, 2-70, 3-65, 4-60, 5-55, 6-50, 7-45, 8-40, 9-35, 10-30, 11-25, 12-20, 13-15, 5-20, 6-18, 8-16, 10-14 amino acid substitutions in SEQ ID NO: 1. In a yet further embodiments, the soluble Toso protein comprises a polypeptide with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 amino acid substitutions in SEQ ID NO: 1.

In one embodiment, the soluble Toso protein comprises an extracellular domain sequence according to SEQ ID NO: 8, which is shown in FIG. 27. In a further embodiment, the soluble Toso protein has a sequence identity of about 70%, 75%, 80%, 85%, 90%, 91%, 92%, 93%, 94%, 95%, 96%, 97%, 98%, 99% and 100% identity to SEQ ID NO: 8. In a still further embodiment, the soluble Toso protein comprises a polypeptide with 1-75, 2-70, 3-65, 4-60, 5-55, 6-50, 7-45, 8-40, 9-35, 10-30, 11-25, 12-20, 13-15, 5-20, 6-18, 8-16, 10-14 amino acid substitutions in SEQ ID NO: 8. In a yet further embodiments, the soluble Toso protein comprises a polypeptide with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 amino acid substitutions in SEQ ID NO: 8.

In a further embodiment and in accordance with any of the above, the soluble Toso protein of the invention includes amino acids 18 to 253 of SEQ ID NO: 7. In a still further embodiment, the soluble Toso protein of the invention includes amino acids 21 to 253 of SEQ ID NO: 7. In a still further embodiment, the soluble Toso protein includes amino acids 21 to 251 of SEQ ID NO: 7. In a yet further embodiment, the soluble Toso protein includes any of the following ranges of amino acids from SEQ ID NO: 7: 1-255, 5-245, 10-235, 15-225, 20-215, 25-205, 30-195, 35-185, 40-175, 45-165, 50-155, 45-145, 40-135, 35-125, 30-115, 35-105, 40-95, 45-85, 50-75, 55-65. In a still further embodiment, the soluble Toso protein includes a sequence with a sequence identity of about 70%, 75%, 80%, 85%, 90%, 91%, 92%, 93%, 94%, 95%, 96%, 97%, 98%, 99% and 100% identity to amino acids 18 to 253 or 21 to 253 of SEQ ID NO: 7.

In a still further embodiment and in accordance with any of the above, the soluble Toso protein of the invention includes all or a portion of SEQ ID NO: 8, pictured in FIG. 27. In still further embodiments, the soluble Toso protein includes amino acids 1-231, 6-221, 11-211, 16-201, 21-191, 26-181, 31-171, 36-161, 41-151, 46-141, 51-131, 56-121, 61-111, 66-101, 71-91, 76-81 of SEQ ID NO: 8. In yet further embodiments, the soluble Toso protein includes a polypeptide with at least 70%, 75%, 80%, 85%, 90%, 91%, 92%, 93%, 94%, 95%, 96%, 97%, 98%, 99% and 100% sequence identity to the amino acid regions 1-231, 6-221, 11-211, 16-201, 21-191, 26-181, 31-171, 36-161, 41-151, 46-141, 51-131, 56-121, 61-111, 66-101, 71-91, 76-81 of SEQ ID NO: 8.

In a yet further embodiment, the soluble Toso protein of the invention comprises any one of SEQ ID NOs: 8, 9, 11, 13, 15, 17, 19, 21, and 23. In a still further embodiment, the soluble Toso protein includes a sequence with a sequence identity of about 70%, 75%, 80%, 85%, 90%, 91%, 92%, 93%, 94%, 95%, 96%, 97%, 98%, 99% and 100% identity to SEQ ID NOs: 8, 9, 11, 13, 15, 17, 19, 21, and 23. These sequences include deletion variants of the extracellular domain of the Toso receptor.

In still further embodiments and in accordance with any of the above, the soluble Toso protein of the invention comprises a deletion variant of the full extracellular domain of the Toso protein. In exemplary embodiments, the deletion variants that are a component of a soluble Toso protein of the invention include a polypeptide in which one or more of the following amino acids have been deleted from SEQ ID NO:8: 1-21, 1-35, 1-87, both regions 1-21 and 211-231, 211-231, 154-231, 105-231, and 93-231. In further exemplary embodiments, the deletion variants that are a component of a soluble Toso protein of the invention include a polypeptide with a sequence identity of about 70%, 75%, 80%, 85%, 90%, 91%, 92%, 93%, 94%, 95%, 96%, 97%, 98%, 99% to a polypeptide according to SEQ ID NO:8 with one or more of the following amino acid regions deleted: 1-21, 1-35, 1-87, both regions 1-21 and 211-231, 211-231, 154-231, 105-231, and 93-231.

In further embodiments and in accordance with any of the above, the soluble Toso protein of the invention includes an extracellular domain component that comprises regions that bind to a ligand of the Toso receptor. In an exemplary embodiment, the soluble Toso protein of the invention includes an extracellular domain component that binds to IgM. In a still further embodiment, the soluble Toso protein of the invention includes amino acids 35 to 87 of SEQ ID NO: 8. In further exemplary embodiments, the soluble Toso protein of the invention includes amino acids 25-100, 29-95, 33-90, 37-85, 41-80, 45-75, 49-70, 53-65, or 57-60 of SEQ ID NO: 8.

In a further aspect and in accordance with any of the above, the soluble Toso protein of the invention includes an extracellular domain component as is discussed above and further includes a signal sequence. In an exemplary embodiment, the signal sequence enhances secretion from host cells. In a yet further embodiment, the signal sequence includes without limitation a member selected from an IL-2 signal sequence, α-mating factor pre-sequence from *Saccharomyces cerevisiae*, α-amylase signal sequence from *Aspergillus niger*, Glucoamylase signal sequence from *Aspergillus awamori*, Serum albumin signal sequence from *Homo sapiens*, Inulinase signal sequence from *Kluyveromyces maxianus*, Invertase signal sequence from *Saccharomyces cerevisiae*, Killer protein signal sequence from *Saccharomyces cerevisiae*, Lysozyme signal sequence from *Gallus gallus*. In a still further embodiment, the signal sequence comprises a sequence according to SEQ ID NO: 2, which is shown in FIG. 10. In a still further embodiment, the signal sequence comprises a sequence with a sequence identity of about 70%, 75%, 80%, 85%, 90%, 91%, 92%, 93%, 94%, 95%, 96%, 97%, 98%, 99% and 100% identity to SEQ ID NO: 2. In specific embodiments, the soluble Toso protein of the invention comprises any one of SEQ ID NOs: 1, 8, 9, 11, 13, 15, 17, 21 and 23 or variants of those sequences as a fusion protein with SEQ ID NO: 2 or with a sequence with an identity of about 70%, 75%, 80%, 85%, 90%, 91%, 92%, 93%, 94%, 95%, 96%, 97%, 98%, 99% and 100% identity to SEQ ID NO: 2.

In a further aspect and in accordance with any of the above, a soluble Toso protein of the invention comprises an extracellular domain of a Toso receptor and an Fc domain. In an exemplary embodiment, the soluble Toso protein is a fusion protein comprising the extracellular domain of isoform A of the human Toso protein and an Fc domain. In a further embodiment, the Fc domain includes any domain that enhances the half-life of the protein as compared to the protein without the Fc domain. In a still further embodiment, the Fc domain includes any domain that improves the pharmacokinetic profile of the protein as compared to the protein without the Fc domain. In a still further embodiment, the Fe domain is derived from human IgG1 at the C-terminus, which in a yet further embodiment includes mutations that diminish or ablate antibody-dependent and complement dependent cytotoxicity. In a still further embodiment, such mutations include one or more of the following mutations singly or in any combination: E233P; L234V; L235A; ΔG236; A327G; A330S; P331S. In a yet further embodiment, the Fc domain comprises a sequence according to SEQ ID NO: 3, which is shown in FIG. 10. In a still further embodiment, the Fc domain comprises a sequence with a sequence identity of about 70%, 75%, 80%, 85%, 90%, 91%, 92%, 93%, 94%, 95%, 96%, 97%, 98%, 99% and 100% identity to SEQ ID NO: 3.

In further exemplary embodiments, the soluble Toso protein of the invention comprises a fusion protein comprising both an extracellular domain component and an Fc domain component. In still further exemplary embodiments, the soluble Toso protein of the invention comprises SEQ ID NOs: 1, 8, 9, 11, 13, 15, 17, 21 and 23 or variants of those sequences as a fusion protein with SEQ ID NO: 3 or with a sequence with an identity of about 70%, 75%, 80%, 85%, 90%, 91%, 92%, 93%, 94%, 95%, 96%, 97%, 98%, 99% and 100% identity to SEQ ID NO: 3.

In one aspect and in accordance with any of the above, the soluble Toso protein of the invention comprises an extracellular Toso domain, a signal sequence and an Fe domain—each of those components may comprise any of the above described versions of these components in any combination. In a still further embodiment, the soluble Toso protein of the invention comprises a sequence according to SEQ ID NO: 5, which is shown in FIG. 8. In a still further embodiment, the soluble Toso protein of the invention comprises a sequence with a sequence identity of about 70%, 75%, 80%, 85%, 90%, 91%, 92%, 93%, 94%, 95%, 96%, 97%, 98%, 99% and 100% identity to SEQ ID NO: 5.

In further embodiments and in accordance with any of the above, the soluble Toso protein of the invention comprises a sequence according to any one of SEQ ID NOs. 10, 12, 14, 16, 18, 20, 22 and 24, which comprise an extracellular domain component, a signal sequence, and an Fc domain. In further embodiments, the soluble Toso protein of the invention comprises a sequence with a sequence identity of about 70%, 75%, 80%, 85%, 90%, 91%, 92%, 93%, 94%, 95%, 96%, 97%, 98%, 99% and 100% to any one of SEQ ID NOs. 10, 12, 14, 16, 18, 20, 22 and 24.

In further aspects and in accordance with any of the above, a soluble Toso protein of the invention may further include a linker between the Toso extracellular domain component and the Fc domain, between the Toso extracellular domain component and the signal sequence, or between both the Toso extracellular domain component and the Fc domain and the Toso extracellular domain component and the signal sequence. In exemplary embodiments, such a linker may be an amino acid linker, a polymeric linker, or any other linker known in the art to be effective for joining two amino acid sequences together. In further exemplary embodiments, the linker is an amino acid linker. In still further embodiments, the linker is the amino acid sequence: ISAMVRS (SEQ ID NO: 25). In yet further embodiments, the linker is a variant of SEQ ID NO: 25 containing 1, 2, 3, 4, 5, or 6 amino acid substitutions.

In further embodiments and in accordance with any of the above, variants of the soluble Toso proteins of the invention can be made through modification of the amino acid sequences of any of the soluble Toso proteins discussed herein, including SEQ ID NOs. 5, 6, or 8-24. Such modifications can be achieved using any known technique in the art e.g., site-directed mutagenesis or PCR based mutagenesis. Such techniques are described for example in Sambrook et al., Molecular Cloning: A Laboratory Manual, Cold Spring Harbor Press, Plainview, N.Y., 1989 and Ausubel et al., Current Protocols in Molecular Biology, John Wiley & Sons, New York, N.Y., 1989, each of which is incorporated by reference in its entirety for all purposes and in particular for all teachings related to forming protein variants.

In still further embodiments and in accordance with any of the above, soluble Toso proteins of the invention may be in monomeric or multimeric forms, wherein each monomer of the multimer comprises a single extracellular domain sequence. In further embodiments, the soluble Toso proteins of the invention are in multimers of 2, 3, 4, 5, 6, 7, 8, 9, 10 or more monomers. In a specific embodiment, soluble Toso proteins are multimers of 6 monomers. In a further embodiment, a hexameric Toso multimer is formed of monomers comprising a hexamerization tag. In a further embodiment, the hexamerization tag comprises a 21 amino acid tail piece from human IgA alpha heavy chain constant region as described in Hirano et al., Blood (2006), which is hereby incorporated by reference for all purposes and in particular for all teachings related to hexamerization or other multimerization tags. In yet a further embodiment, the hexamerization tag of the invention includes a sequence according to SEQ ID NO: 4, shown in FIG. 10.

In further embodiments and in accordance with any of the above, the soluble Toso protein of the invention is modified to alter one or more functional properties of the protein. In exemplary embodiments, the soluble Toso protein is chemically modified. For example, the soluble Toso protein may be modified with one or more polymers to improve its stability in vivo and/or alter its pharmacokinetic profile. Such polymers include without limitation one or more of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337, which are all hereby incorporated by reference in their entirety for all purposes and in particular for all teachings related to linking proteins to polymers.

Modifications of the Toso soluble protein included within the scope of this invention include reacting targeted amino acid residues of a Toso polypeptide in accordance with any of the sequences and soluble Toso proteins discussed above with an organic derivatizing agent that is capable of reacting with selected side chains or the N- or C-terminal residues of a Toso polypeptide. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutarnyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, Proteins; Structure and Molecular Properties, W. H. Freeman & Co., San Francisco, pp. 79-86 (1983)], acetylation of the N-terminal amine, and amidation of any C-terminal carboxyl group.

Another type of modification of the soluble Toso protein included within the scope of this invention comprises altering the native glycosylation pattern of the polypeptide. "Altering the native glycosylation pattern" is intended for purposes herein to mean deleting one or more carbohydrate moieties found in native sequence Toso polypeptide, and/or adding one or more glycosylation sites that are not present in the native sequence Toso polypeptide.

Addition of glycosylation sites to Toso soluble protein may be accomplished by altering the amino acid sequence thereof. The alteration may be made, for example, by the addition of, or substitution by, one or more serine or threonine residues to the native sequence the soluble Toso protein (for O-linked glycosylation sites). The soluble Toso protein amino acid sequence may optionally be altered through changes at the DNA level, particularly by mutating the DNA encoding the Toso soluble protein at preselected bases such that codons are generated that will translate into the desired amino acids.

Another means of increasing the number of carbohydrate moieties on the Toso soluble protein is by chemical or enzymatic coupling of glycosides to the polypeptide. Such methods are described in the art, e.g., in WO 87/05330 published Sep. 11, 1987, and in Aplin and Wriston, CRC Crit. Rev. Biochem., pp. 259-306 (1981), which are hereby incorporated by reference in their entirety for all purposes and in particular for all teachings related to altering carbohydrate moieties on a protein.

Removal of carbohydrate moieties present on the soluble Toso protein may be accomplished chemically or enzymatically or by mutational substitution of codons encoding for amino acid residues that serve as targets for glycosylation.

Chemical deglycosylation techniques are known in the art and described, for instance, by Hakimuddin, et al., Arch. Biochem. Biophys., 259:52 (1987) and by Edge, et al., Anal. Biochem., 118:131 (1981). Enzymatic cleavage of carbohydrate moieties on polypeptides can be achieved by the use of a variety of endo- and exo-glycosidases as described by Thotakura, et al., Meth. Enzymol., 138:350 (1987), which are hereby incorporated by reference in their entirety for all purposes and in particular for all teachings related to altering carbohydrate moieties on a protein.

The soluble Toso protein of the present invention may also be modified in a way to form chimeric molecules comprising the protein fused to another, heterologous polypeptide or amino acid sequence. In one embodiment, such a chimeric molecule comprises a fusion of a soluble Toso polypeptide with a tag polypeptide which provides an epitope to which an anti-tag antibody can selectively bind. The epitope tag is generally placed at the amino- or carboxyl-terminus of the Toso polypeptide. The presence of such epitope-tagged forms of a Toso polypeptide can be detected using an antibody against the tag polypeptide. Also, provision of the epitope tag enables the Toso polypeptide to be readily purified by affinity purification using an anti-tag antibody or another type of affinity matrix that binds to the epitope tag. In an alternative embodiment, the chimeric molecule may comprise a fusion of a Toso polypeptide with an immunoglobulin or a particular region of an immunoglobulin. For a bivalent form of the chimeric molecule, such a fusion could be to the Fc region of an IgG molecule or GST fusions.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field, et al., Mol. Cell Biol., 8:2159-2165 (1988)]; the c-myc tag and the 8F9, 3C7, 6E10, G4, B7, and 9E10 antibodies thereto [Evan, et al., Molecular and Cellular Biology, 5:3610-3616 (1985)]; and the Herpes Simplex virus glycoprotein D (gD) tag and its antibody [Paborsky, et al., Protein Engineering, 3(6):547-553 (1990)]. Other tag polypeptides include the Flag-peptide [Hopp, et al., BioTechnology, 6:1204-1210 (1988)]; the KT3 epitope peptide [Martin, et al., Science, 255:192-194 (1992)]; tubulin epitope peptide [Skinner, et al., J. Biol. Chem., 266:15163-15166 (1991)]; and the T7 gene 10 protein peptide tag [Lutz-Freyermuth, et al., Proc. Natl. Acad. Sci. USA, 87; 6393-6397 (1990)].

In further embodiments and in accordance with any of the above, a soluble Toso protein of the invention is fused with a cell penetrating peptide.

In further aspects, the present invention encompasses nucleic acids encoding one or more soluble Toso proteins as well as host cells comprising such nucleic acids. In certain embodiments, host cells used in accordance with the present invention include without limitation HEK293F, HEK298T, Cos7, HeLa, and CHO-DHFR deficient cells. In still further embodiments, soluble Toso proteins of the invention are stably expressed in a cell line that has been modified to grow in a serum-free suspension.

In further aspects, compositions of the invention may include any of the soluble Toso proteins discussed herein along with additives and pharmaceutically acceptable carriers. As used herein, "pharmaceutically acceptable carrier" includes any material, which when combined with the conjugate retains the conjugates' activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

III. Antibodies to Toso

In one aspect, the present invention provides an antibody that binds to the Toso protein. In some embodiments, antibodies of the invention increase Toso activity. In other embodiments, antibodies of the invention decrease Toso activity.

Methods of preparing antibodies are generally known in the art. For example, U.S. Pat. No. 6,727,350 discloses an antibody directed to Toso, which is hereby incorporated by reference in its entirety for all purposes and in particular for all teachings related to antibodies directed to the Toso protein.

An antibody of the invention may be a polyclonal antibody, monoclonal antibody, chimeric antibody, humanized antibody or a derivative or fragment thereof as defined below. In one aspect, a fragment comprises, or alternatively consists essentially of, or yet further consists of the CDR of an antibody. In one aspect, an antibody of the invention is detectably labeled or further comprises a detectable label conjugated to it. Also provided is a hybridoma cell line that produces a monoclonal antibody of this invention. Compositions comprising one or more of the above embodiments are further provided herein.

Also provided is a composition comprising the antibody and a carrier. Further provided is a biologically active fragment of the antibody, or a composition comprising the antibody fragment. Suitable carriers are defined supra.

Further provided is an antibody-peptide complex comprising, or alternatively consisting essentially of, or yet alternatively consisting of, the antibody and a polypeptide specifically bound to the antibody. In one aspect, the polypeptide is the chimeric polypeptide against which the antibody is raised.

This invention also provides an antibody capable of specifically forming a complex with Toso, which are useful in the therapeutic methods of this invention. Antibodies of the invention include, but are not limited to mouse, rat, and rabbit or human antibodies. Antibodies can be produced in cell culture, in phage, or in various animals, including but not limited to cows, rabbits, goats, mice, rats, hamsters, guinea pigs, sheep, dogs, cats, monkeys, chimpanzees, apes, etc. The antibodies are also useful to identify and purify therapeutic polypeptides.

This invention also provides an antibody-peptide complex comprising, or alternatively consisting essentially of, or yet alternatively consisting of, antibodies described above and a polypeptide specifically bound to the antibody. In one aspect the polypeptide is the polypeptide against which the antibody was raised. In one aspect the antibody-peptide complex is an isolated complex. In a further aspect, the antibody of the complex is, but not limited to, a polyclonal antibody, a monoclonal antibody, a humanized antibody or an antibody derivative described herein. Either or both of the antibody or peptide of the antibody-peptide complex can be detectably labeled or further comprises a detectable label conjugated to it. In one aspect, the antibody-peptide complex of the invention can be used as a control or reference sample in diagnostic or screening assays.

Polyclonal antibodies of the invention can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, llamas, mice, rats, and rabbits. An antigen is injected into the mammal, which induces the B-lymphocytes to produce IgG immunoglobulins specific for the antigen. This IgG is purified from the mammal's serum. Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a slow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods described in U.S. Pat. Nos. 7,279,559; 7,119,179; 7,060,800; 6,709,659; 6,656,746; 6,322,788; 5,686,073; and 5,670,153, which are hereby incorporated by reference in their entirety for all purposes and in particular for all teachings related to antibodies.

The monoclonal antibodies of the invention can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U397, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O) or the like, or heteromyelomas, fusion products thereof, or any cell or fusion cell derived therefrom, or any other suitable cell line as known in the art (see, e.g., www.atcc.org, www.lifetech.com., last accessed on Nov. 26, 2007, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, preferably the spleen or lymph nodes, of humans or other suitable animals that have been immunized with the antigen of interest. Any other suitable host cell can also be used for expressing-heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods.

In one embodiment, the antibodies described herein can be generated using a Multiple Antigenic Peptide (MAP) system. The MAP system utilizes a peptidyl core of three or seven radially branched lysine residues, on to which the antigen peptides of interest can be built using standard solid-phase chemistry. The lysine core yields the MAP bearing about 4 to 8 copies of the peptide epitope depending on the inner core that generally accounts for less than 10% of total molecular weight. The MAP system does not require a carrier protein for conjugation. The high molar ratio and dense packing of multiple copies of the antigenic epitope in a MAP has been shown to produce strong immunogenic response. This method is described in U.S. Pat. No. 5,229,490 and is herein incorporated by reference in its entirety for all purposes and in particular for all teachings related to the MAP system.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from various commercial vendors such as Cambridge Antibody Technologies (Cambridgeshire, UK), MorphoSys (Martinsreid/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862, which are hereby incorporated by reference in their entirety for all purposes and in particular for all teachings related to methods related to antibodies. Alternative methods rely upon immunization of transgenic animals (e.g., SCID mice, Nguyen et al. (1997) Microbiol. Immunol. 41:901-907; Sandhu et al. (1996) Crit. Rev. Biotechnol. 16:95-118; Eren et al. (1998) Immunol. 93:154-161 that are capable of producing a repertoire of human antibodies, as known in the art and/or as described herein. Such techniques, include, but are not limited to, ribosome display (Hanes et al. (1997) Proc. Natl. Acad. Sci. USA 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134, which are hereby incorporated by reference in their entirety for all purposes and in particular for all teachings related to methods for generating antibodies.

Antibody derivatives of the present invention can also be prepared by delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873, 316; 5,849,992; 5,994,616; 5,565,362; and 5,304,489, which are hereby incorporated by reference in their entirety for all purposes and in particular for all teachings related to generating antibodies.

The term "antibody derivative" includes post-translational modification to linear polypeptide sequence of the antibody or fragment. For example, U.S. Pat. No. 6,602,684 BI, which is hereby incorporated by reference in its entirety for all purposes and in particular for all teachings related to modifications of antibodies, describes a method for the generation of modified glycol-forms of antibodies, including whole antibody molecules, antibody fragments, or fusion proteins that include a region equivalent to the Fc region of an immunoglobulin, having enhanced Fc-mediated cellular toxicity, and glycoproteins so generated.

Antibody derivatives also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids.

In general, the CDR residues (an example of an antibody fragment) are directly and most substantially involved in influencing antigen binding. Humanization or engineering of antibodies of the present invention can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567, which are hereby incorporated by reference in their entirety for all purposes and in particular for all teachings related to humanization or engineering of antibodies.

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity 68(4): 1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Delivery Reviews 31:33-42; Green & Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417): 255-258; Jakobovits et al. (1993) Proc. Natl. Acad. Sci. USA 90(6):2551-2555; and U.S. Pat. No. 6,075,181.)

The antibodies of this invention also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies of this invention can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological Interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al. which discloses antibody variants that have one or more amino acids inserted into a hypervariable region of the parent antibody and a binding affinity for a target antigen which is at least about two fold stronger than the binding affinity of the parent antibody for the antigen.)

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Fd segments ($V_H$-$C_H$1-VH-$C_H$1) which form a pair of antigen binding regions. Linear antibodies can be bispecific or monospecific.

The antibodies of this invention can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present invention include naturally purified products, products of chemical synthetic procedures, and products produced by recombinant techniques from a eukaryotic host, including, for example, yeast, higher plant, insect and mammalian cells, or alternatively from a prokaryotic cells as described above.

If a monoclonal antibody being tested binds with protein or polypeptide, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding the protein or polypeptide with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with a protein with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term "antibody" also is intended to include antibodies of all isotypes. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307.

The isolation of other hybridomas secreting monoclonal antibodies with the specificity of the monoclonal antibodies of the invention can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody produced by the hybridoma of interest.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

In some aspects of this invention, it will be useful to detectably or therapeutically label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow & Lane (1988) supra.

The antibodies of the invention also can be bound to many different carriers. Thus, this invention also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

In certain embodiments, antibodies of the invention include mutations in the constant region that improve pharmacokinetic properties of the antibodies as compared to antibodies without such mutations. Such antibodies will in certain embodiments include an Fc domain that is derived from human IgG1 at the C-terminus, which in yet further embodiments include mutations that diminish or ablate antibody-dependent and complement dependent cytotoxicity. In a still further embodiment, such mutations include one or more of the following mutations singly or in any combination: E233P; L234V; L235A; ΔG236; A327G; A330S; P331S. In a yet further embodiment, the Fc domain comprises a sequence according to SEQ ID NO: 3, which is shown in FIG. 10. In a still further embodiment, the Fc domain comprises a sequence with a sequence identity of about 70%, 75%, 80%, 85%, 90%, 91%, 92%, 93%, 94%, 95%, 96%, 97%, 98%, 99% and 100% identity to SEQ ID NO: 3.

In further embodiments, one or more amino acid modifications are made in one or more of the CDRs of the antibody. In general, only 1 or 2 or 3 amino acids are substituted in any single CDR, and generally no more than from 4, 5, 6, 7, 8 9 or 10 changes are made within a set of CDRs. However, it should be appreciated that any combination of no substitutions, 1, 2 or 3 substitutions in any CDR can be independently and optionally combined with any other substitution.

In some cases, amino acid modifications in the CDRs are referred to as "affinity maturation". An "affinity matured" antibody is one having one or more alteration(s) in one or more CDRs which results in an improvement in the affinity of the antibody for antigen, compared to a parent antibody which does not possess those alteration(s). In some cases, although rare, it may be desirable to decrease the affinity of an antibody to its antigen, but this is generally not preferred.

Affinity maturation can be conducted to increase the binding affinity of the antibody for the antigen by at least about 10% to 50-100-150% or more, or from 1 to 5 fold as compared to the "parent" antibody. Preferred affinity matured antibodies will have nanomolar or even picomolar affinities for the target antigen. Affinity matured antibodies are produced by known procedures. See, for example, Marks et al., 1992, Biotechnology 10:779-783 that describes affinity maturation by variable heavy chain (VH) and variable light chain (VL) domain shuffling. Random mutagenesis of CDR and/or framework residues is described in: Barbas, et al. 1994, Proc. Nat. Acad. Sci, USA 91:3809-3813; Shier et al., 1995, Gene 169:147-155; Yelton et al., 1995, J. Immunol. 155:1994-2004; Jackson et al., 1995, J. Immunol. 154(7):3310-9; and Hawkins et al, 1992, J. Mol. Biol. 226:889-896, for example.

Alternatively, amino acid modifications can be made in one or more of the CDRs of the antibodies of the invention that are "silent", e.g. that do not significantly alter the affinity of the antibody for the antigen. These can be made for a number of reasons, including optimizing expression (as can be done for the nucleic acids encoding the antibodies of the invention).

Thus, included within the definition of the CDRs and antibodies of the invention are variant CDRs and antibodies; that is, the antibodies of the invention can include amino acid modifications in one or more of the CDRs of Ab79 and Ab19. In addition, as outlined below, amino acid modifications can also independently and optionally be made in any region outside the CDRs, including framework and constant regions.

In some embodiments, the antibodies of the invention are conjugated with drugs to form antibody-drug conjugates (ADCs). In general, ADCs are used in oncology applications, where the use of antibody-drug conjugates for the local delivery of cytotoxic or cytostatic agents allows for the targeted delivery of the drug moiety to tumors, which can allow higher efficacy, lower toxicity, etc. An overview of this technology is provided in Ducry et al., Bioconjugate Chem., 21:5-13 (2010), Carter et al., Cancer J. 14(3):154 (2008) and Senter, Current Opin. Chem. Biol. 13:235-244 (2009), all of which are hereby incorporated by reference in their entirety for all purposes and in particular for all teachings related to antibody drug conjugates.

Thus, in some embodiments, the invention provides Toso antibodies conjugated to drugs. Generally, conjugation is done by covalent attachment to the antibody and generally relies on a linker, often a peptide linkage (which, as is known in the art, may be designed to be sensitive to cleavage by proteases at the target site or not). In addition, as described above, linkage of the linker-drug unit (LU-D) can be done by attachment to cysteines within the antibody. As will be appreciated by those in the art, the number of drug moieties per antibody can change, depending on the conditions of the reaction, and can vary from 1:1 to 10:1 drug:antibody. As will be appreciated by those in the art, the actual number is an average.

The drug of the ADC can be any number of agents, including but not limited to cytotoxic agents such as chemotherapeutic agents, growth inhibitory agents, toxins (for example, an enzymatically active toxin of bacterial, fungal, plant, or animal origin, or fragments thereof), or a radioactive isotope (that is, a radioconjugate) are provided. In other embodiments, the invention further provides methods of using the ADCs.

Drugs for use in antibody-drug conjugates of the present invention include cytotoxic drugs, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, maytansinoids, differentiation inducers, and taxols.

Members of these classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, caminomycin, aminopterin, tallysomycin, podophyllotoxin and podophyllotoxin derivatives such as etoposide or etoposide phosphate, vinblastine, vincristine, vindesine, taxanes including taxol, taxotere retinoic acid, butyric acid, N8-acetyl spermidine, camptothecin, calicheamicin, esperamicin, ene-diynes, duocarmycin A, duocarmycin SA, calicheamicin, camptothecin, maytansinoids (including DM1), monomethylauristatin E (MMAE), monomethylauristatin F (MMAF), and maytansinoids (DM4) and their analogues.

Toxins may be used as antibody-toxin conjugates and include bacterial toxins such as diphtheria toxin, plant toxins such as ricin, small molecule toxins such as geldanamycin (Mandler et al (2000) J. Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). Toxins may exert their cytotoxic and cytostatic effects by mechanisms including tubulin binding, DNA binding, or topoisomerase inhibition.

Conjugates of a Toso antibody and one or more small molecule toxins, such as a maytansinoids, dolastatins, auristatins, a trichothecene, calicheamicin, and CC1065, and the derivatives of these toxins that have toxin activity, are contemplated.

In accordance with any of the above, another type of modification that can be made to antibodies of the invention is alterations in glycosylation. In another embodiment, the antibodies disclosed herein can be modified to include one or more engineered glycoforms. By "engineered glycoform" as used herein is meant a carbohydrate composition that is covalently attached to the antibody, wherein said carbohydrate composition differs chemically from that of a parent antibody. Engineered glycoforms may be useful for a variety of purposes, including but not limited to enhancing or reducing effector function. An exemplary form of engineered glycoform is afucosylation, which has been shown to be correlated to an increase in ADCC function, presumably through tighter binding to the FcγRIIIa receptor. In this context, "afucosylation" means that the majority of the antibody produced in the host cells is substantially devoid of fucose, e.g. 90-95-98% of the generated antibodies do not have appreciable fucose as a component of the carbohydrate moiety of the antibody (generally attached at N297 in the Fc region). Defined functionally, afucosylated antibodies generally exhibit at least a 50% or higher affinity to the FcγRIIIa receptor.

Engineered glycoforms may be generated by a variety of methods known in the art (Umana et al., 1999, Nat Biotechnol 17:176-180; Davies et al., 2001, Biotechnol Bioeng 74:288-294; Shields et al., 2002, J Biol Chem 277:26733-

26740; Shinkawa et al., 2003, J Biol Chem 278:3466-3473; U.S. Pat. No. 6,602,684; U.S. Ser. No. 10/277,370; U.S. Ser. No. 10/113,929; PCT WO 00/61739A1; PCT WO 01/29246A1; PCT WO 02/31140A1; PCT WO 02/30954A1, all entirely incorporated by reference in their entirety for all purposes and in particular for all teachings related to engineered glycoforms. Many of these techniques are based on controlling the level of fucosylated and/or bisecting oligosaccharides that are covalently attached to the Fc region, for example by expressing an IgG in various organisms or cell lines, engineered or otherwise (for example Lec-13 CHO cells or rat hybridoma YB2/0 cells, by regulating enzymes involved in the glycosylation pathway (for example FUT8 [α1,6-fucosyltransferase] and/or β1-4-N-acetylglucosaminyltransferase III [GnTIII]), or by modifying carbohydrate(s) after the IgG has been expressed. For example, the "sugar engineered antibody" or "SEA technology" of Seattle Genetics functions by adding modified saccharides that inhibit fucosylation during production; see for example 20090317869, hereby incorporated by reference in its entirety. Engineered glycoform typically refers to the different carbohydrate or oligosaccharide; thus an antibody can include an engineered glycoform.

Alternatively, engineered glycoform may refer to a variant that comprises the different carbohydrate or oligosaccharide. As is known in the art, glycosylation patterns can depend on both the sequence of the protein (e.g., the presence or absence of particular glycosylation amino acid residues, discussed below), or the host cell or organism in which the protein is produced. Particular expression systems are known in the art and discussed herein.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to an antibody (or to any other polypeptide, such as the soluble Toso protein discussed above) is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on an antibody or another protein is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 and in Aplin and Wriston, 1981, CRC Crit. Rev. Biochem., pp. 259-306, both entirely incorporated by reference herein in their entirety for all purposes and in particular for all teachings related to coupling carbohydrate moieties to proteins.

Removal of carbohydrate moieties present on the starting antibody (e.g. post-translationally) may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, Arch. Biochem. Biophys. 259:52 and by Edge et al., 1981, Anal. Biochem. 118:131, both entirely incorporated by reference. Enzymatic cleavage of carbohydrate moieties on polypeptides can be achieved by the use of a variety of endo- and exo-glycosidases as described by Thotakura et al., 1987, Meth. Enzymol. 138:350, entirely incorporated by reference. Glycosylation at potential glycosylation sites may be prevented by the use of the compound tunicamycin as described by Duskin et al., 1982, J. Biol. Chem. 257:3105, entirely incorporated by reference. Tunicamycin blocks the formation of protein-N-glycoside linkages.

Another type of covalent modification of the antibody comprises linking the antibody to various nonproteinaceous polymers, including, but not limited to, various polyols such as polyethylene glycol, polypropylene glycol or polyoxyalkylenes, in the manner set forth in, for example, 2005-2006 PEG Catalog from Nektar Therapeutics (available at the Nektar website) U.S. Pat. Nos. 4,640,835; 4,496,689; 4,301,144; 4,670,417; 4,791,192 or 4,179,337, all entirely incorporated by reference for all purposes and in particular for all teachings related to linking antibodies to polymers. In addition, as is known in the art, amino acid substitutions may be made in various positions within the antibody to facilitate the addition of polymers such as PEG. See for example, U.S. Publication No. 2005/0114037A1, entirely incorporated by reference.

The present invention further includes the nucleic acids encoding the Toso antibodies of the invention. In the case where both a heavy and light chain constant domains are included in the antibody, generally these are made using nucleic acids encoding each, that are combined into standard host cells (e.g. CHO cells, etc.) to produce the tetrameric structure of the antibody. If only one constant domain is being made, only a single nucleic acid will be used.

Formulations of the antibodies used in accordance with the present invention can be prepared for storage by mixing an antibody having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol;

cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulations of the invention may also contain more than one active compound as necessary for the particular indication being treated, preferably those with complementary activities that do not adversely affect each other. For example, it may be desirable to provide antibodies with other specificities. Alternatively, or in addition, the composition may comprise a cytotoxic agent, cytokine, growth inhibitory agent and/or small molecule antagonist. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration should be sterile, or nearly so. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism has been shown to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

IV. Methods of Modulating Toso Activity

In one aspect, the present invention is directed to methods of modulating Toso activity. In one embodiment, methods of modulating Toso activity comprise inhibiting Toso activity. In other embodiments, methods of modulating Toso activity comprise increasing Toso activity.

In some embodiments, methods of the present invention involve directly modulating Toso activity. In an exemplary embodiment, such methods include applying an agent that binds to Toso, such as an antibody.

In other embodiments, Toso activity is modulated indirectly, for example by binding cognate ligands of Toso. In an exemplary embodiment, Toso activity is modulated by administering a soluble Toso protein.

In further embodiments, Toso activity is modulated by a combination of mechanisms, for example by administering a composition comprising an agent that binds to Toso in combination with a composition comprising an agent that binds to cognate ligands of Toso. In an exemplary embodiment, such a combination may include without limitation a Toso antibody and a soluble Toso protein.

As will be appreciated, methods of modulating Toso activity can include the use of any of the compositions described herein in any combination, including any one or more of SEQ ID NOs. 1-25 as well as any variants or modifications thereof as described herein.

V. Methods of Treating Disorders

In one aspect and in accordance with any of the above, the present invention provides methods of treating disorders by treating subjects in need thereof with a composition that modulates Toso activity, including without limitation a soluble Toso protein or an antibody to Toso.

In a specific embodiment and in accordance with any of the above, the present invention provides methods of treating disorders by treating subjects in need thereof with a composition that includes a soluble Toso protein. Without being limited by theory, one potential mechanism by which the soluble Toso protein is an effective treatment for these disorders is through modulating Toso activity. In certain embodiments, methods of treating disorders in accordance with the present invention includes administering a therapeutically effective amount of any of the soluble Toso proteins described herein, including soluble Toso proteins comprising any one or more of SEQ ID NOs: 1-25 or any variants thereof. In further embodiments, the soluble Toso proteins used to treat disorders, including diabetes, multiple sclerosis, asthma, and cancer include a polypeptide with about 70%, 75%, 80%, 85%, 90%, 91%, 92%, 93%, 94%, 95%, 96%, 97%, 98%, 99% identity to any one of SEQ ID NOs: 1-25. such polypeptides may further be modified in accordance with the methods described herein, including chemical modifications, for the treatment of any of the disorders described herein.

In further aspects, the present invention is directed to methods of treating disorders and diseases by administering a soluble Toso protein (or a variant thereof) to a subject. Soluble Toso proteins of the invention can be used to treat subjects suffering from without limitation: an autoimmune disorder (including without limitation Type 1 diabetes, multiple sclerosis, or rheumatoid arthritis), Type 2 diabetes, asthma, allergy chronic obstructive pulmonary disease ("COPD"), hyper-IgM syndrome, lupus, cancer, or a neutrophilia-associated disorder (including without limitation neutropenia, severe congenital neutropenia, cyclical neutropenia, antibody mediated neutropenia, reticular dysgenesis, leukocyte adhesion deficiency, familiar myeloproliferative disease, chronic myelogenous leukemia, familiar cold urticaria and leukocytosis, and chronic granulomatous disease). As will be appreciated, any of the soluble Toso proteins described herein, singly or in any combination, can be used to treat any of these disorders or diseases.

In further embodiments, a pharmaceutically acceptable amount of a soluble Toso protein is administered to a subject in need thereof to treat any of the disorders discussed herein. In some embodiments, the soluble Toso protein administered to the subject includes an extracellular Toso domain and/or an Fc domain and/or a signal sequence and/or a flexible linker. In still further embodiments, the soluble Toso protein comprises a sequence according to any one of SEQ ID NOs: 1-25. Combinations of any one of SEQ ID NOs.:1-25 may also be used, either as separate polypeptides or together as fusion proteins, to treat any of the disorders discussed herein. Such polypeptides may also be further modified, including chemically modified, in accordance with the description herein to treat such disorders. In still further embodiments, the soluble Toso protein used to treat any of the disorders described herein has a sequence comprising SEQ ID NO: 5, which is shown in FIG. 8. In yet further embodiments, the soluble Toso protein administered to a subject for the treatment of any of the disorders discussed herein has a sequence with at least about 70%, 75%, 80%, 85%, 90%, 91%, 92%, 93%, 94%, 95%, 96%, 97%, 98%, 99% identity to SEQ ID NO. 5. In further embodiments, the soluble Toso protein administered to a subject for the treatment of any of the disorders discussed herein has a sequence with about 75-99%, 80-98%, 85-97%, 90-96%, 91-99%, 92-98%, 93-97%, 94-96% identity to SEQ ID NO: 5. In still further embodiments, the soluble Toso protein administered to the subject for the treatment of any of the disorders discussed herein comprises SEQ ID NO. 5 with 1, 2, 3, 4, 5, 6, 7, 8, 9, 10, 11, 12, 13, 14, 15, 16, 17, 18, 19, or 20 amino acid substitutions. In yet further embodiments, the soluble Toso protein administered to the subject for the treatment of diabetes comprises SEQ ID NO: 5 with 1-30, 2-25, 3-20, 4-15, 5-10, 6-9, 7-8 amino acid substitutions. In further exemplary embodiments, about 12.1, 12.2, 12.3, 12.4, 12.5, 12.6, 12.7, 12.8, 12.9, 13.1, 13.2, 13.3, 13.4, 13.5, 13.6, 13.7, 13.8, 13.9, 14 mg of the soluble Toso protein is administered to the subject for a therapeutic effect. As will be appreciated, the amount of soluble Toso protein can be ascertained based on animal studies using the widely accepted Body Surface Area (BSA) normalization method used for the conversion of dosages from experimental animals to humans. (see Reagan-Shaw, S., Nihal, M., and Admad, N. Dose translation from animal to human studies revisited. 2007. *The Faseb Journal*).

In specific embodiments, methods and compositions of the invention are used to treat subjects at risk for or that have Type 1 or Type 2 diabetes. In further embodiments, a pharmaceutically acceptable amount of a soluble Toso protein is administered to a subject in need thereof. In some embodiments, the soluble Toso protein administered to the subject to treat diabetes includes an extracellular Toso domain and/or an Fc domain and/or a signal sequence and/or a linker. In still further embodiments, the soluble Toso protein comprises a sequence according to any one of SEQ ID NOs: 1-25 or any of the variants of SEQ ID NOs: 1-25 discussed herein. In yet further embodiments, the soluble Toso protein administered to a subject for the treatment of diabetes includes a sequence with at least about 70%, 75%, 80%, 85%, 90%, 91%, 92%, 93%, 94%, 95%, 96%, 97%, 98%, 99% identity to any one of SEQ ID NOs: 1-25. Combinations of any one of SEQ ID NOs.:1-25 may also be used, either as separate polypeptides or together as fusion proteins, to treat diabetes. Such polypeptides may also be further modified, including chemically modified, in accordance with the description herein to treat diabetes. In still further embodiments, the soluble Toso protein used to treat a subject for diabetes has a sequence comprising SEQ ID NO: 5, which is shown in FIG. 8. In yet further embodiments, the soluble Toso protein administered to a subject for the treatment of diabetes has a sequence with at least about 70%, 75%, 80%, 85%, 90%, 91%, 92%, 93%, 94%, 95%, 96%, 97%, 98%, 99% identity to SEQ ID NO. 5. In further embodiments, the soluble Toso protein administered to a subject for the treatment of diabetes has a sequence with about 75-99%, 80-98%, 85-97%, 90-96%, 91-99%, 92-98%, 93-97%, 94-96% identity to SEQ ID NO: 5. In still further embodiments, the soluble Toso protein administered to the subject for the treatment of diabetes comprises SEQ ID NO. 5 with 1, 2, 3, 4, 5, 6, 7, 8, 9, 10, 11, 12, 13, 14, 15, 16, 17, 18, 19, or 20 amino acid substitutions. In yet further embodiments, the soluble Toso protein administered to the subject for the treatment of diabetes comprises SEQ ID NO: 5 with 1-30, 2-25, 3-20, 4-15, 5-10, 6-9, 7-8 amino acid substitutions. In still further embodiments, treatment with a soluble Toso protein in accordance with any of the compositions described herein serves to improve glucose tolerance in a subject, and thereby treat diabetes. In exemplary embodiments, about 10-20, 11-19, 12-18, 13-17, 14-16 mg of the soluble Toso protein is administered to the subject for a therapeutic effect. In further exemplary embodiments, about 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16 mg of the soluble Toso protein is administered to the subject for a therapeutic effect. As will be appreciated, the amount of soluble Toso protein can be ascertained based on animal studies using the widely accepted Body Surface Area (BSA) normalization method used for the conversion of dosages from experimental animals to humans. (see Reagan-Shaw, S., Nihal, M., and Admad, N. Dose translation from animal to human studies revisited. 2007. *The Faseb Journal*). For the experiments described in further detail herein, 50 μg doses were used in the disease models, which would approximately be 2.5 mg/kg in a 20 g mouse. Using the BSA conversion, this would be 0.2027 mg/kg or 7.5 mg/m$^2$, or approximately 12.2 mg for a 60 kg adult.

In other embodiments, methods and compositions of the invention are used to treat subjects at risk for or that have multiple sclerosis. In further embodiments, a pharmaceutically acceptable amount of a soluble Toso protein is administered to a subject in need thereof for the treatment or amelioration of multiple sclerosis. In some embodiments, the soluble Toso protein administered to the subject includes and Fc domain and/or a flexible linker. In some embodiments, the soluble Toso protein administered to the subject includes an extracellular Toso domain and/or an Fc domain and/or a signal sequence and/or a linker. In still further embodiments, the soluble Toso protein comprises a sequence according to any one of SEQ ID NOs: 1-24. Combinations of any one of SEQ ID NOs.:1-25 may also be used, either as separate polypeptides or together as fusion proteins, to treat multiple sclerosis. Such polypeptides may also be further modified, including chemically modified, in accordance with the description herein to treat multiple sclerosis. In still further embodiments, the soluble Toso protein has a sequence comprising SEQ ID NO: 5, which is shown in FIG. 8. In yet further embodiments, the soluble Toso protein administered to a subject for the treatment of multiple sclerosis has a sequence with at least about 70%, 75%, 80%, 85%, 90%, 91%, 92%, 93%, 94%, 95%, 96%, 97%, 98%, 99% identity to SEQ ID NO. 5. In further embodiments, the soluble Toso protein administered to a subject for the treatment of multiple sclerosis has a sequence with about 75-99%, 80-98%, 85-97%, 90-96%, 91-99%, 92-98%, 93-97%, 94-96% identity to SEQ ID NO: 5. In still further embodiments, the soluble Toso protein administered to the subject for the treatment of multiple sclerosis comprises SEQ ID NO. 5 with 1, 2, 3, 4, 5, 6, 7, 8, 9, 10, 11, 12, 13, 14, 15, 16, 17, 18, 19, or 20 amino acid substitutions. In yet further embodiments, the soluble Toso protein administered to the subject for the treatment of multiple sclerosis comprises SEQ ID NO: 5 with 1-30, 2-25, 3-20, 4-15, 5-10, 6-9, 7-8 amino acid substitutions. In still further embodiments, treatment with a soluble Toso protein in accordance with any of the compositions described herein serves to delay the progression of multiple sclerosis. In exemplary embodiments, about 10-20, 11-19, 12-18, 13-17, 14-16 mg of the soluble Toso protein is administered to the subject for a therapeutic effect. In further exemplary embodiments, about 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16 mg of the soluble Toso protein is administered to the subject for a therapeutic effect. As will be appreciated, the amount of soluble Toso protein can be ascertained based on animal studies using the widely accepted Body Surface Area (BSA) normalization method used for the conversion of dosages from experimental animals to humans. (see Reagan-Shaw, S., Nihal, M., and Admad, N. Dose translation from animal to human studies revisited. 2007. *The Faseb Journal*). For the experiments described in further detail herein, 50 µg doses were used in the disease models, which would approximately be 2.5 mg/kg in a 20 g mouse. Using the BSA conversion, this would be 0.2027 mg/kg or 7.5 mg/m², or approximately 12.2 mg for a 60 kg adult.

In other embodiments, methods and compositions of the invention are used to treat subjects at risk for or that have arthritis. In further embodiments, a pharmaceutically acceptable amount of a soluble Toso protein is administered to a subject in need thereof for the treatment or prevention of arthritis. In some embodiments, the soluble Toso protein administered to the subject includes and Fc domain and/or a linker. In some embodiments, the soluble Toso protein administered to the subject includes an extracellular Toso domain and/or an Fc domain and/or a signal sequence and/or a linker. In still further embodiments, the soluble Toso protein comprises a sequence according to any one of SEQ ID NOs: 1-25 Combinations of any one of SEQ ID NOs:1-25 may also be used, either as separate polypeptides or together as fusion proteins, to treat arthritis. Such polypeptides may also be further modified, including chemically modified, in accordance with the description herein to treat arthritis. In still further embodiments, the soluble Toso protein has a sequence comprising SEQ ID NO: 5, which is shown in FIG. 8. In yet further embodiments, the soluble Toso protein administered to a subject for the treatment of arthritis has a sequence with at least about 70%, 75%, 80%, 85%, 90%, 91%, 92%, 93%, 94%, 95%, 96%, 97%, 98%, 99% identity to SEQ ID NO. 5. In further embodiments, the soluble Toso protein administered to a subject for the treatment of arthritis has a sequence with about 75-99%, 80-98%, 85-97%, 90-96%, 91-99%, 92-98%, 93-97%, 94-96% identity to SEQ ID NO: 5. In still further embodiments, the soluble Toso protein administered to the subject for the treatment of arthritis comprises SEQ ID NO. 5 with 1, 2, 3, 4, 5, 6, 7, 8, 9, 10, 11, 12, 13, 14, 15, 16, 17, 18, 19, or 20 amino acid substitutions. In yet further embodiments, the soluble Toso protein administered to the subject for the treatment of arthritis comprises SEQ ID NO: 5 with 1-30, 2-25, 3-20, 4-15, 5-10, 6-9, 7-8 amino acid substitutions. In still further embodiments, treatment with a soluble Toso protein in accordance with any of the compositions described herein serves to prevent the incidence of arthritis or protect against the severity of arthritis.

In specific embodiments, methods and compositions of the invention are used to treat subjects at risk for or that have asthma. In further embodiments, a pharmaceutically acceptable amount of a soluble Toso protein is administered to a subject in need thereof. In some embodiments, the soluble Toso protein administered to the subject to treat asthma includes an extracellular Toso domain and/or an Fc domain and/or a signal sequence and/or a linker. In still further embodiments, the soluble Toso protein comprises a sequence according to any one of SEQ ID NOs: 1-25 or any of the variants of SEQ ID NOs: 1-25 discussed herein. In yet further embodiments, the soluble Toso protein administered to a subject for the treatment of asthma includes a sequence with at least about 70%, 75%, 80%, 85%, 90%, 91%, 92%, 93%, 94%, 95%, 96%, 97%, 98%, 99% identity to any one of SEQ ID NOs: 1-25. Combinations of any one of SEQ ID NOs.:1-25 may also be used, either as separate polypeptides or together as fusion proteins, to treat asthma. Such polypeptides may also be further modified, including chemically modified, in accordance with the description herein to treat asthma. In still further embodiments, the soluble Toso protein used to treat a subject for asthma has a sequence comprising SEQ ID NO: 5, which is shown in FIG. 8. In yet further embodiments, the soluble Toso protein administered to a subject for the treatment of asthma has a sequence with at least about 70%, 75%, 80%, 85%, 90%, 91%, 92%, 93%, 94%, 95%, 96%, 97%, 98%, 99% identity to SEQ ID NO. 5. In further embodiments, the soluble Toso protein administered to a subject for the treatment of asthma has a sequence with about 75-99%, 80-98%, 85-97%, 90-96%, 91-99%, 92-98%, 93-97%, 94-96% identity to SEQ ID NO: 5. In still further embodiments, the soluble Toso protein administered to the subject for the treatment of asthma comprises SEQ ID NO. 5 with 1, 2, 3, 4, 5, 6, 7, 8, 9, 10, 11, 12, 13, 14, 15, 16, 17, 18, 19, or 20 amino acid substitutions. In yet further embodiments, the soluble Toso protein administered to the subject for the treatment of asthma comprises SEQ ID NO: 5 with 1-30, 2-25, 3-20, 4-15, 5-10, 6-9, 7-8 amino acid substitutions. In still further embodiments, treatment with a soluble Toso protein in accordance with any of the compositions described herein serves to improve glucose tolerance in a subject, and thereby treat asthma. In exemplary embodiments, about 10-20, 11-19, 12-18, 13-17, 14-16 mg of the soluble Toso protein is administered to the subject for a therapeutic effect. In further exemplary embodiments, about 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16 mg of the soluble Toso protein is administered to the subject for a therapeutic effect. As will be appreciated, the amount of soluble Toso protein can be ascertained based on animal studies using the widely accepted Body Surface Area (BSA) normalization method used for the conversion of dosages from experimental animals to humans. (see Reagan-Shaw, S., Nihal, M., and Admad, N. Dose translation from animal to human studies revisited. 2007. *The Faseb Journal*). For the experiments described in further detail herein, 50 μg doses were used in the disease models, which would approximately be 2.5 mg/kg in a 20 g mouse. Using the BSA conversion, this would be 0.2027 mg/kg or 7.5 mg/m$^2$, or approximately 12.2 mg for a 60 kg adult.

In further embodiments, the soluble Toso proteins described herein, including the soluble Toso proteins comprising any one or more of the polypeptides of SEQ ID NOs. 1-25, is in the form for use as a medicament. In further embodiments, the present invention provides a soluble Toso protein comprising any one or more (or a portion of any one or more) of the polypeptides of SEQ ID NOs. 1, 2, 3, 4, 5, 6, 7, 8, 9, 10, 11, 12, 13, 14, 15, 16, 17, 18, 19, 20, 21, 22, 23, 24, or 25 for use as a medicament. In still further embodiments, the present invention provides methods for the use of a soluble Toso protein comprising any one or more of the polypeptides of SEQ ID NOs. 1-25 for treating any one of the following disorders: an autoimmune disorder (including without limitation Type 1 or Type 2 diabetes, multiple sclerosis, or rheumatoid arthritis), asthma, allergy chronic obstructive pulmonary disease ("COPD"), hyper-IgM syndrome, lupus, cancer, or a neutrophilia-associated disorder (including without limitation neutropenia, severe congenital neutropenia, cyclical neutropenia, antibody mediated neutropenia, reticular dysgenesis, leukocyte adhesion deficiency, familiar myeloproliferative disease, chronic myelogenous leukemia, familiar cold urticaria and leukocytosis, and chronic granulomatous disease).

As discussed above, in some embodiments, soluble Toso proteins of the invention are used to treat cancer. In further embodiments, methods of treating cancer in accordance with the invention include methods of inhibiting tumor invasion and/or metastasis by modulating Toso activity. In exemplary embodiments, compositions of the invention are used to treat any one of the group of an adenocarcinoma, a leukemia, a lymphoma, a melanoma, a myeloma, a sarcoma or a teratocarcinoma in subjects in need thereof. In further embodiments, compositions of the invention are used to treat subjects suffering from a cancer in one or more of adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid or uterus.

Example 1

Toso Plays a Role in the Pathogenesis of Arthritis

Figure 1B:
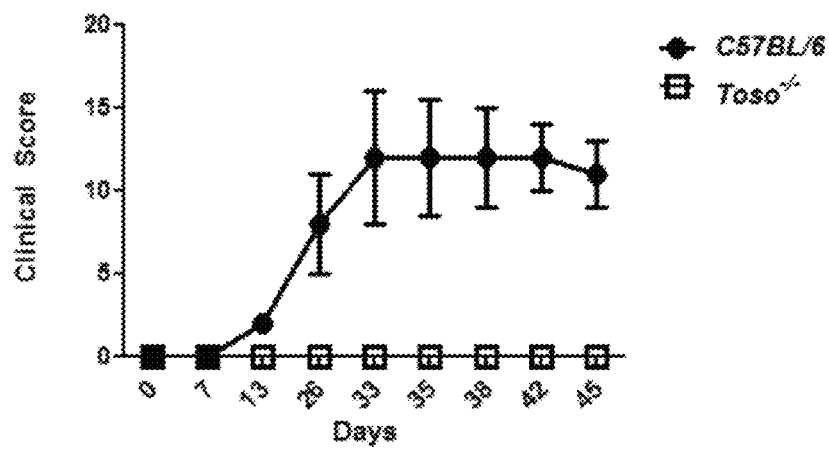
Figure 1C:
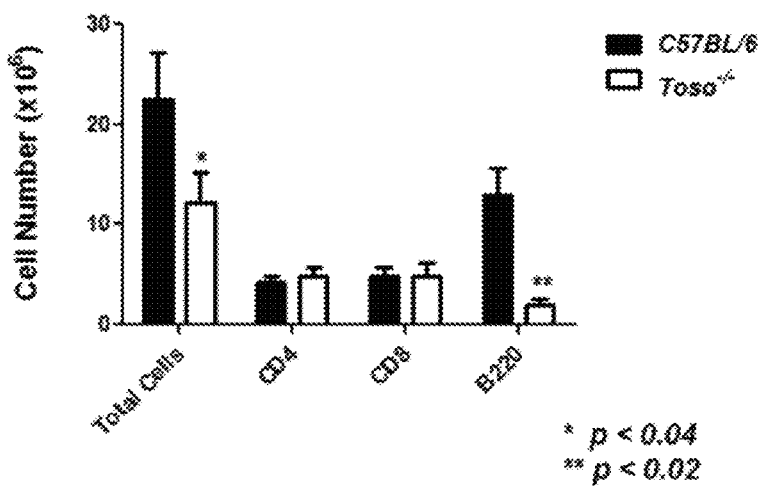

Toso$^{-/-}$ and wild type mice were injected with Type II chicken collagen in Complete Freund's adjuvant subcutaneously and monitored the disease progression over time. Animals exposed to Type II collagen develop disease that has similar immunologic, pathologic and histological features as human Rheumatoid Arthritis (RA). Joint inflammation, as measured by the change in ankle thickness using a digital caliper, was significantly reduced in Toso$^{-/-}$ mice (FIG. 1A). In addition, disease severity was scored from 0-4 for each joint based on visible swelling and mobility. Toso$^{-/-}$ mice had drastically reduced clinical scores compared to wild type controls (FIG. 1B). Flow cytometric analysis of lymphocyte populations in the draining lymph node showed a significant reduction in B220$^+$ B cells (FIG. 1C). These data suggest that Toso has a significant role in the pathogenesis of arthritis.

Example 2

Treatment with Toso-Fc Protects Against Arthritis

Figure 24A:
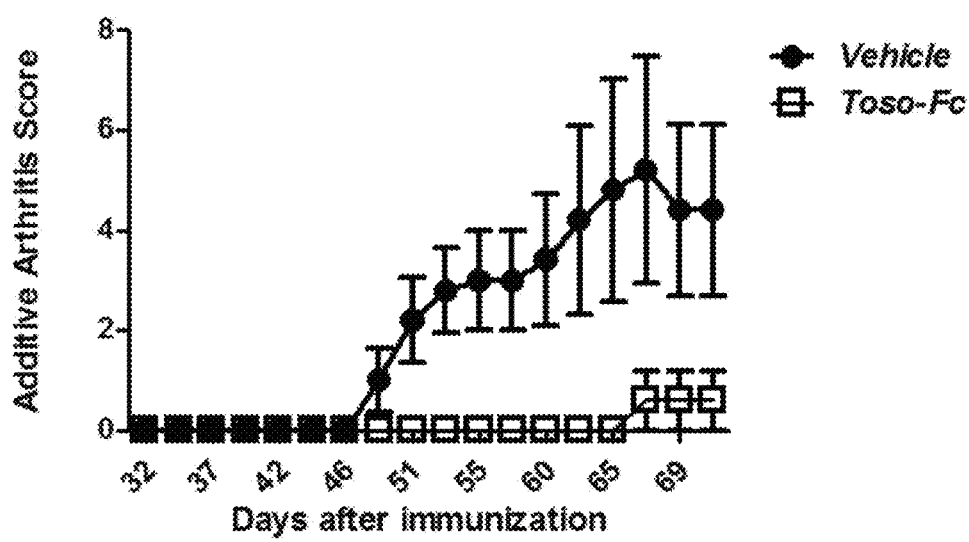
FIG. 24A shows data in an arthritis mouse model comparing the additive arthritis score in mice treated with the control vehicle (closed circle) and mouse treated with soluble Toso protein (Toso-Fc—open square).
Figure 24B:
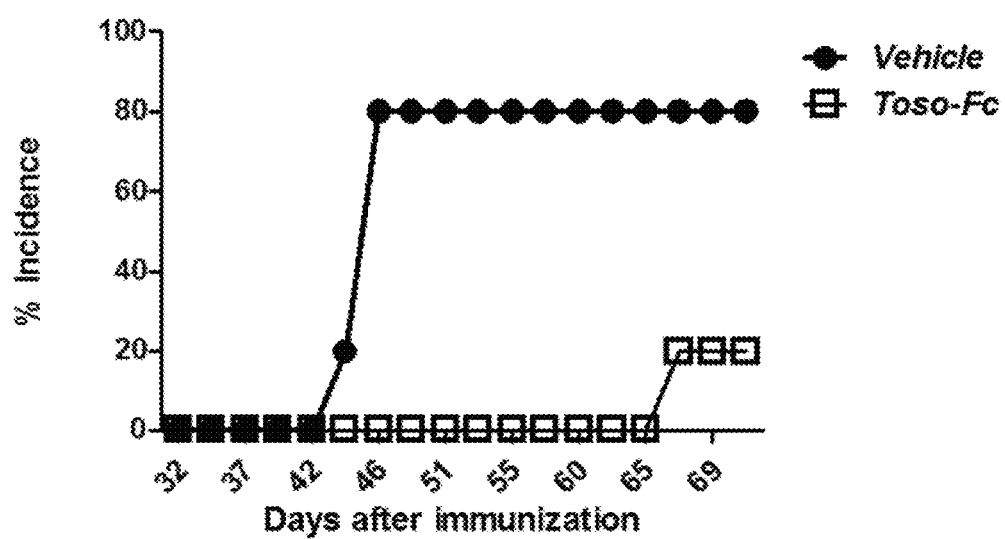
FIG. 24B shows data from an arthritis mouse model comparing the percent incidence of arthritis in the Toso-Fc treated mice (Toso-Fc—open squares) as compared to control (vehicle—closed circles).

This example shows that treatment with Toso-Fc (SEQ ID NO: 5) protects against arthritis. Arthritis susceptible mice, DBA1, were pre-dosed with 50 μg Toso-Fc I.P, immunized with Type II collagen in Complete Freund's Adjuvant to induce disease, and then treated with Toso-Fc three times per week over the course of the experiment. Toso-Fc treated mice were protected against both the severity and incidence of disease, suggesting that Toso-Fc administration may be useful in the management of arthritis. For example, FIG. 24A shows that the additive arthritis score was negligible in the Toso-Fc treated mice as compared to the control mice (treated only with the vehicle). Similarly, FIG. 24B also shows that the percent incidence of arthritis was negligible in the Toso-Fc treated mice as compared to control. Clinical symptoms of arthritis were assessed as follows; 0=normal, 1=slight swelling and/or erythema, 2=pronounced swelling, 3=ankylosis. The individual limb scores for each mouse were added, giving a maximum disease score of 12. Incidence of disease was noted when mice were observed to have a disease score of 1 in a limb.

Figure 25:
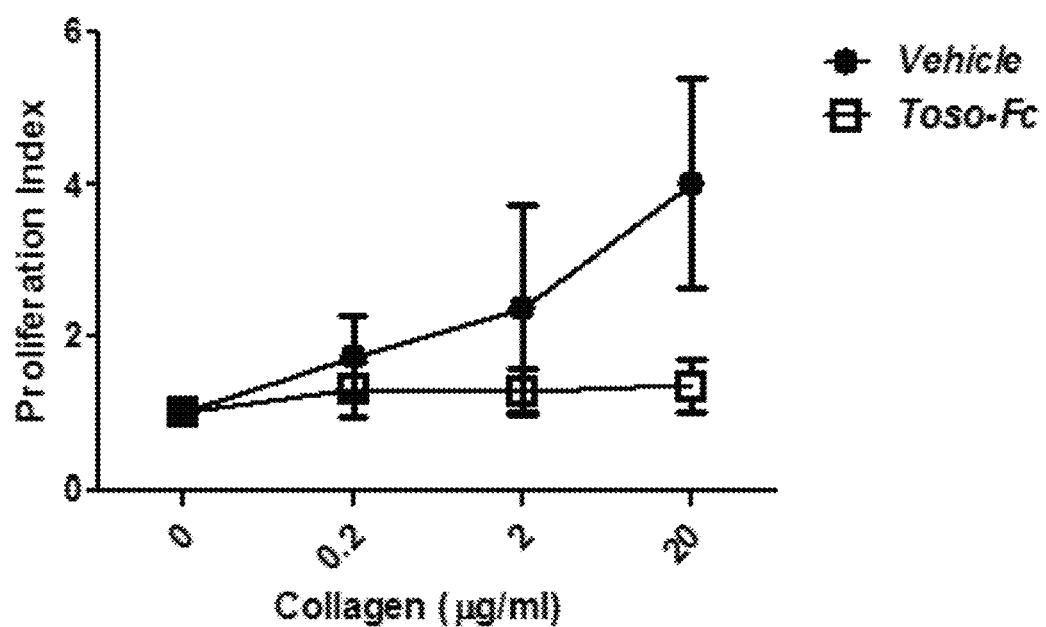
FIG. 25 shows reduced proliferative responses to collagen in splenocytes treated with Toso-Fc.

FIG. 25 provides further data showing the recall response (proliferation) of splenocytes from Toso-Fc and vehicle treated mice stimulated with Collagen. As shown in the figure, splenocytes from mice treated with Toso-Fc show a reduced proliferative response than splenocytes from vehicle treated controls.

Example 3

Toso-Fc is Effective Against Arthritis Once the Disease is Established

As shown above, prophylactic administration of Toso-Fc ameliorated disease symptoms in a murine model of rheumatoid arthritis. This example shows that the administration of the Toso-Fc is also effective in a therapeutic context (i.e., when disease is already established.

Figure 26A:
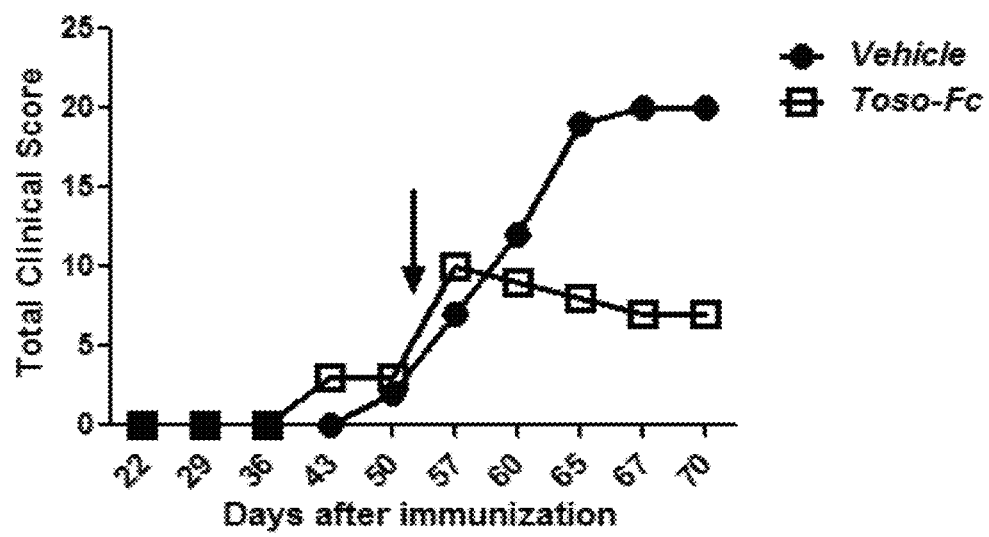
FIG. 26A and FIG. 26B show the therapeutic effect of soluble Toso protein (Toso-Fc—open square) in an arthritis mouse model as compared to control (vehicle—closed circle).
Figure 26B:
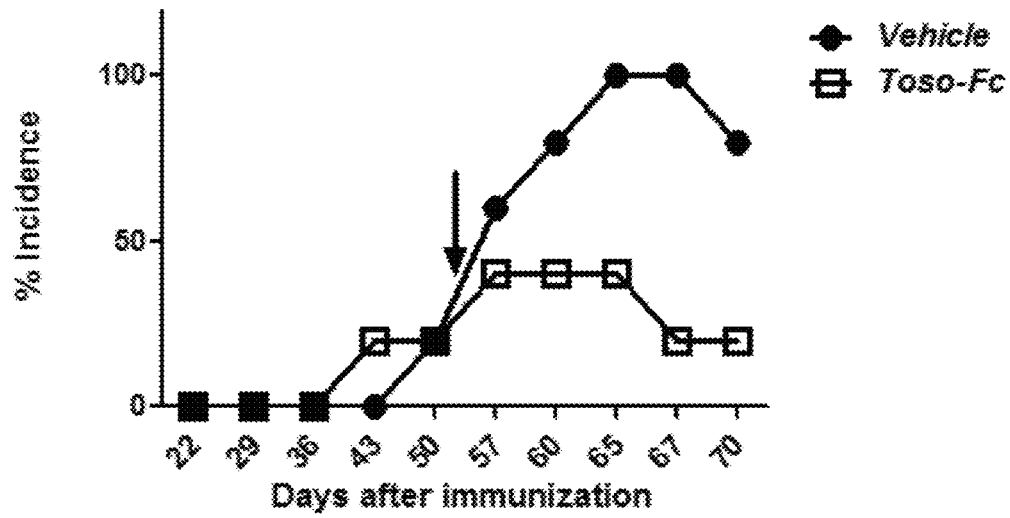

Female DBA.1 mice (6 to 8 weeks of age) were randomly assigned into 2 groups, one to receive vehicle treatment, and the other to receive Toso-Fc when disease was observed. All mice were inoculated with Collagen to induce disease. Initiation of disease symptoms were observed on day 43 after immunization. The animals were treated with vehicle control or Toso-Fc on day 52, as indicated by the arrow on the plots (FIG. 26A and FIG. 26B). After day 57, therapeutic administration of Toso-Fc dramatically reduced total disease score and arthritis incidence (see FIG. 26A and FIG. 26B). These data indicate that Toso-Fc can effectively manage arthritis symptoms when disease has already been established, and can thus be effective in a therapeutic as well as a prophylactic context.

Example 4

Toso Plays a Role in the Development of Asthma

Asthma is an allergic disorder characterized by aberrant TH2 activation, IgE production, bronchial hyperreactivity, and leukocyte extravasation into the bronchial mucosa.

Eosinophillia is a hallmark of allergic asthma and is thought to be a critical player in inflammation. The pathologic manifestations of asthma cause the lungs to constrict, leading to wheezing, shortness of breath, chest tightness, and coughing.

Figure 2A:
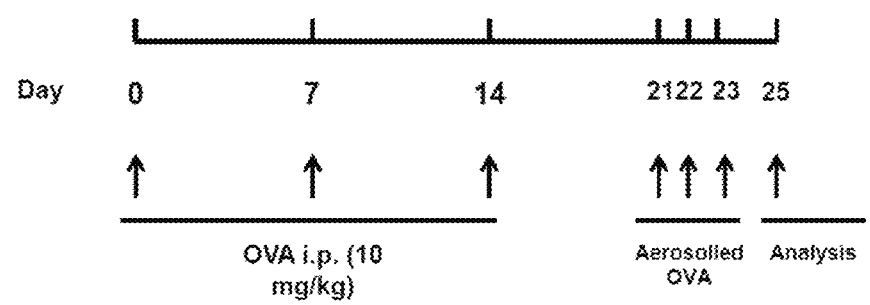
FIG. 2A, FIG. 2B and FIG. 2C show data from an OVA induced asthma model on Toso$^{-/-}$ and wild type mice.
Figure 2B:
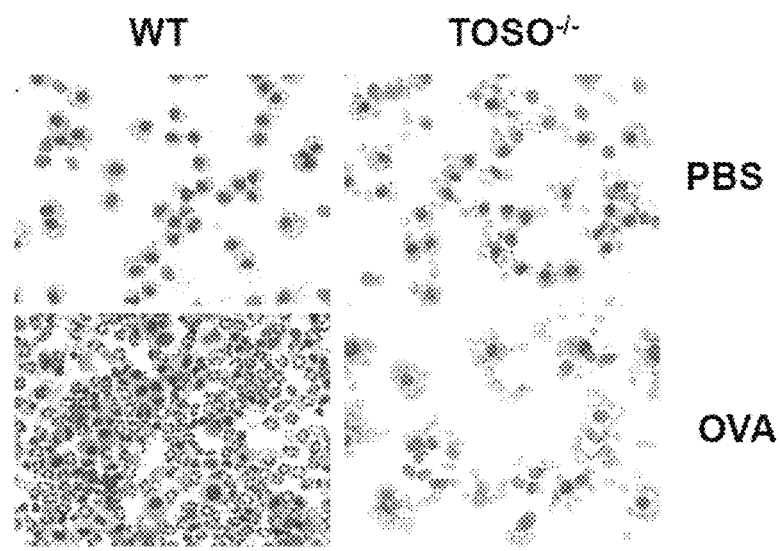
Figure 2C:
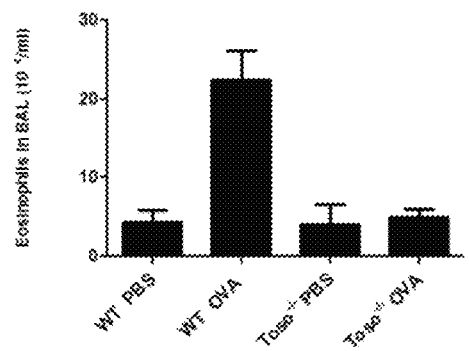

An OVA induced asthma model was conducted on Toso−/− and wild type mice (FIG. 2A). OVA (10 mg/kg) were delivered intraperitoneally on days 0, 7, and 14. Mice then received aerosolled OVA (1 mg/ml) for 30 minutes on days 21, 22, and 23, and sacrificed 2 days later. Toso−/− mice had a drastic reduction in eosinophil migration into the bronchioalveolar space as assessed by DifQuik staining (FIG. 2B). Based on morphology, eosinophils were quantified by counting at least 200 leukocytes per slide (FIG. 2C).

Figure 3A:
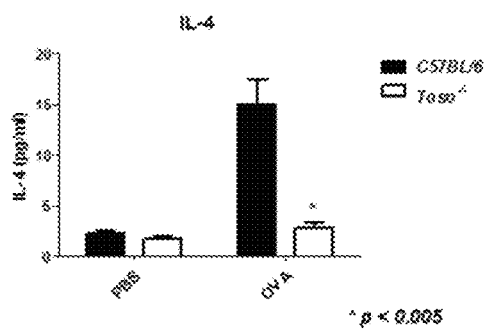
FIG. 3A, FIG. 3B and FIG. 3C show data on OVA induced T$_H$2 cytokines IL-4, IL-5 and IL-13 in BALF as assessed by ELISA.
Figure 3B:
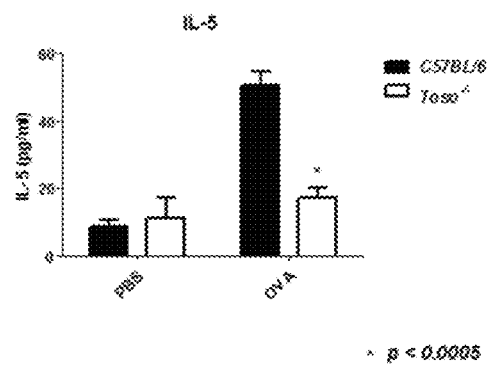
Figure 3C:
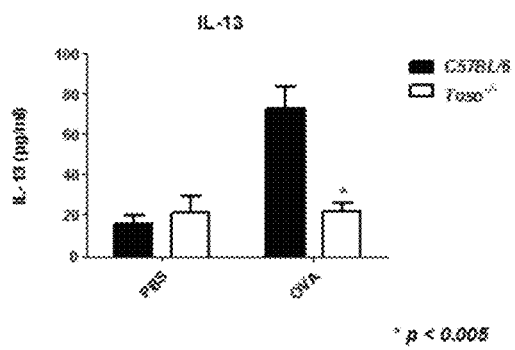
Figure 3D:
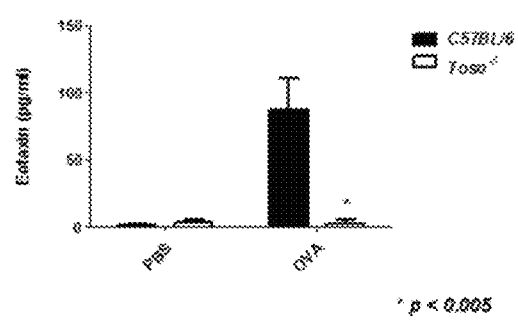
FIG. 3D shows data on Eotaxin, an eosinophil attracting C—C chemokine, in the BALF.
Figure 3E:
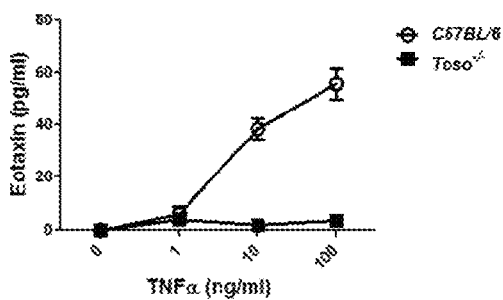
FIG. 3E shows the levels of Eotaxin produced in response to TNFα treatment in smooth muscle cells.

Asthma and other allergic diseases are typified by the preferential differentiation of naive T cells into TH2 cells. The presence TH2 relevant cytokines and chemokines in Bronchioalveolar lavage fluid (BALF) was assessed. Toso−/− mice had a significant reduction in OVA induced TH2 cytokines IL-4, IL-5 and IL-13 in BALF as assessed by ELISA (FIG. 3A-C). Consistent with the depressed eosinophil migration into the lung, Toso−/− mice had significantly reduced Eotaxin, an eosinophil attracting C—C chemokine, in the BALF (FIG. 3D). Bronchial smooth muscle cells are known to produce eotaxin in response to TNFα. Since Toso is known to be expressed in the lung, and Toso deficiency renders mice refractory to TNF, the inventors sought to address whether the effect of Toso on eotaxin levels was lung intrinsic. Cultured Toso−/− bronchial smooth muscle cells had significantly reduced levels of Eotaxin produced in response to TNFα treatment (FIG. 3E). Taken together, these data suggest that Toso deficiency impinges on OVA induced TH2 cytokine, and eotaxin levels in the lung.

Figure 4A:
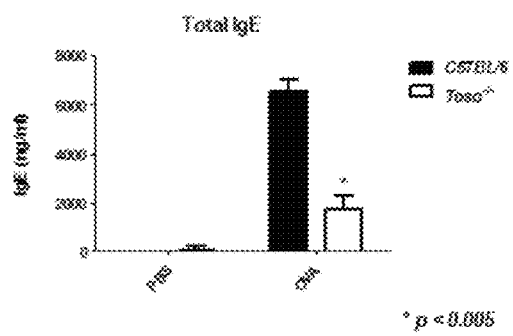
FIG. 4A, FIG. 4B and FIG. 4C show data on IgE in Toso$^{-/-}$ mice.
Figure 4B:
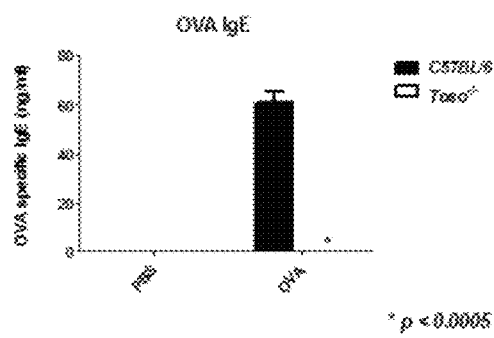
Figure 4C:
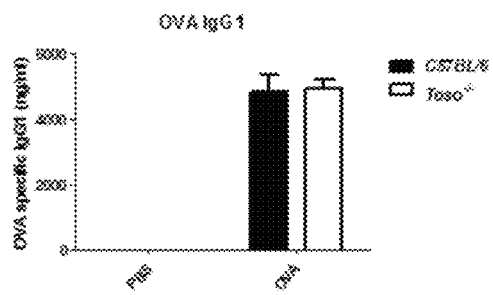

A hallmark of allergic asthma is the overproduction of IgE. Antibody producing B cells are induced to produce IgE by TH2 cytokines such as IL-4 (Oettgen, H. C. and R. S. Geha, IgE regulation and roles in asthma pathogenesis. J Allergy Clin Immunol, 2001. 107(3): p. 429-40). OVA induced total IgE and OVA specific IgE levels in the serum were significantly depressed in the Toso−/− mice (FIGS. 4A and B), while OVA-specific IgG1 were similar between wild type and knockout (FIG. 4C). These data suggest that genetic ablation of Toso, or perhaps therapeutic blockade, could decrease the production of IgE.

Figure 5:
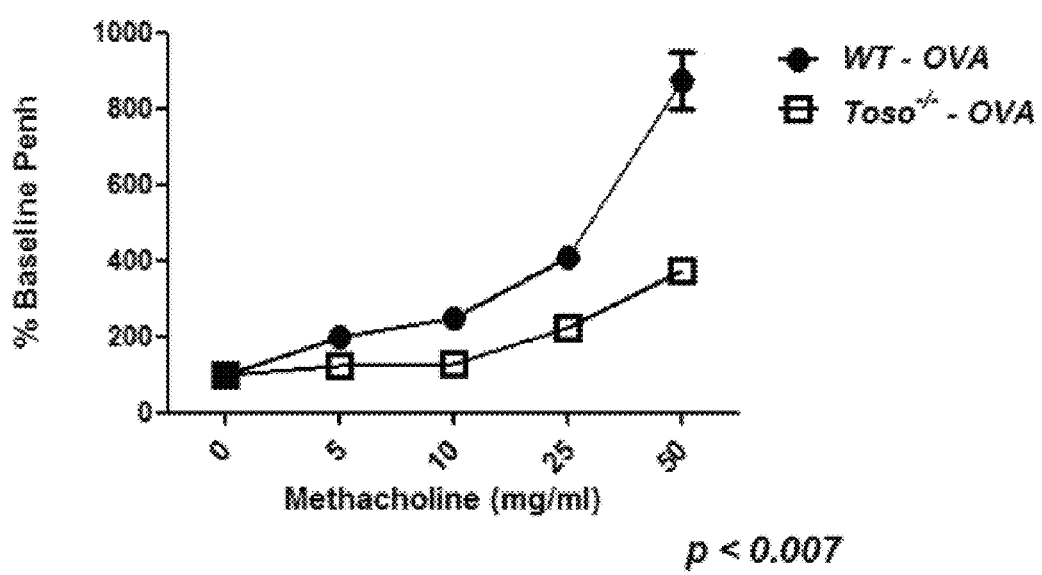
FIG. 5 shows Penh values of Toso$^{-/-}$ mice compared to wildtype controls.

The inflammatory events that typify allergic asthma culminate in airway remodeling that cause restrictive airflow to the lung. Therefore, whether Toso deficiency affected OVA induced airway hyper-responsiveness was assessed by measuring enhanced pause (Penh) in response to increasing doses of methacholine using whole body plethysmography. Toso−/− mice were significantly protected from OVA induced airway hyper-responsiveness as indicated by the significant reduction in Penh values compared to wild type controls (FIG. 5). These data are suggestive of Toso blocking being an efficient strategy for mitigating airway reactivity in allergic asthma.

Example 5

Toso Ablation Affects Dendritic Cell Activity

Toso ablation has wide-scale effects on the onset of allergic and inflammatory diseases. One possible non-limiting mechanism is that Toso regulates these disease processes at a global level, perhaps through the function of dendritic cells (DCs) to present antigen to naïve T cells.

In order to test the functional relevance of Toso$^{-/-}$ dendritic cells in the onset of disease or in the activation of T cells, the inventors determined whether the transfer of antigen loaded Toso−/− DCs elicited disease processes similar to wild type counterparts.

Figure 7A:
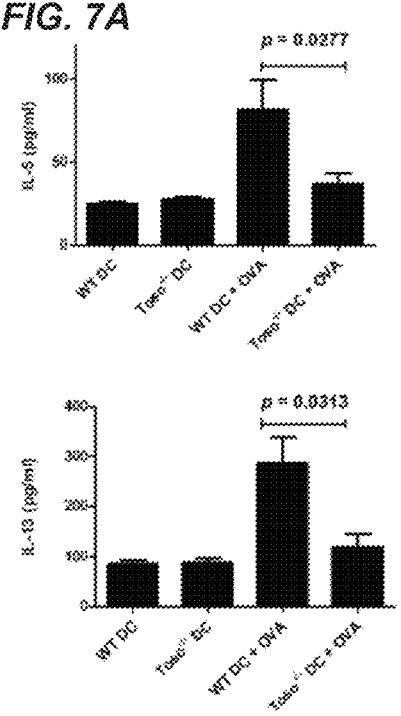
FIG. 7A shows data on cytokine production in the Broncho Alveolar Lavage Fluid (BALF) of wildtype animals in response to aerosolled OVA that had been previously intratracheally installed with Toso$^{-/-}$ and wildtype dendritic cells.
Figure 7B:
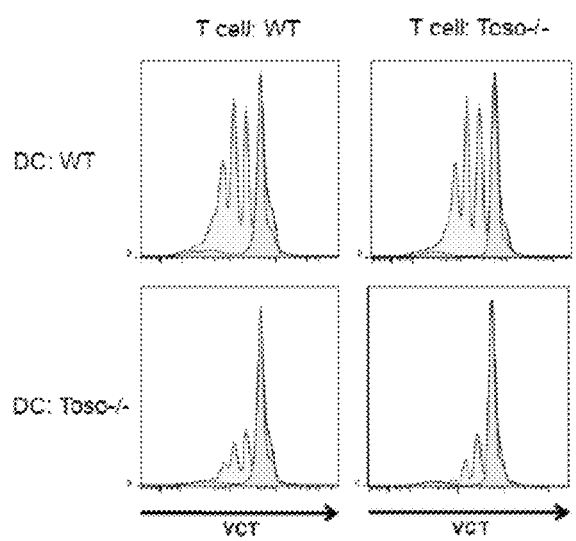
FIG. 7B shows proliferation of T cells derived from 2d2 mice cultured with MOG$_{35-55}$ loaded Toso$^{-/-}$ dendritic cells.
Figure 7C:
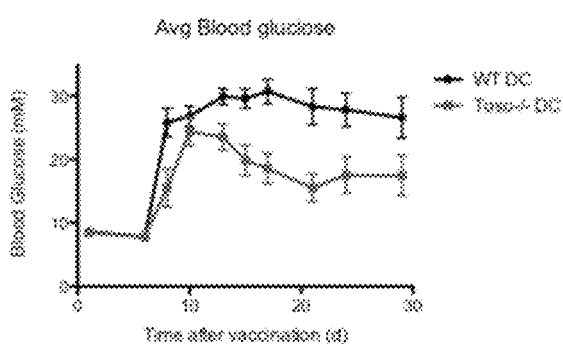
FIG. 7C shows blood glucose levels in RIP-GP animals injected intravenously with GP loaded Toso$^{-/-}$ and wildtype dendritic cells and a Kaplan-Meier plot of RIP-GP mice injected with GP peptide loaded wildtype and Toso$^{-/-}$ dendritic cells. RIP-GP mice are mice expressing the major glycoprotein (GP) from lymphocytic chorio meningitis virus (LCMV) under control of the rat insulin promoter (RIP)—such mice develop diabetes as assessed by increased levels of serum glucose.

Wild type and Toso−/− bone marrow derived DCs were made through culture with GM-CSF (see Lutz, M. B., et al., An advanced culture method for generating large quantities of highly pure dendritic cells from mouse bone marrow. J Immunol Methods, 1999. 223(1): p. 77-92, which is hereby incorporated by reference in its entirety for all purposes and in particular for all teaching regarding the culture of dendritic cells). Similar to the protocol of Lambrecht et al, the DCs in the present experiments were loaded with OVA. The antigen loaded DCs were instilled into the trachea of C57BL6 animals (see Lambrecht, B. N., et al., Myeloid dendritic cells induce Th2 responses to inhaled antigen, leading to eosinophilic airway inflammation. J Clin Invest, 2000. 106(4): p. 551-9, which is hereby incorporated by reference for all purposes and in particular for all teachings related to dendritic cells). One week later, the animal were treated with aerosolled OVA as per the asthma studies for three consecutive days. Strikingly, OVA loaded Toso$^{-/-}$ dendritic cells were significantly reduced in their capacity to induce TH2 cytokine production into the BALF as compared to wild type controls (FIG. 7A). The 2d2 TCR transgenic strain contains T cells that are specific for the MOG35-55 peptide used to elicit EAE (Bettelli, E., et al., Myelin oligodendrocyte glycoprotein-specific T cell receptor transgenic mice develop spontaneous autoimmune optic neuritis. J Exp Med, 2003. 197(9): p. 1073-81). T cells derived from 2d2 mice failed to proliferate when co-cultured with MOG35-55 loaded Toso−/− DCs (FIG. 7B). Mice expressing the major glycoprotein (GP) from lymphocytic chorio meningitis virus (LCMV) under control of the rat insulin promoter (RIP) develop diabetes as assessed by increased levels of serum glucose. Similarly, RIP-GP receiving GP peptide loaded DCs also develop disease. Toso−/− DCs show an impairment in their ability to elicit disease compared to wild type controls, and RIP-GP mice receiving peptide loaded Toso−/− DCs survive significantly better than those mice receiving peptide loaded wild type DCs (FIG. 7C). Taken together, these results suggest that Toso is necessary for the ability of Dendritic Cells to activate T cells and induce disease.

Example 6

Administration of a Soluble Toso Protein Abrogates Asthma Disease Metrics

To generate a soluble receptor, the extracellular domain of Toso from human spleen cDNA library was amplified and then cloned in-frame with an Fc domain derived from human IgG1 at the C-terminus into pFuse-hIgG1e3-Fc2 downstream of an IL2 signal sequence, allowing for optimal secretion into the culture supernatant (FIG. 8A—signal sequence indicated by a box, and Fc domain indicated with the underline). In addition, the Fc region contained several mutations (E233P/L234V/L235A/ΔG236/A327G/A330S/P331S) that have been shown to ablate antibody dependent-, and complement dependent-cytotoxicity. These mutations can enhance the half-life of the protein and confer a favorable pharmacokinetic profile when administered in vivo. This Toso-Fc construct, as well as an empty vector control, were transfected into $3 \times 10^8$ 293 F cells in 400 ml of serum free media cells using the Freestyle expression system. Two days later, the supernatant was collected and the cells were resuspended in a further 400 ml of media. After 2 more the days of culture, the second supernatant was collected and combined with the first supernatant. The secretion of Toso-Fc soluble receptor was confirmed using ELISA (FIG. 8B), purified by Protein G chromatography, and eluted with 100 mM Glycine pH 2.3. 1 ml eluant fractions were collected into 60 µl of neutralization buffer (1 M Tris pH 9.5) and confirmed by western blot with an antibody directed at the Fc region (FIG. 8Ci) and Coomassie Blue staining (FIG. 8Cii).

Figure 8D:
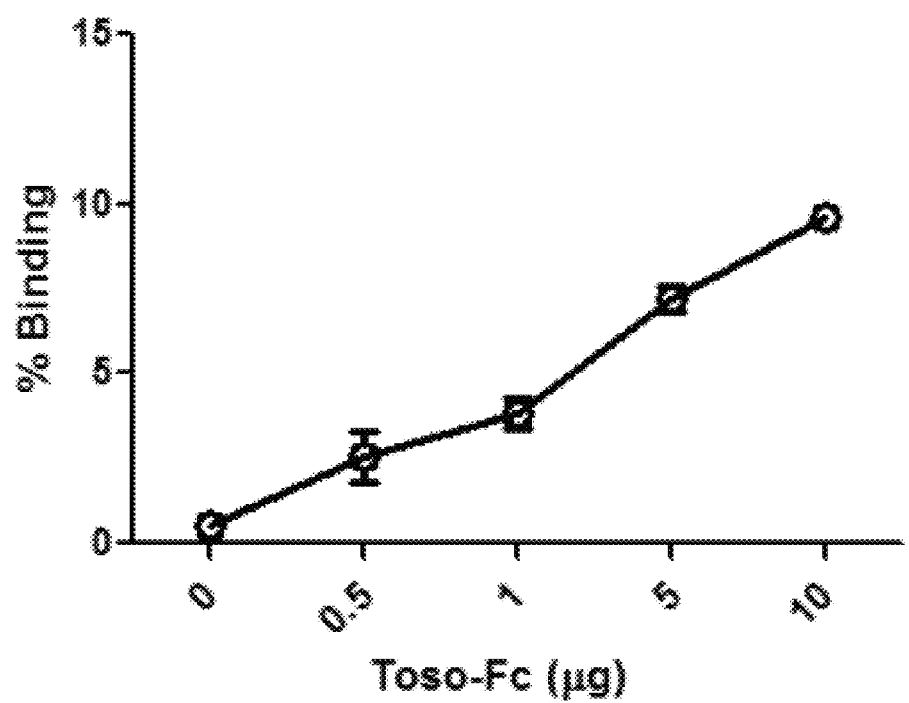
FIG. 8D shows binding data of the Toso soluble receptor to splenocytes.
Figures 1, 8E:
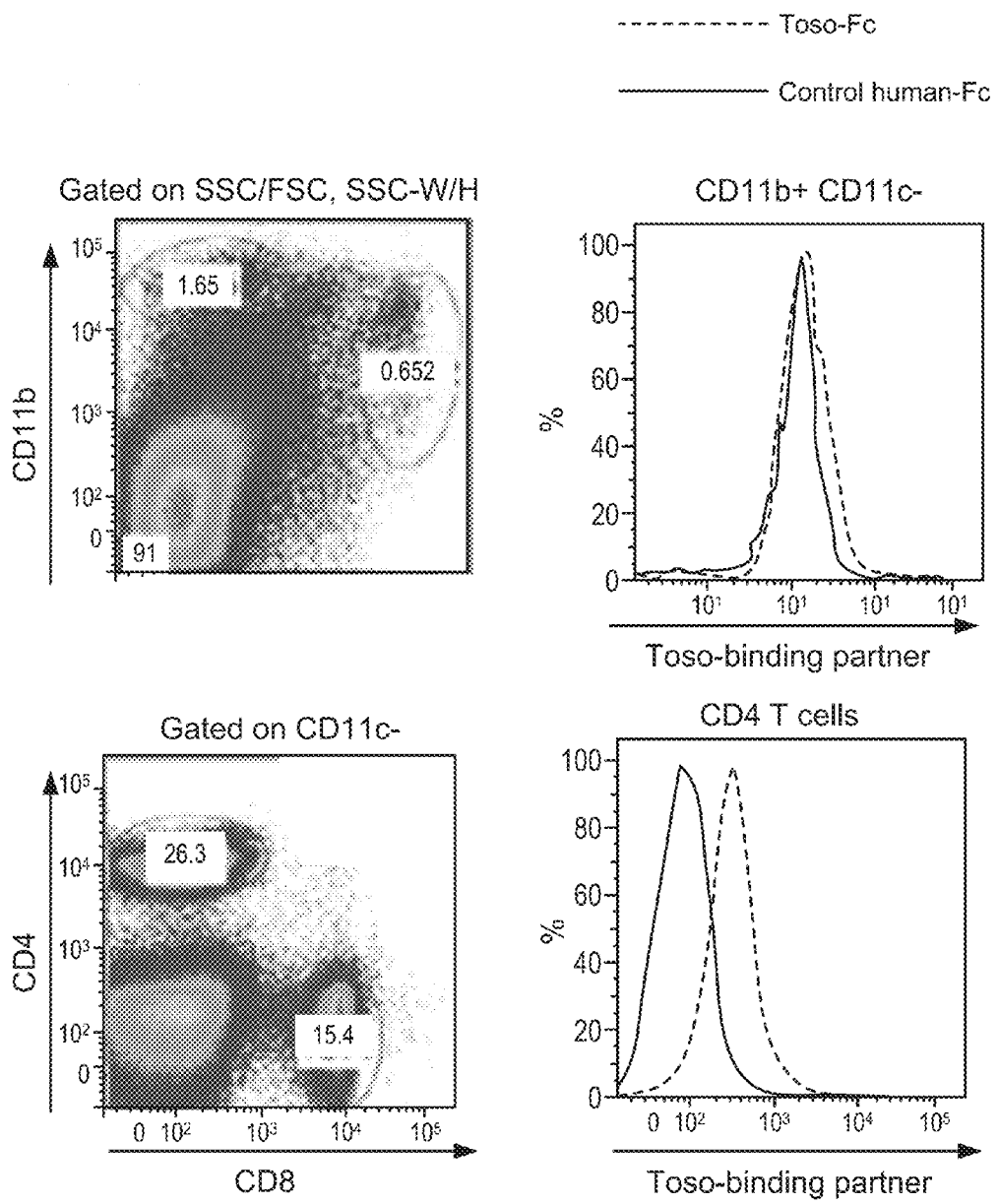
Figures 2, 8E:
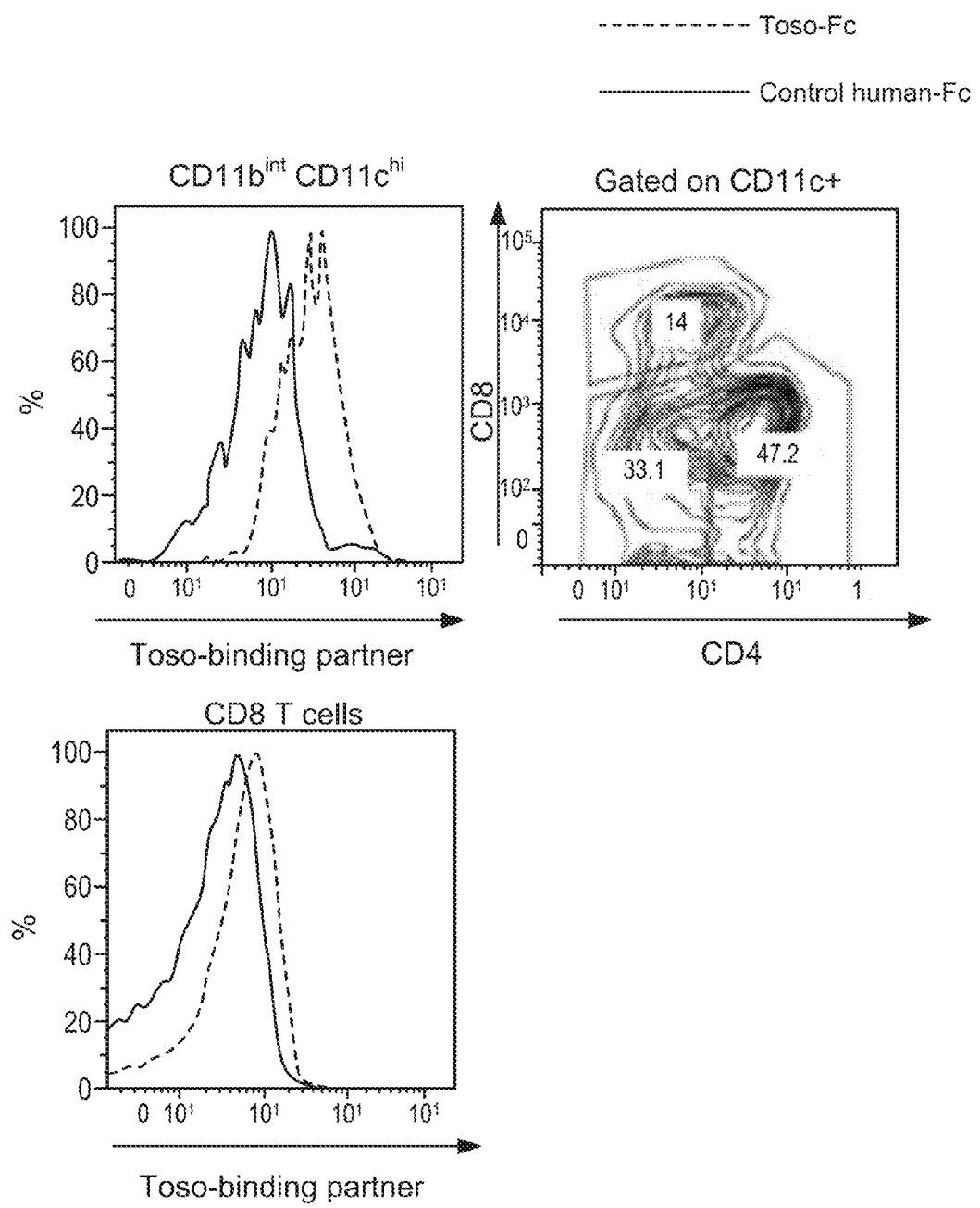
Figures 3, 8E:
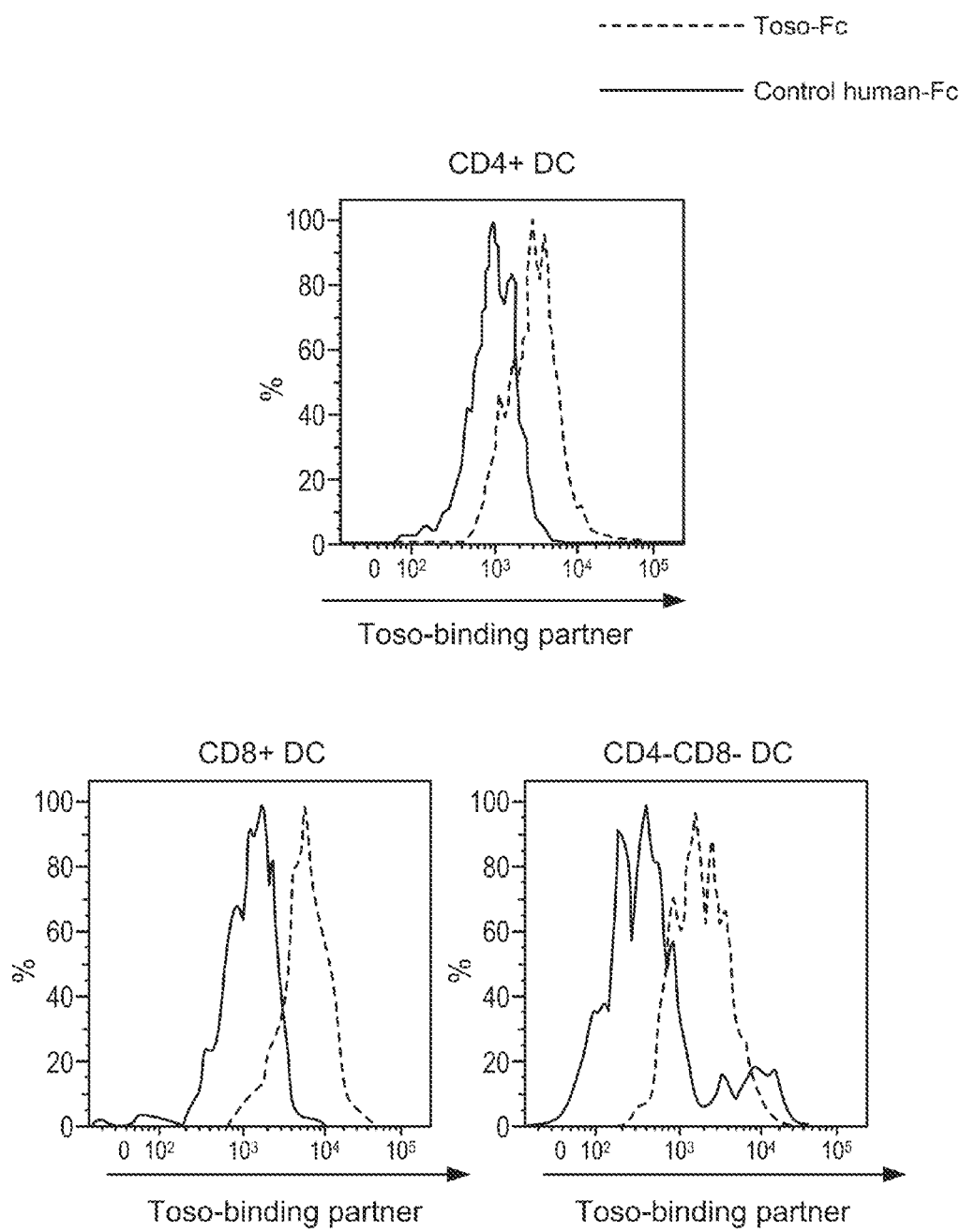
Figures 4, 8E:
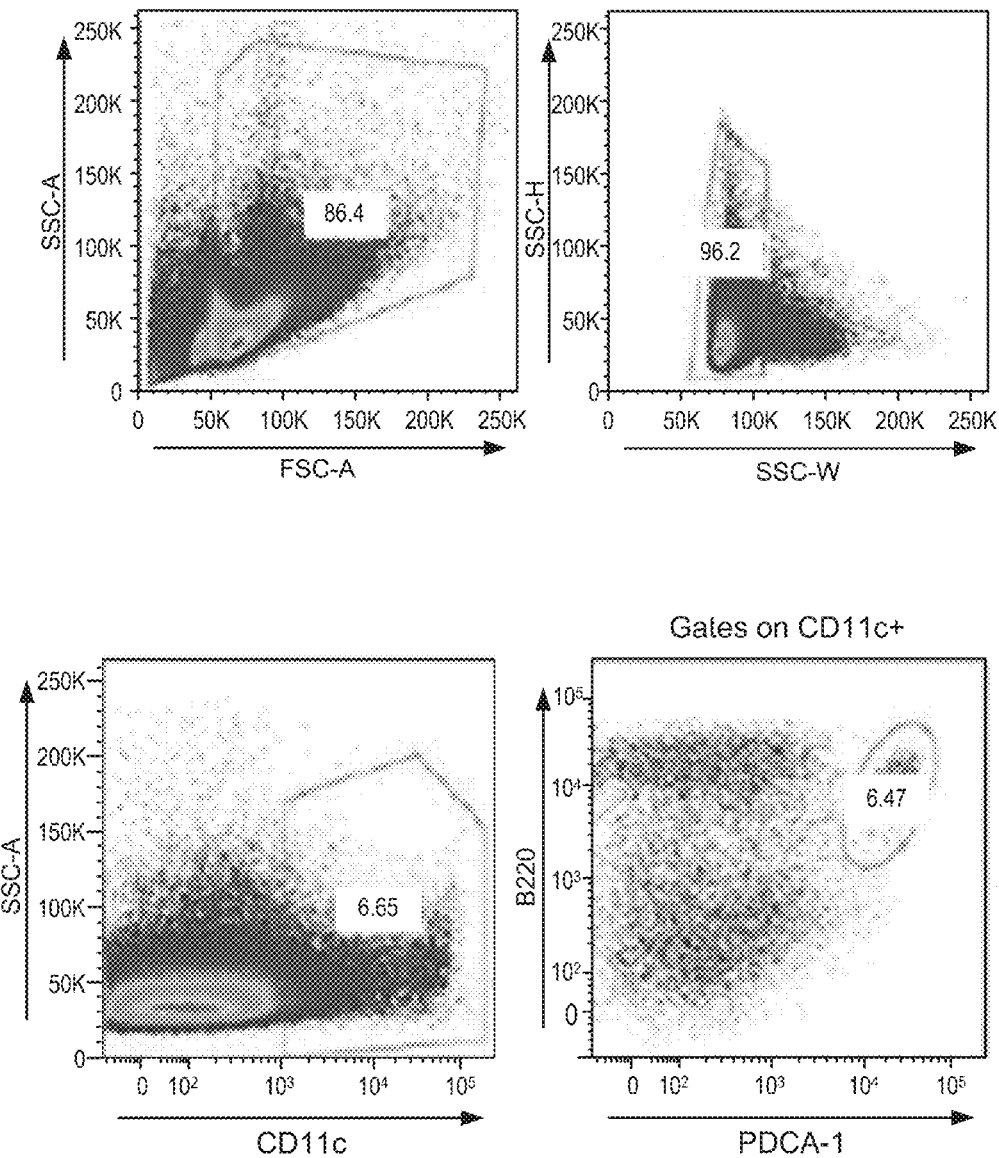
Figures 5, 8E:
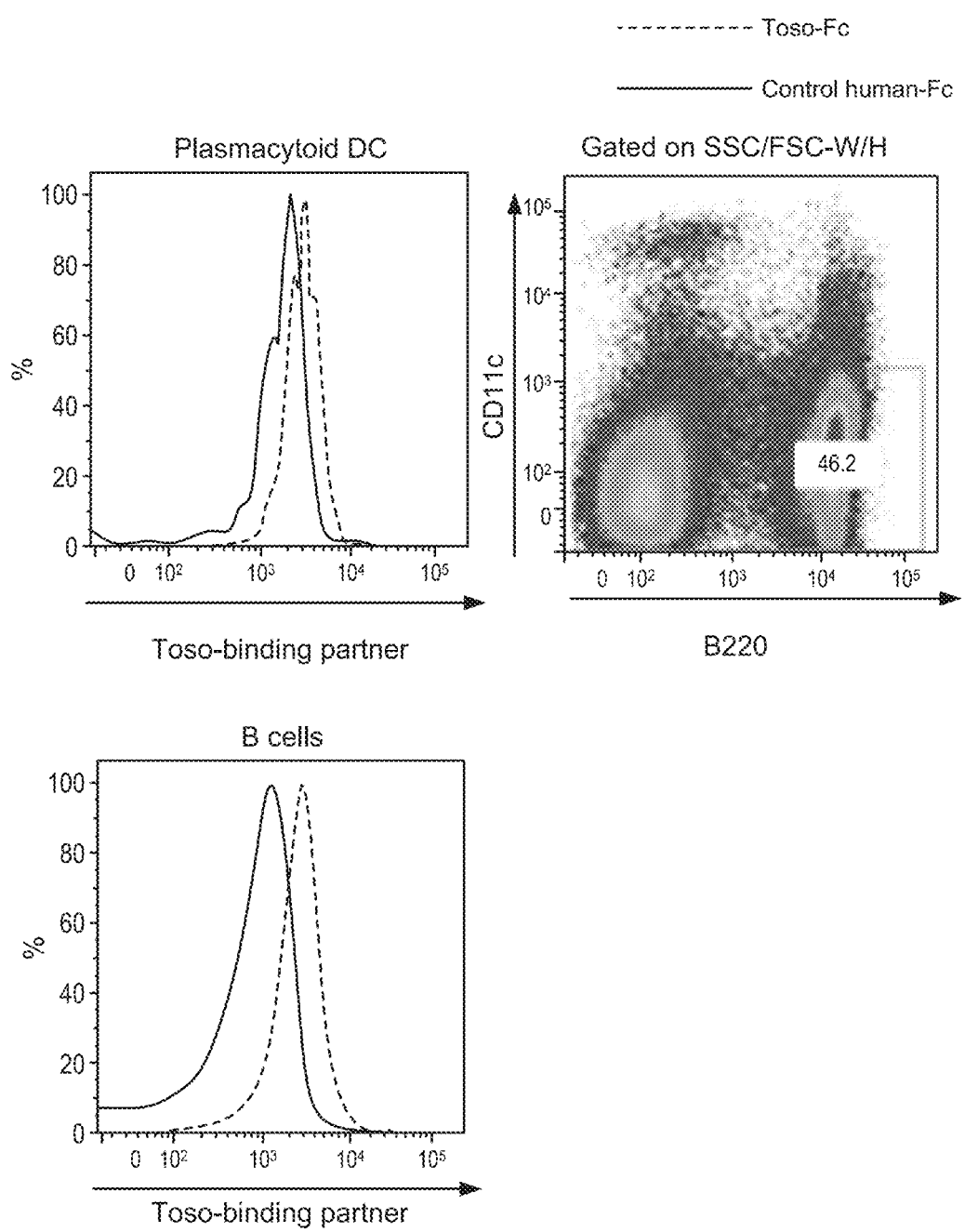
Figure 8F:
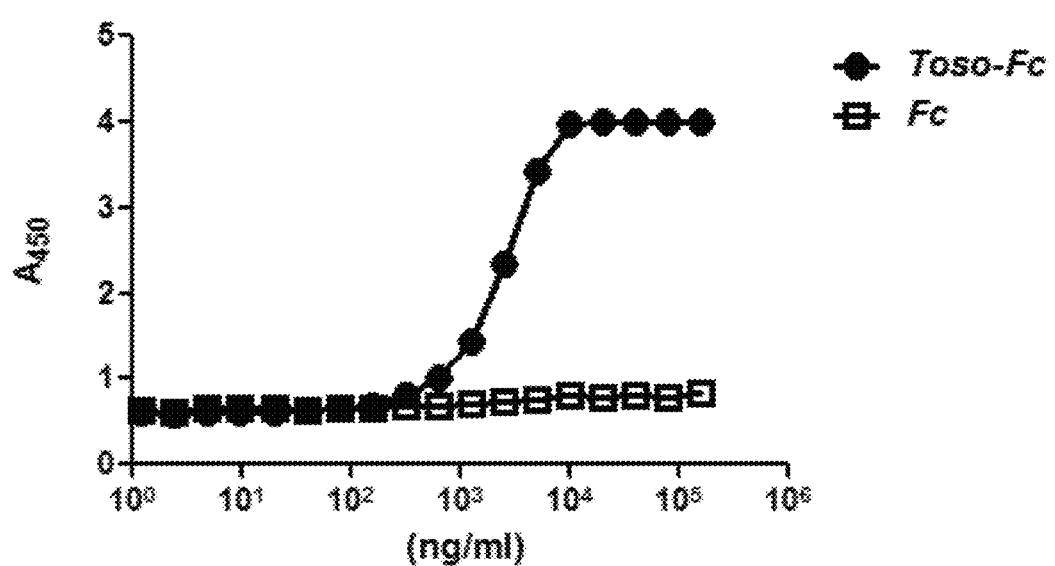
FIG. 8F shows ELISA results of Toso-Fc binding to platebound human IgM.
Figure 8G:
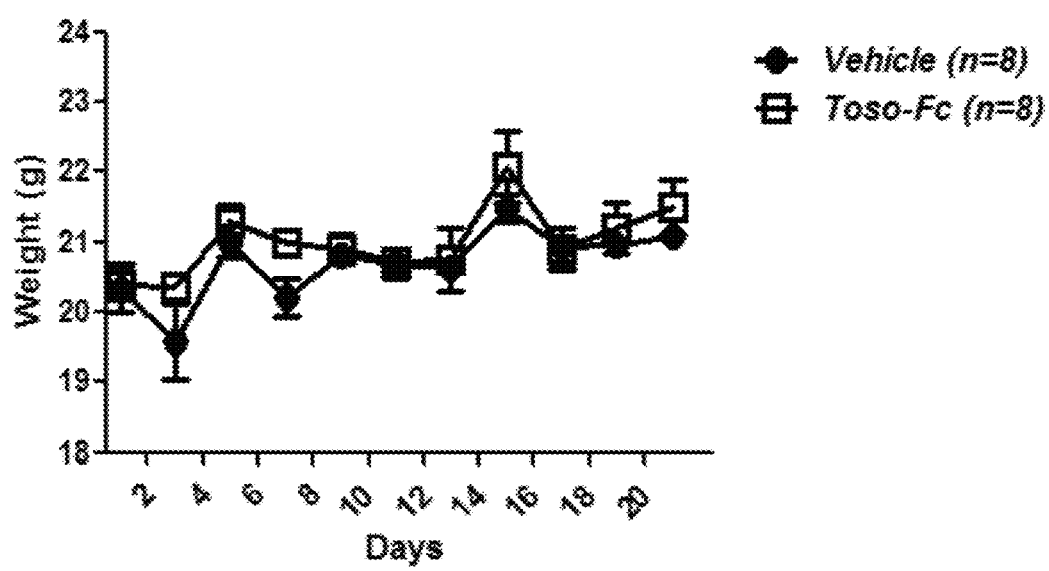
FIG. 8G shows normal weight gain in mouse treated with 50 μg daily of Toso-Fc.

Binding of the soluble receptor was tested on murine splenocytes. Approximately 106 cells were incubated with indicated amounts of Toso-Fc in 100 µl of FACS staining buffer (PBS+1% BSA+0.05% $NaN_3$) for 2 hours on ice. Cells were washed in FACS buffer and incubated with a FITC conjugated anti-human FC g F(ab')2 fragment for 30 minutes on ice, and acquired on a FACS Canto flow cytometer. Approximately 10% of splenocytes bound to the soluble receptor at 10 µg (FIG. 8D). A purified Fc protein alone did not show significant binding to splenocytes, suggesting that Toso-Fc binding was specific. A further detailed analysis indicated that Toso-Fc bound most significantly to CD11c+MHChi mature dendritic cells or CD11c+B220+ plasmacytoid DCs in the spleen (FIG. 8E). These data illustrate that the Toso-Fc soluble receptor is functional, and that the ligand for Toso may be expressed on mature dendritic cells.

Figure 9A:
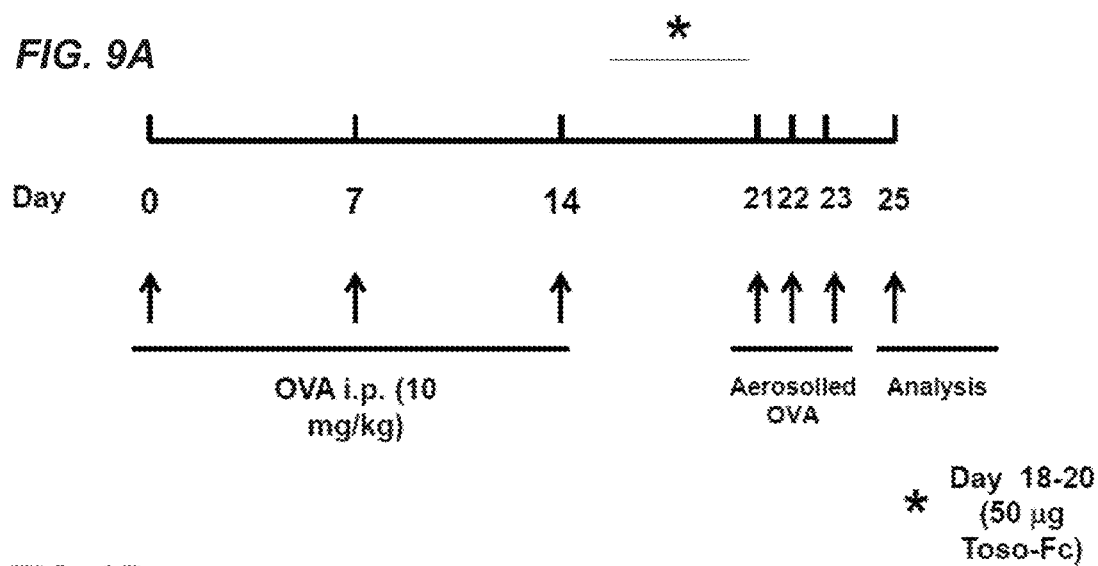
FIG. 9A is a schematic illustration of the treatment protocol for the murine model of OVA induced asthma.
Figure 9B:
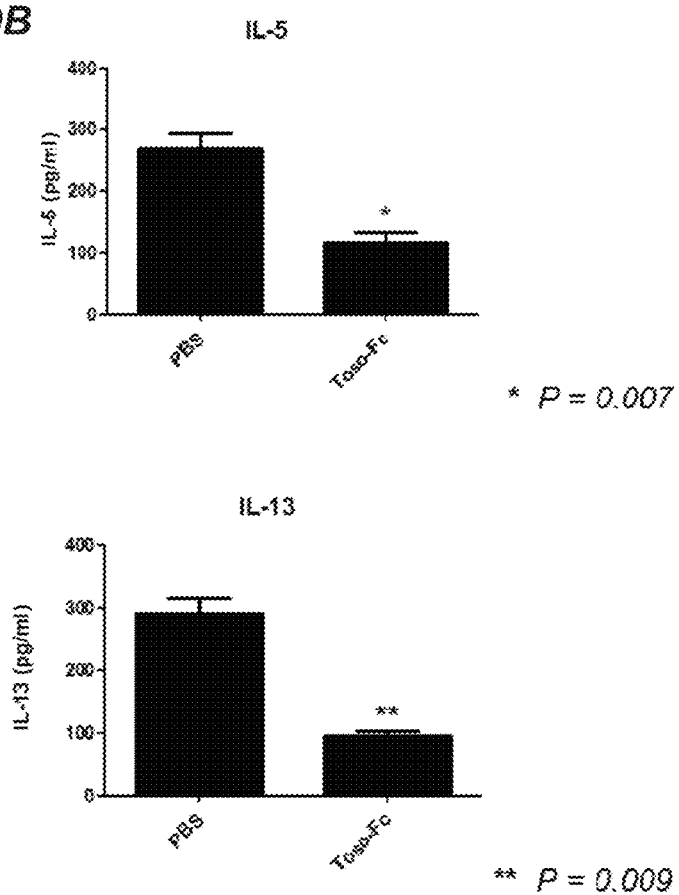
FIG. 9B shows data on Th2 cytokines in the BALF and FIG. 9C shows cellularity data in the BALF, which are both measurements of the severity of the disease.
Figure 9C:
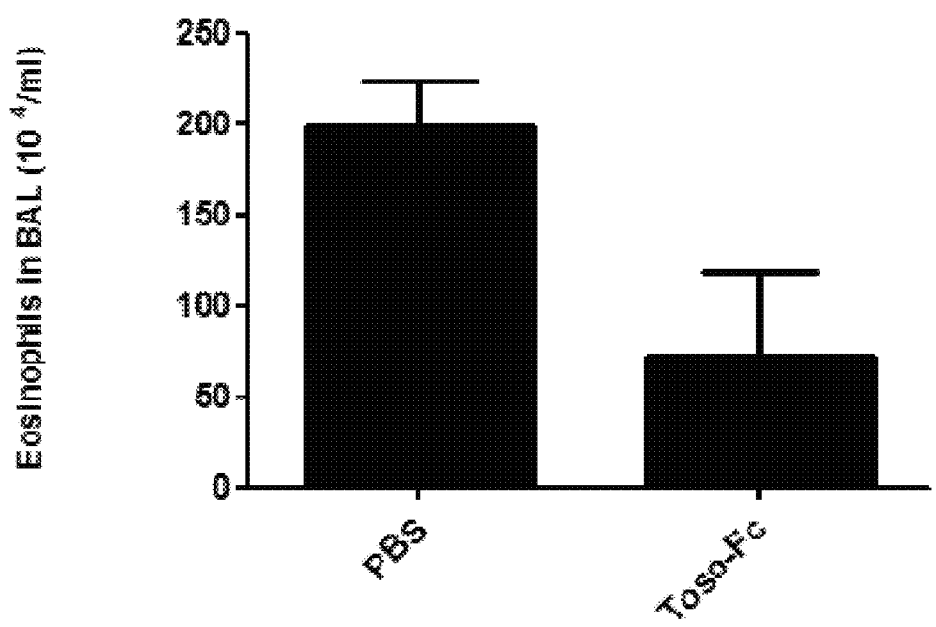

The therapeutic utility of Toso-Fc administration was assessed in a murine model of OVA induced asthma. Disease was elicited as described above with slight modifications. Female BALB/c mice were treated as described except that 50 µg of Toso-Fc was administered intraperitoneally for 3 consecutive days before aerosolled OVA challenge (FIG. 9A). Severity of disease was assessed by evaluating Th2 cytokines in the BALF (FIG. 9B), cellularity in the BALF (FIG. 9C). Pretreatment with Toso-Fc significantly abrogated disease metrics, suggesting that administration of Toso-Fc may be a useful treatment paradigm in the management of asthma.

Example 7

Toso is a Potential Target for Treatment of Multiple Sclerosis

Experimental Autoimmune Encephalitis (EAE) is a useful mouse model for human MS. This system involves the antigen dependent activation of CD4+TH1/TH17 cells, and perivascular accumulation of monocytic cells leading to demyelination, and hind limb paralysis. In the C57BL/6 background, EAE is deemed chronic progressive, as disease increases with time and is elicited through the injection of Myelin Oligodendrocyte Glycoprotein peptide, MOG35-55, with Pertussis toxin in Complete Freund's Adjuvant. Disease severity is scored from 0 to 5 daily for approximately 1 month (where 0=no sign of disease, 1=limp tail or hind limb weakness but not both, 2=limp tail and hind limb weakness, 3=partial hind limb paralysis, 4=complete hind limb paralysis, 5=moribund state or death by EAE).

Figure 6:
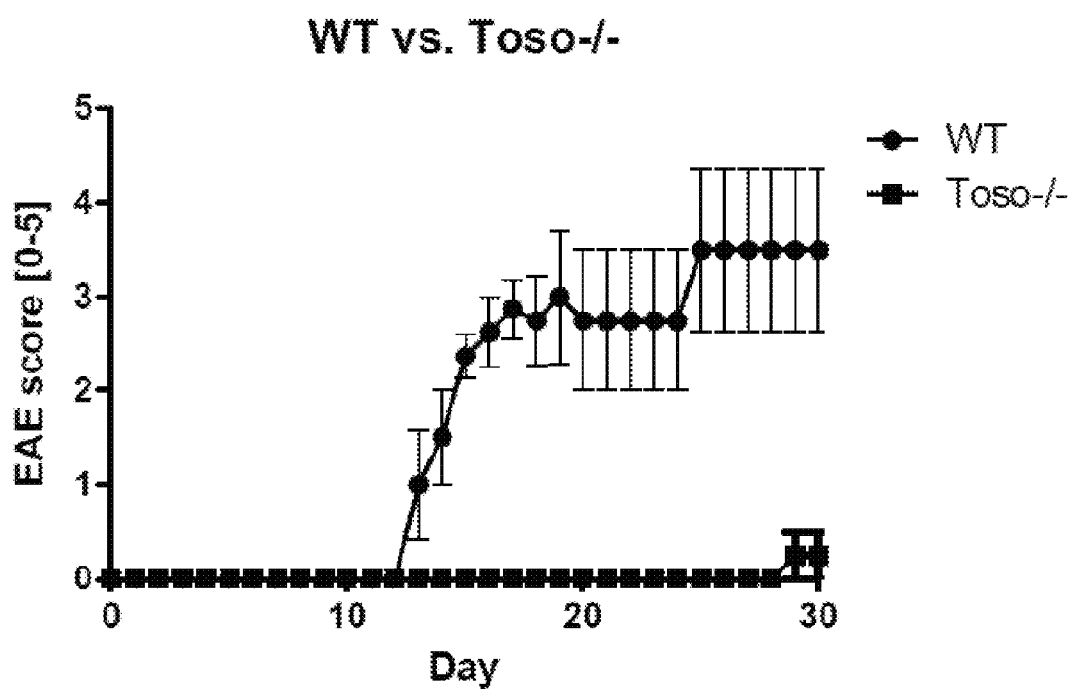
FIG. 6 shows EAE scores in a MOG-induced model in wildtype and Toso$^{-/-}$ mice.

In the aforementioned MOG-induced model, Toso−/− mice were markedly protected from the onset of EAE compared to wild type controls (FIG. 6). These data suggest that blocking Toso function may represent a novel treatment strategy for MS.

Example 8

Treatment with Toso-Fc Delays the Onset of EAE

Figure 23:
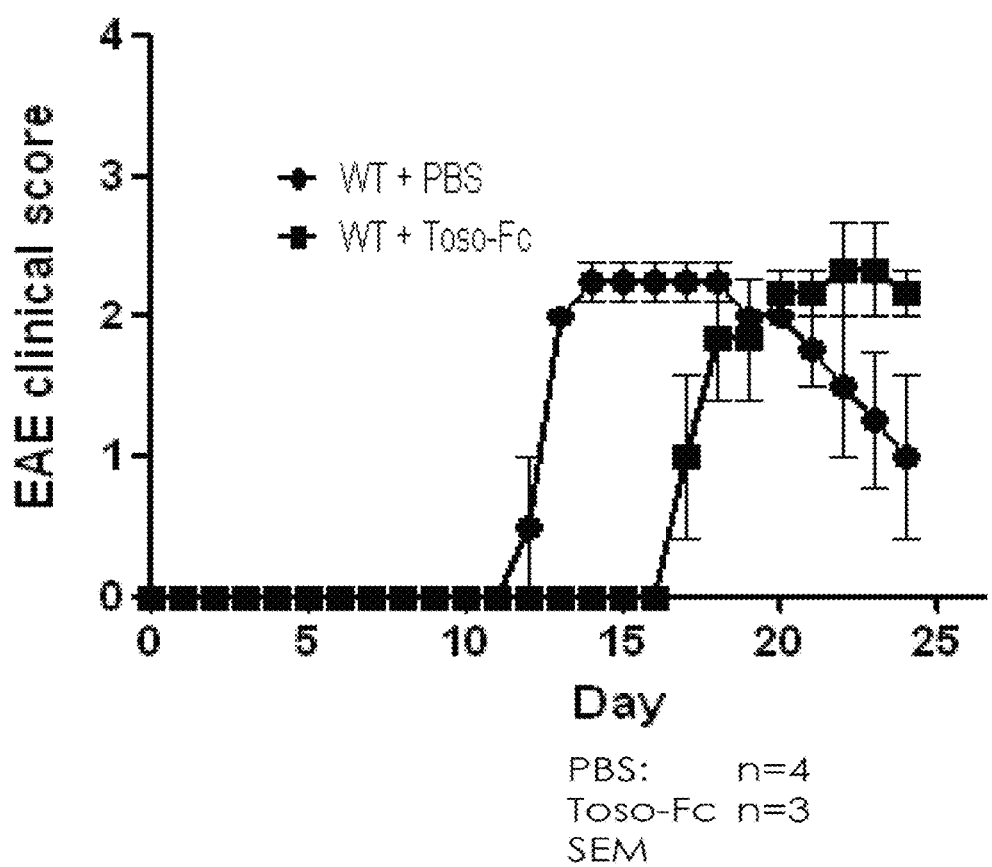
FIG. 23 shows EAE clinical scores in mice treated with PBS (closed circle) compared to mice treated with soluble Toso protein (Toso-Fc—closed square).

This example demonstrates that treatment with Toso-Fc (SEQ ID NO: 5) delays the onset of EAE. As discussed above, the EAE mouse model is a useful model for human MS. For the experiments pictured in FIG. 23A, C57BL/6 mice were pretreated with Toso-Fc before immunization with the disease-inducing MOG peptide. After immunization, mice were treated with 50 µg Toso-Fc (or PBS for the control mice) intraperitoneally three times per week for 30 days. As shown in FIG. 23B, Toso-Fc delayed the progression of EAE, showing a modifying effect of Toso-Fc in Multiple Sclerosis.

Example 9

Toso Diminishes Innate Antibacterial Immune Response

This example demonstrates that granulocytes are activated early in Toso deficient mice after bacterial infection and are essential for the control of pathogens. Toso deficient granulocytes demonstrated enhanced expression of CD11 b and CD18 and displayed a lowered activation threshold. In line with these results, Toso deficient granulocytes showed reduced effector function at the sites of inflammation in peripheral tissue. As a result of the altered granulocyte function, Toso deficient mice failed to clear systemic listeria infection leading to fast death of Toso deficient mice. Therefore, Toso influences activation threshold and effector function of granulocytes, and thus critically diminishes innate anti bacterial immune response.

Materials and Methods

Mice:

Short sequences were obtained by sequencing the library isolated genomic DNA fragments using a series of oligomers derived from the mouse Toso cDNA sequence. A 6.5 kbp fragment was isolated from the 5' end using BgIII restriction digestion enzyme and was used as a long arm for the knockout construct. A 650 bp short arm was produced by polymerase chain reaction using oligomers derived from the sequence of the 3' end of the gene (5' GTGAATACGT-GAGCTTGGGCTACC 3' SEQ ID NO: 26 and 5'CAAGT-GATGG GGGATTACAGTGAA3' SEQ ID NO: 27). The long and short arm were ligated on either end of a Neomycin resistance cassette in the same orientation as the Toso translation sense. The site specific insertion of this knockout construct into embryonic stem (ES) cell genomic DNA was first screened by polymerase chain reaction (PCR) using primers designed in the 3' end of Neo and in the genomic DNA flanking region downstream of the 3' end of the short arm. The mice were screened using three primers. A common primer (5' TGTTTAATATGATGTGTCAGGCTG 3' SEQ ID NO: 28) was located in the short arm region and the two other primers were from either the 3' region of Neo (5' AGGGCCAGCTCATTCCTCCCACTCAT 3' SEQ ID NO: 29) or the 3' region of DNA that was excised by the knockout construct (5' AACTCTGCCCCTGCTCCTTCATTTCC 3' SEQ ID NO: 30). In doing so the band obtained from the rearranged allele was of 400 bp and that of the native gene was 450 bp. D3 ES cells were electroporated with knockout construct and grown in the presence of 300 µg/ml G418. Positive ES clones were then injected into E3.5 C57/BL6 derived blastocysts Chimeric off springs were screened for the presence of the rearranged allele and backcrossed to C57BL/6 background. CD11b$^{-/-}$ mice were derived from Jackson on a C57BL/6 background.

Bone Marrow Chimeric Mice:

Mice were lethally irradiated with 1050 rad and reconstituted either with $10^7$ CD45.1 WT bone marrow cells, or $10^7$ CD45.2 Toso$^{-/-}$ bone marrow cells or $5 \times 10^6$ CD45.1 WT bone marrow cells plus $5 \times 10^6$ CD45.2 Toso$^{-/-}$ bone marrow cells. All mice used in this study were maintained on the C57BL/6 genetic background. All experiments were performed in single ventilated cages.

Listeria Infection:

Listeria was grown in heart infusion agar. If not differently indicated, mice were infected intravenously with $2 \times 10^4$ CFU.

Granulocyte Activation and FACS Analysis after Cytokine Stimulation:

FACS staining and analysis were performed as described (Lang, P. A., et al. Aggravation of viral hepatitis by platelet-derived serotonin. Nat Med 14, 756-761 (2008), which is hereby incorporated by reference in its entirety for all purposes and in particular for all teachings related to FACS staining and analysis). Recombinant mouse TNF-α was from R+D systems, LPS was from Sigma and GM-CSF was obtained from X63O cell supernatants. fMLP from Sigma was used at the indicated concentrations. For activation studies 10 µl blood was incubated in 100 µl medium containing different cytokines in addition to anti Gr1 (eBiosciences), Dihydrorhdamin (Alexis) and CD11 b (eBiosciences, if indicated). After 30 minutes or 45 minutes of incubation (at 37° C. if not differently indicated) granulocytes were fixed and red cells were lysed using erythrocyte lysis buffer (BD Biociences). For nave expression of CD11a, CD11 b and CD18 blood was fixed with 2% Formalin for 10 minutes, and then stained with anti Gr1 and the according antibodies at 4° C. Toso antibody was generated according to Nguyen, et al., (Blood, 2011, Jul. 21, 118(3):598-608).

For priming studies granulocytes were incubated with different cytokines for 30 minutes followed by 15 minutes of fMLP incubation.

Histology:

Histological analysis was performed on snap frozen or formalin fixed tissue as described in Lang, K. S., et al. Immunoprivileged status of the liver is controlled by Toll-like receptor 3 signaling. J Clin Invest 116, 2456-2463 (2006), which is hereby incorporated by reference in its entirety for all purposes and in particular for all teachings related to histological analysis.

MPO ELISA:

MPO ELISA was derived from Hycult biotech and performed according to the manufacturer's instructions.

mRNA Gene-Profiling by Quantitative RT-PCR:

RNA extraction and cDNA synthesis was performed using Trizol. Gene expression analysis of was performed using Toso (Faim3) kit Mm01302388_m1 from Applied Biosystems. For analysis, the expression levels of all target genes were normalized against 18sRNA (ΔCt). Gene expression values are expressed as ΔCt.

Statistical Analysis:

Data are expressed as mean±S.E.M. Statistically significant differences between two different groups were analyzed using Student's t-test. If not differently mentioned unpaired two way. Analysis including several groups were performed using one-way ANOVA with additional Bonferroni or Dunnett test. Statistically significant differences between experimental groups over multiple timepoints were calculated using two-way ANOVA (repeated measurements). p values<0.05 were considered as statistically significant.

Figure 12A:
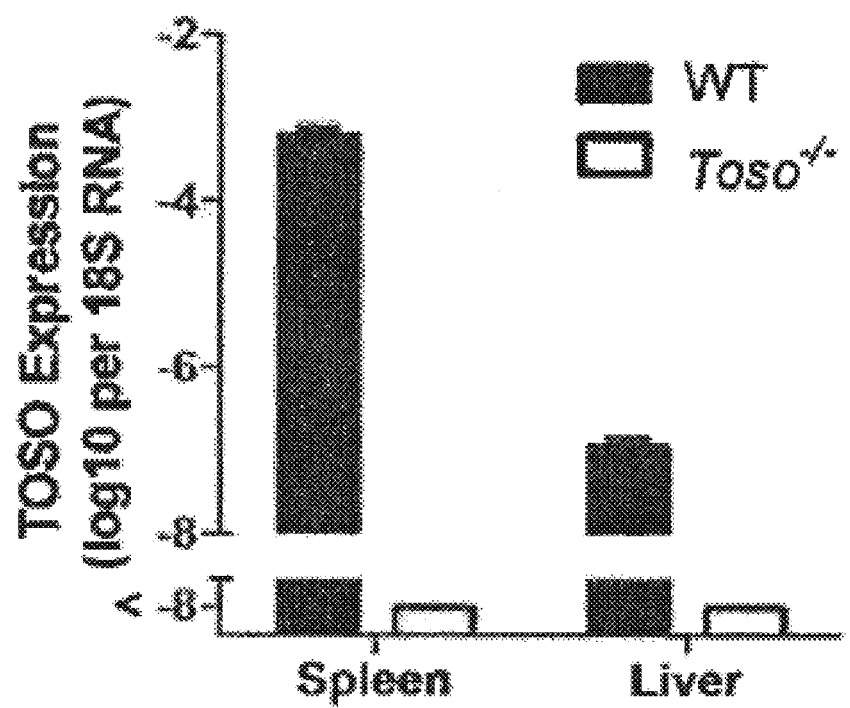
FIG. 12A, FIG. 12B, FIG. 12C, FIG. 12D, FIG. 12E, FIG. 12F and FIG. G show TOSO expression on granulocytes.
Figure 12B:
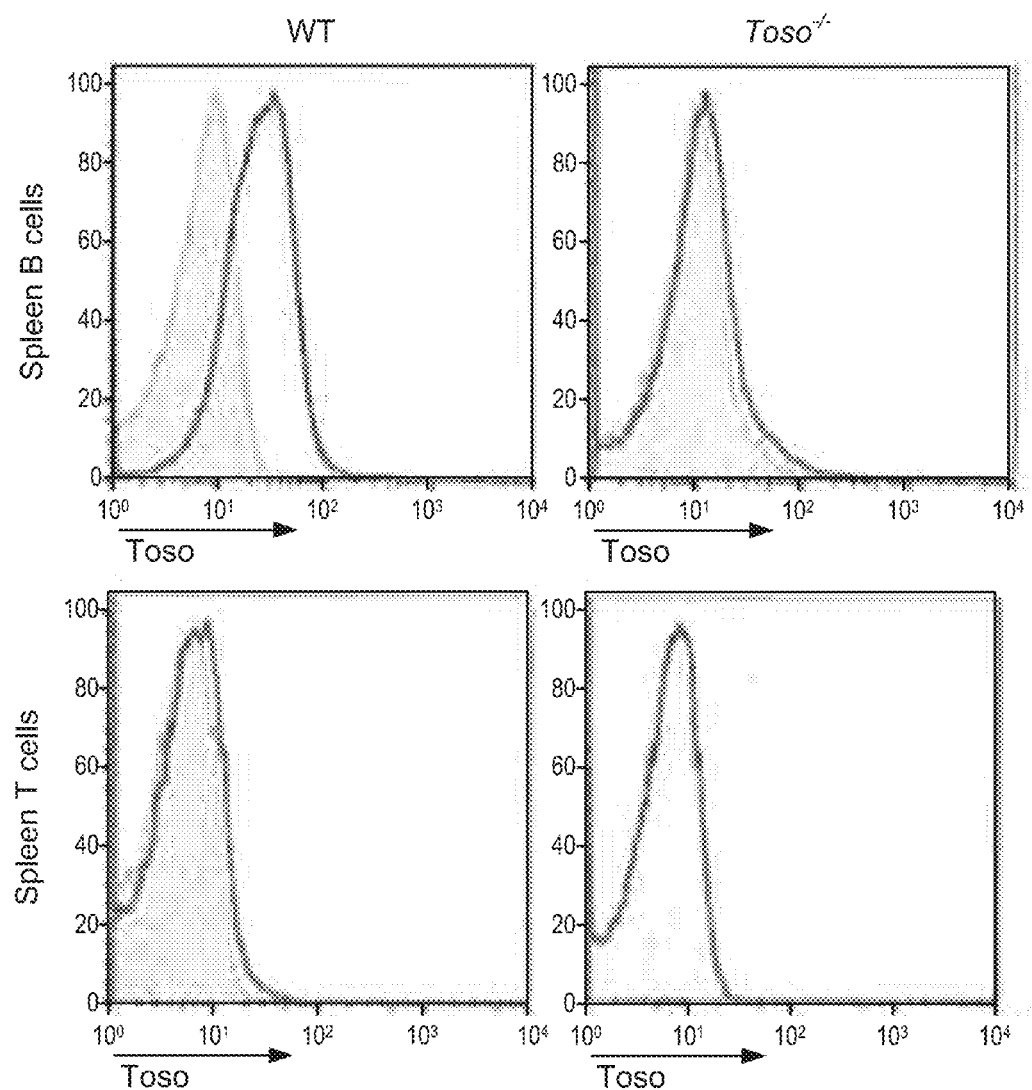
Figure 12C:
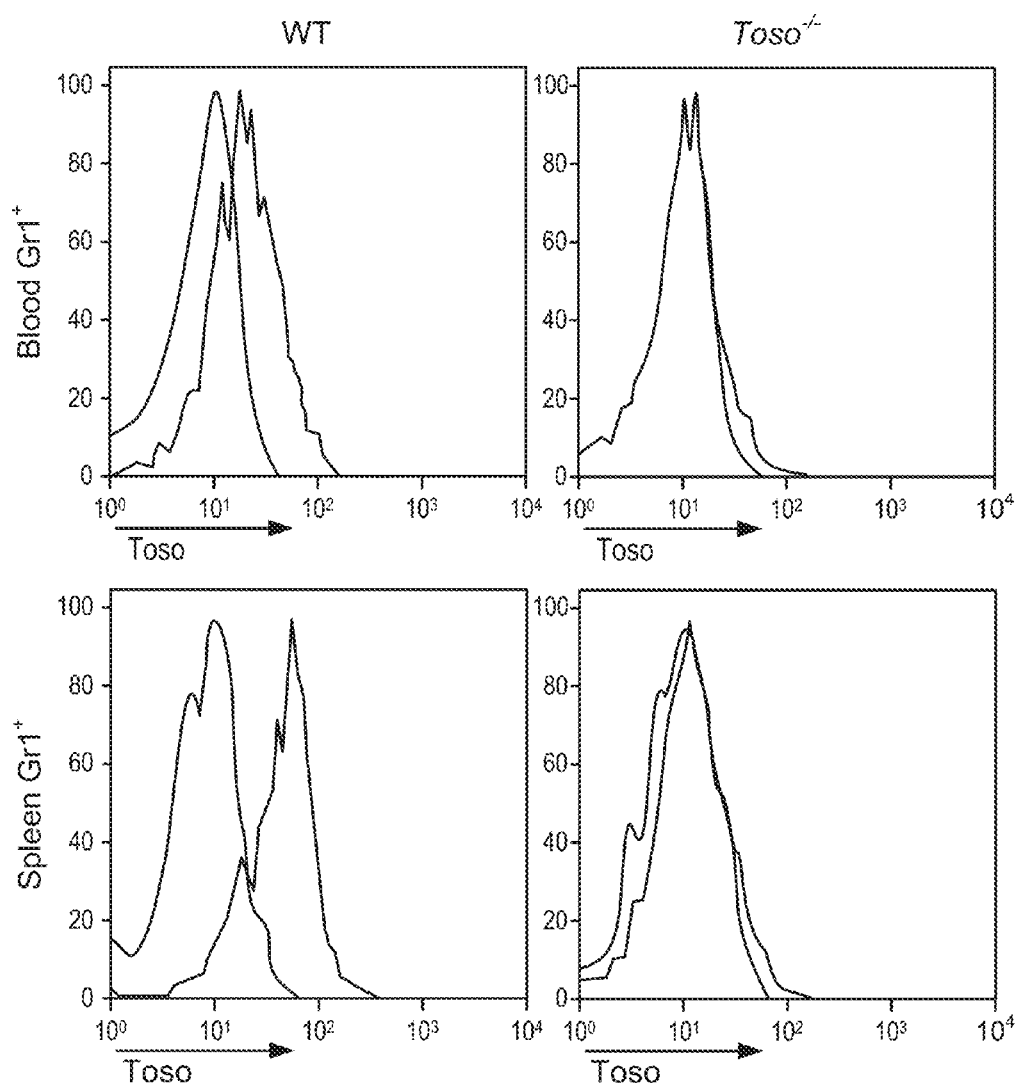
Figure 12D:
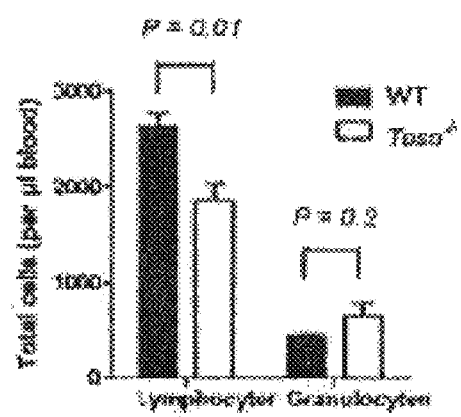
Figure 12E:
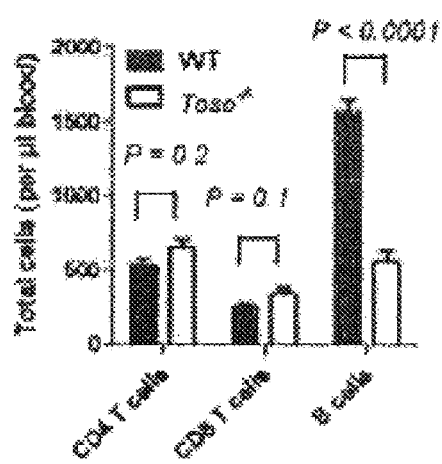
Figure 12F:
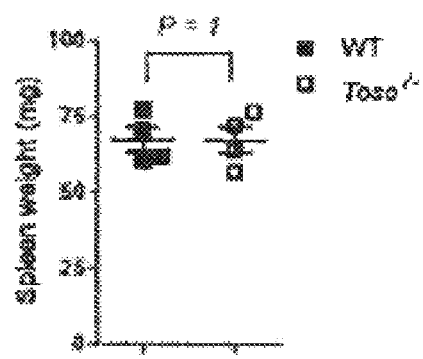
Figure 12G:
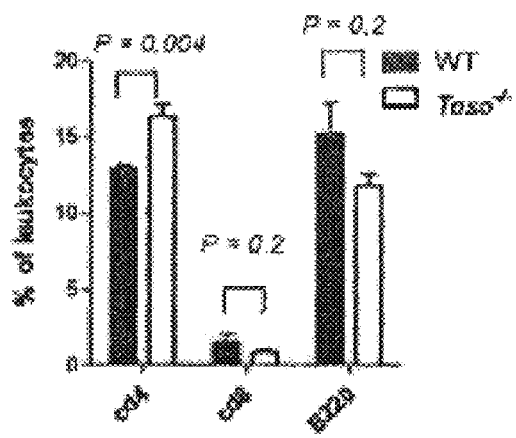
FIG. 12G: Spleen lymphocytes were analyzed for CD4 T cells (CD3$^+$ CD8$^-$ cells) CD8 T cells (CD3$^+$ CD8$^+$ cells) and B cells (B220$^+$ cells, n=4).

TOSO is Expressed on Granulocytes but is not Essential for Leukocyte Differentiation To analyze the functional relevance of Toso in vivo the inventors generated a Toso deficient mouse as described in material and methods. Toso deficient mice were backcrossed to C57BL/6 background and then analyzed for expression of Toso RNA. RT-PCR analysis from Toso$^{-/-}$ mice showed lack of Toso, suggesting that indeed Toso was not expressed in Toso$^{-/-}$ mice (FIG. 12a). Next Toso protein was analyzed on lymphocytes using a Toso specific antibody. It was found that naïve B cells but not T cells expressed Toso (FIG. 12b) in keeping with published literature. Next, the inventors analyzed expression of Toso on granulocytes. The inventors found that granulocytes both in blood and spleen expressed Toso on the cell surface (FIG. 12c). To analyze if Toso influenced lymphocyte or granulocyte development, the inventors analyzed these cell populations in peripheral blood of Toso$^{-/-}$ mice. Toso$^{-/-}$ mice did not show any striking difference in the blood granulocytes (FIG. 12d). There was a slightly significant reduction of blood lymphocyte numbers in Toso deficient mice which was attributed to a reduced B cell number (FIGS. 12d&e). The spleen size of Toso$^{-/-}$ mice was normal and spleen lymphocytes showed a normal distribution (FIGS. 12f&g) suggesting that there is no major role of Toso on the development of immune cells.

3. Threshold for Activation is Reduced in Granulocytes of TOSO Deficient Mice

Figure 13A:
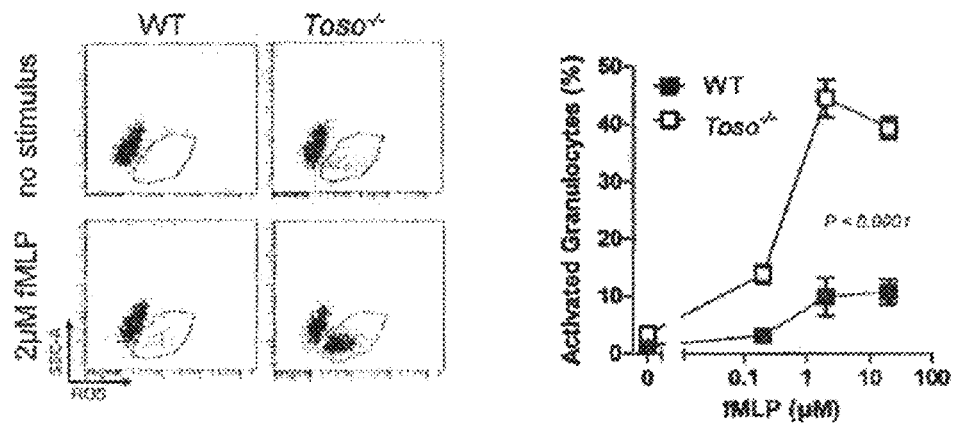
FIG. 13A, FIG. 13B, FIG. 13C, FIG. 13D, FIG. 13E and FIG. 13F show that threshold for activation is lowered in granulocytes of TOSO deficient mice.

Granulocytes from Toso$^{-/-}$ and wildtype mice were activated with the granulocyte activator N-Formylmethionyl-Lencyl-Phenylalanine (fMLP). fMLP activates the fMLP receptor on granulocytes, which mimics pathogen contact. In pre-activated granulocytes contact with fMLP leads to strong production of reactive oxygen species (ROS) and degranulation. In contrast granulocytes which are not pre-activated by cytokines show limited response to fMLP. Only 10% of wildtype granulocytes were activated upon treatment with fMLP when analyzed by production of ROS and degranulation (FIG. 13a). In contrast, treatment with fMLP activated 50% of Toso$^{-/-}$ granulocytes (FIG. 13a).

Figure 13B:
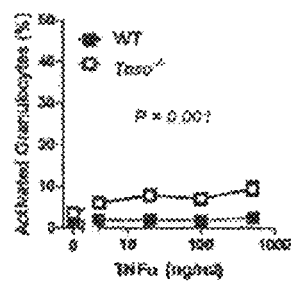
Figure 13C:
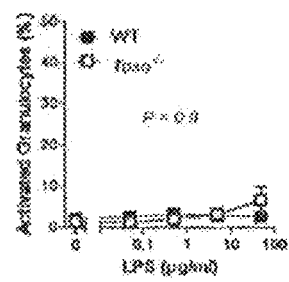
Figure 13D:
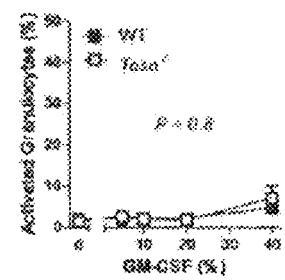
Figure 13E:
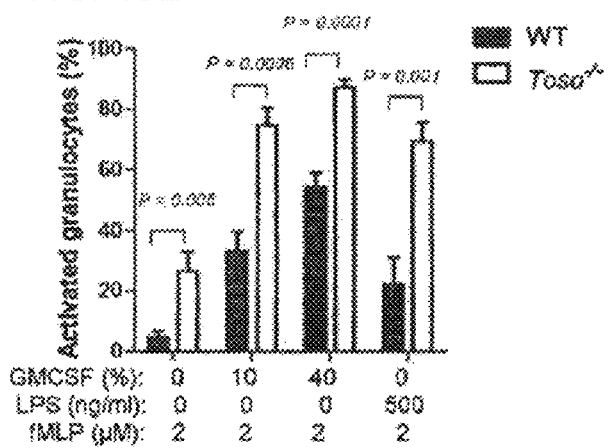

Next ROS production and degranulation of Toso$^{-/-}$ granulocytes was analyzed following treatment with TNF-α, which usually only primes granulocytes, but does not lead to ROS production. Treatment with TNF-α led to virtually absent ROS production in WT granulocytes (FIG. 13b). In contrast, Toso$^{-/-}$ granulocytes showed significant ROS producing/de-granulated granulocytes after TNF-α treatment, suggesting that Toso influences the threshold of granulocyte activation (FIG. 13b). Treatment with LPS and GM-CSF, which are also known to prime granulocytes did not activate ROS neither in wildtype nor Toso$^{-/-}$ granulocytes (FIGS. 13c&d). These results show that Toso$^{-/-}$ granulocytes had a lowered activation threshold for both fMLP and TNF-α. Co-treatment with GM-CSF or LPS together with fMLP increased the percentage of ROS producing wildtype granulocytes by 10 fold in WT granulocytes (FIG. 13e). The percentage of ROS producing granulocytes was also increased in either LPS or GM-CSF primed fMLP co-treated Toso$^{-/-}$ granulocytes (FIG. 13e). These data show that Toso$^{-/-}$ granulocytes displayed a lowered activation threshold also in the setting of granulocyte priming with GM-CSF or LPS. This suggests that Toso$^{-/-}$ granulocytes had a reduced activation threshold in general.

Figure 13F:
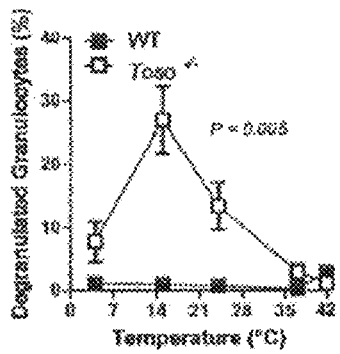
Figure 17:
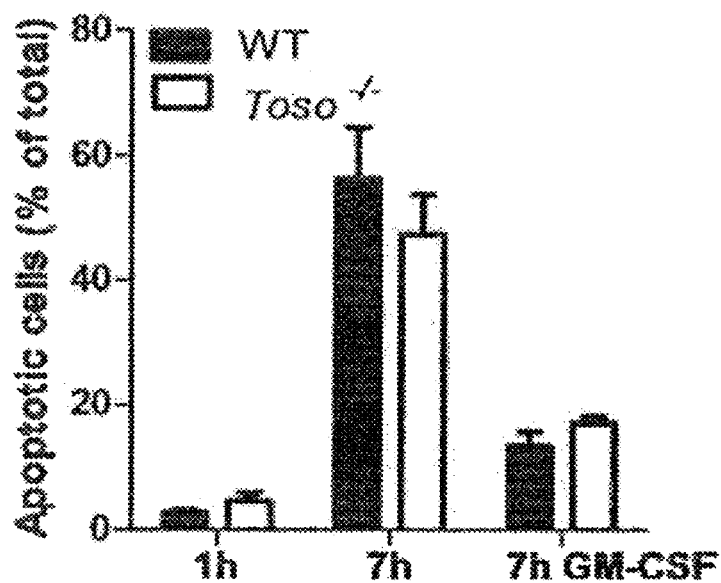
FIG. 17 shows apoptosis in Toso$^{-/-}$ granulocytes. Blood from Toso$^{-/-}$ was incubated at 37° C. with and without GM-CSF (10%). Apoptosis was measured with Annexin V and 7AAD after one and seven hours (n=4).

Cellular stress can activate granulocytes, which might significantly contribute to (auto)inflammatory disease. To analyze if Toso$^{-/-}$ granulocytes are more prone to such activation, wildtype (WT) and Toso$^{-/-}$ granulocytes were incubated at different temperatures. Temperature reduction induced degranulation in 30% of Toso$^{-/-}$ granulocytes, a condition where wildtype granulocytes did not show any response (FIG. 13f). The difference in the activation threshold could be explained by a difference in the life span between WT and Toso$^{-/-}$ granulocytes. Granulocytes usually have a very limited life span which is underlined by spontaneous apoptosis within 24 hours after in vitro culture. Granulocyte activation is usually coupled to prolonged lifespan and decreased apoptosis. However, there was no difference in spontaneous apoptosis between Toso$^{-/-}$ and WT granulocytes (FIG. 17). Treatment with GM-CSF reduced apoptosis in granulocytes a process which did not depend on Toso (FIG. 17). The data demonstrate that expression of Toso protein kept granulocytes in a resting non-activated state when encountering inflammatory or stress signals.

Activation Threshold in Granulocytes is Regulated Intrinsically

Figure 14A:
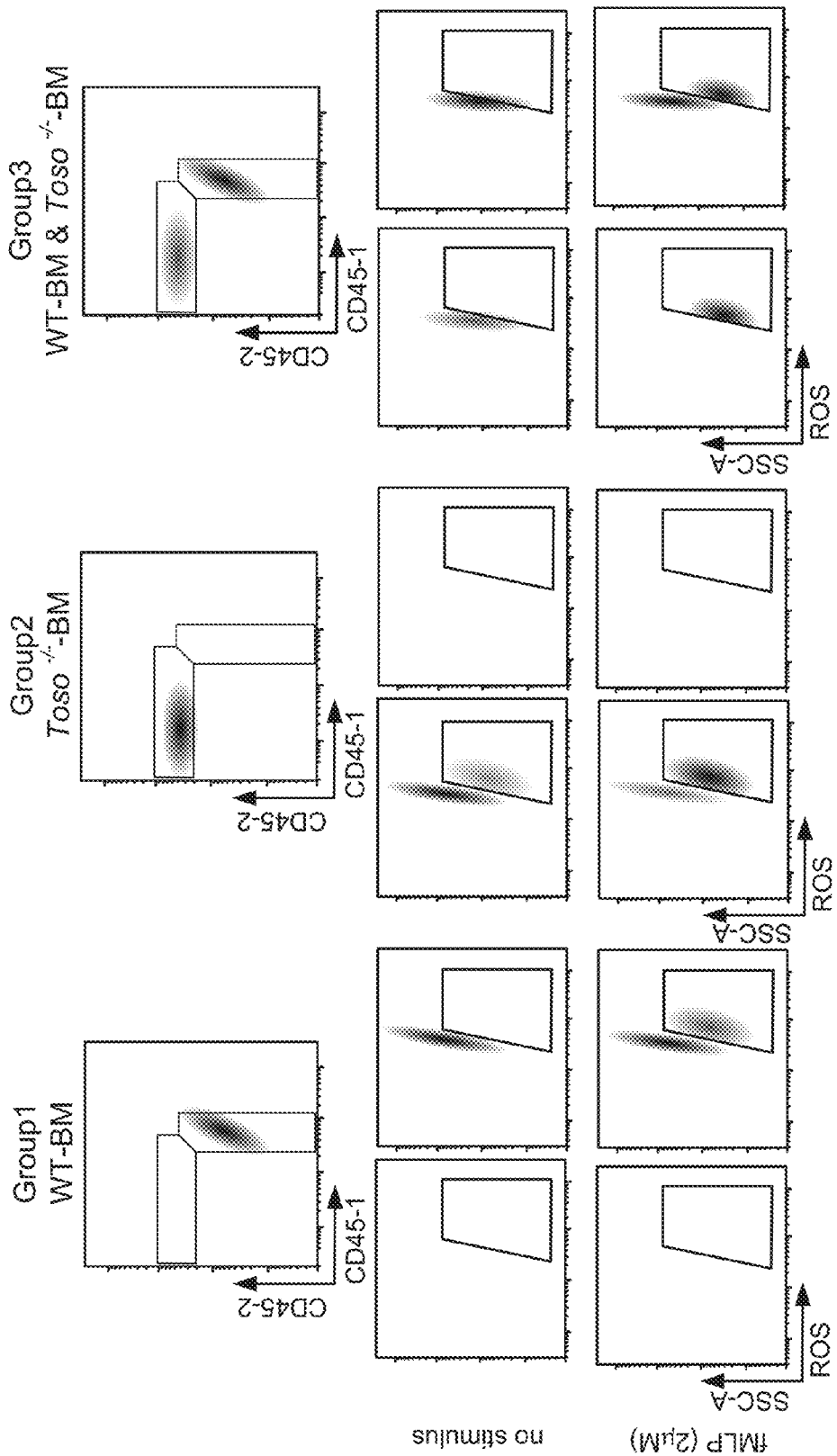
FIG. 14A, FIG. 14B, FIG. 14C and FIG. 14D show that activation threshold in granulocytes is regulated intrinsically. C57BL/6 wildtype mice were irradiated and reconstituted with bone marrow form wildtype mice carrying a point mutation in the CD45 gene (CD45.1, group 1), Toso$^{-/-}$ mice (CD45.2, group 2) or a 1:1 mixture of wildtype (CD45.1) bone marrow and Toso$^{-/-}$ bone marrow cells (CD45.2, group 3) as describe in methods. 30 days after bone marrow transplantation, peripheral blood was stimulated with fMLP and analyzed for activated granulocytes
Figure 14B:
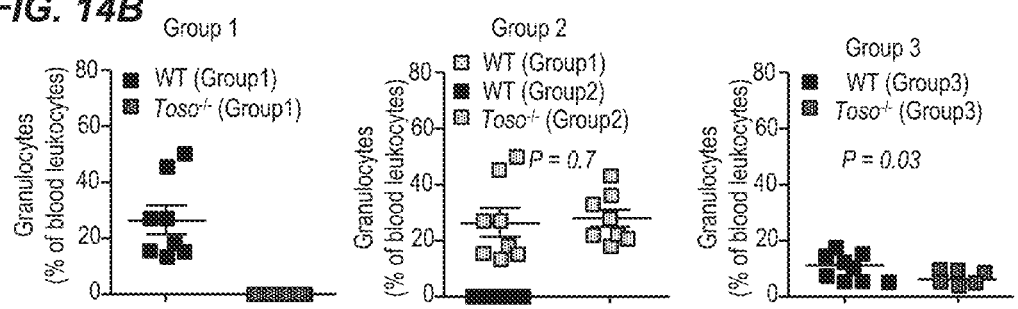

Granulocytes derived from Toso$^{-/-}$ mice had a lowered threshold for differentiation into an effector phenotype when compared to wildtype granulocytes. Besides their intrinsic regulation, granulocyte activation is influenced by several extrinsic humoral factors (like: cytokines, antibodies, complement factors) as well as the activation state of surrounding cells such as B cells, T cells, endothelial cells or platelets. To gain more insights into the mechanisms of lowered activation threshold of granulocytes derived from Toso$^{-/-}$ mice, the mixed bone marrow chimeras were analyzed. C57BL/6 mice were irradiated and then reconstituted with either WT, Toso$^{-/-}$ or mixed WT/Toso$^{-/-}$ (ratio 1:1) bone marrow. WT bone marrow could be tracked separately in chimeric mice by expression of the CD45.1 isoform (FIG. 14a). This mixed bone marrow chimeras allowed analysis of the activation threshold of WT and Toso$^{-/-}$ granulocyte derived from the same mouse. Observed differences in the activation threshold (especially those in the mixed chimeric mice) would suggest that Toso regulates activation of granulocytes intrinsically. Analysis of bone marrow chimeras 30 days after bone marrow transplantation showed that Toso$^{-/-}$ granulocytes reconstituted in the same number as WT granulocytes suggesting again that there was no major role of Toso in the development of granulocytes (FIG. 14b). In the mixed chimeras total granulocytes (WT and Toso$^{-/-}$) were comparable to the mice receiving bone marrow from a single mouse strain (FIG. 14b). There was not a striking advantage of WT versus Toso$^{-/-}$ granulocytes in the competitive setting of the mixed bone marrow chimera (FIG. 14b).

Figure 14C:
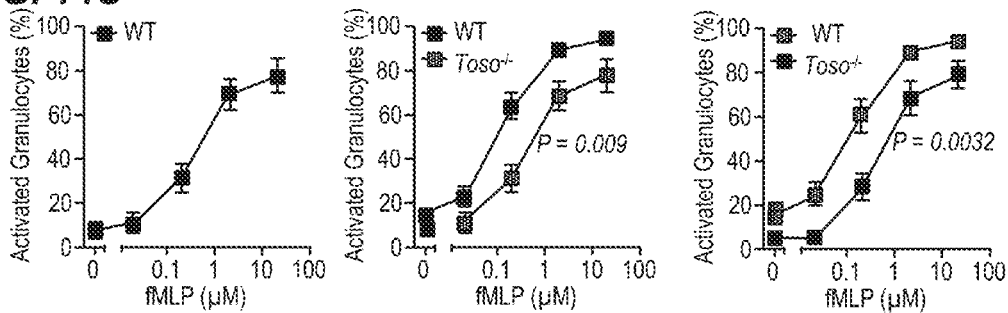

Next the activation threshold of WT versus Toso$^{-/-}$ granulocytes in the chimeric mice were analyzed. Treatment with fMLP activated more granulocytes in mice which received bone marrow transplantation (FIG. 14a versus FIG. 13a), which may, without being limited to this potential mechanism, be due to different cytokine levels in mice receiving bone marrow transplantation. Comparable to the data derived from the Toso$^{-/-}$ mice, the C57BL/6 mice, reconstituted with Toso$^{-/-}$ bone marrow, showed a lowered activation threshold (FIG. 14c). This was also seen in the mixed bone marrow chimeras (FIG. 14c). This suggests that Toso influenced the activation threshold of granulocytes intrinsically.

Figure 14D:
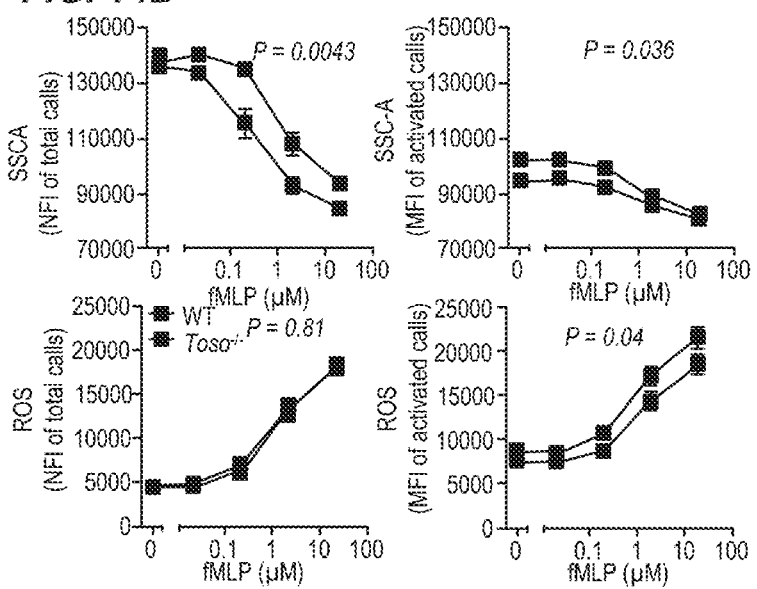

In order to determine if Toso in addition influenced the strength of effector function, the amount of ROS production of activated WT and activated Toso$^{-/-}$ granulocytes was determined. Activated WT granulocytes showed significantly more ROS production than activated Toso$^{-/-}$ granulocytes (FIG. 14d). These data show that Toso enhanced the activation threshold of granulocytes. Once granulocytes were activated, they showed enhanced effector function in the presence of Toso.

Impaired Control of Listeria in Toso Deficient Mice

Figure 15A:
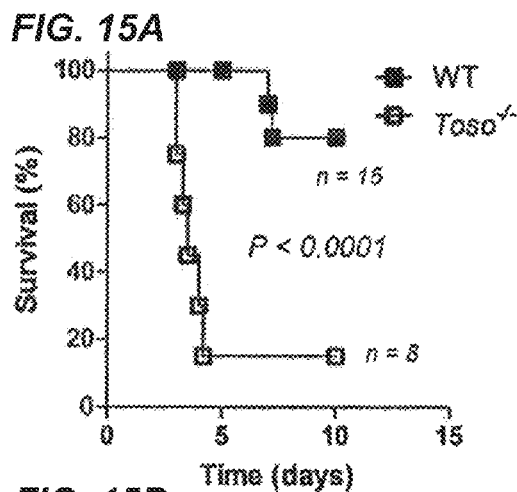
FIG. 15A, FIG. 15B, FIG. 15C, FIG. 15D, FIG. 15E and FIG. 15F show impaired control of *Listeria* in Toso deficient mice.
Figure 15E:
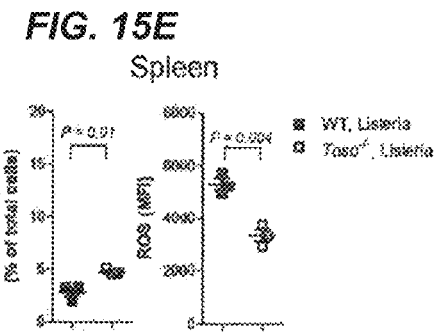
Figure 15B:
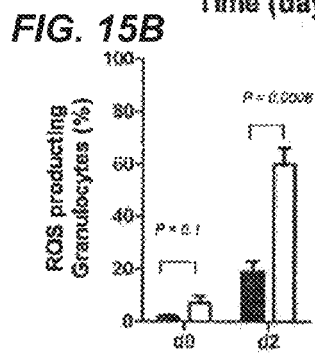

The effect of the lack of Toso in granulocytes on bacterial control in vivo was assessed. Infection with gram-positive Listeria monocytogenes is in particular strongly dependent on the fast activation of granulocytes. Infection with a sublethal dose of Listeria led to increased death in Toso$^{-/-}$ mice (FIG. 15a), suggesting that Toso was essential for the control of bacteria. Blood granulocytes in Toso$^{-/-}$ mice showed enhanced degranulation and ROS production two days after Listeria inoculation (FIG. 15b). This correlated with enhanced release of Myeloperoxidase in serum of Toso$^{-/-}$ mice (FIG. 15c).

One possibility was that Toso$^{-/-}$ granulocytes were rapidly activated in the blood, but may have failed to exert their full blown effector function in the infected organ. To analyze this hypothesis, the infected wildtype or Toso$^{-/-}$ mice were infected with 2×10$^6$ CFU of Listeria and histology was analyzed after 20 hours. Granulomas were found in both NT and Toso$^{-/-}$ mice the (FIG. 15d), suggesting that Toso was not involved in granuloma formation. Staining for Listeria showed enhanced bacteria in the granuloma (FIG. 15d), suggesting that the effector function in the granuloma was effected by Toso.

Figure 15F:
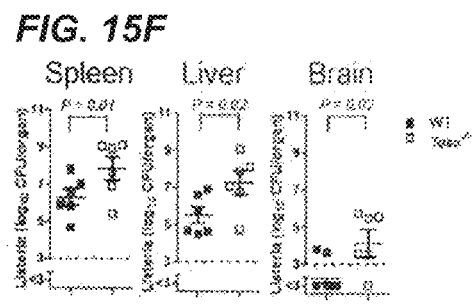
Figure 15C:
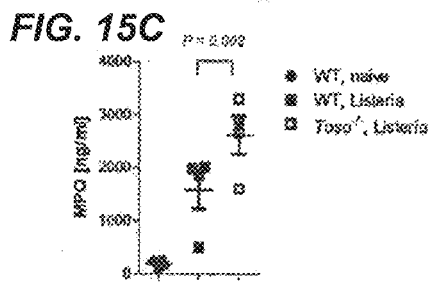
Figure 15D:
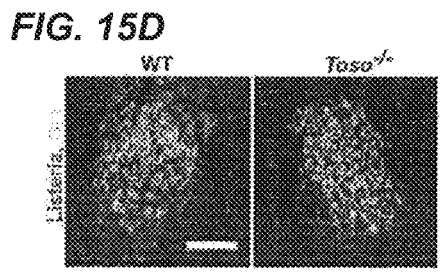
Figure 18:
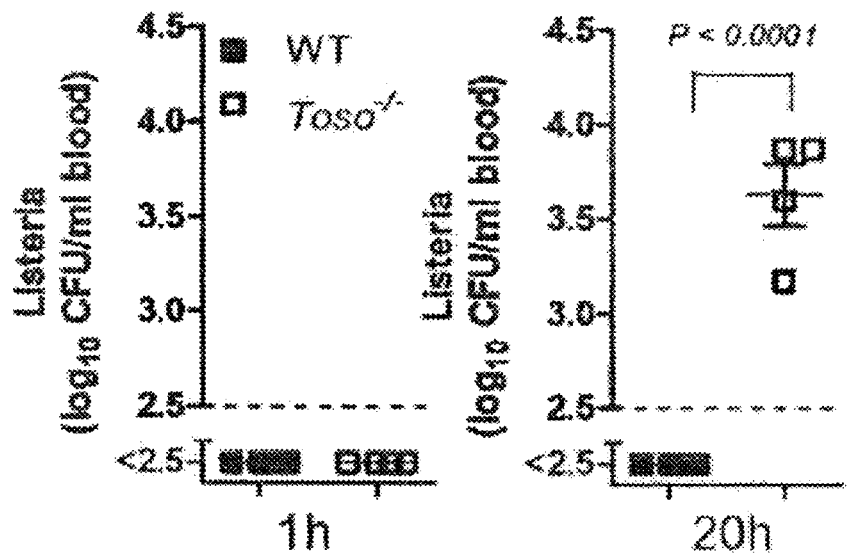
FIG. 18 shows Listerium bacteraemia after infection of Toso$^{-/-}$ mice, Toso$^{-/-}$—and corresponding wildtype mice were infected with 1×10$^6$ CFU of *Listeria monocytogenes*. Blood *Listeria* titer was assessed one and 20 hours after infection (n=4).

Analysis of granulocytes one day after infection in the organ, showed reduced effector function (FIG. 15e) and Listeria growth was significantly enhanced in liver and spleen of Toso$^{-/-}$ mice (FIG. 15f). This was associated with spread of Listeria into the blood (FIG. 18) and finally also to the brain, which was probably the reason for death of Listeria infected Toso$^{-/-}$ mice (FIG. 15f). These data show that Toso$^{-/-}$ mice showed enhanced susceptibility to Listeria infection. This correlated with enhanced granulocytes activation in the blood, reduced effector function in the liver and spleen and spread of Listeria to the brain.

Toso Regulates Surface CD11b and CD18 Expression on Granulocytes

Figure 16A:
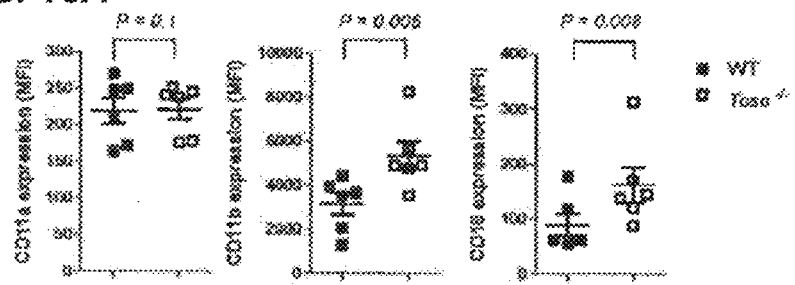
FIG. 16A, FIG. 16B, FIG. 16C and FIG. 16D show that expression of CD11 b and CD18 is influenced by Toso.
Figure 16B:
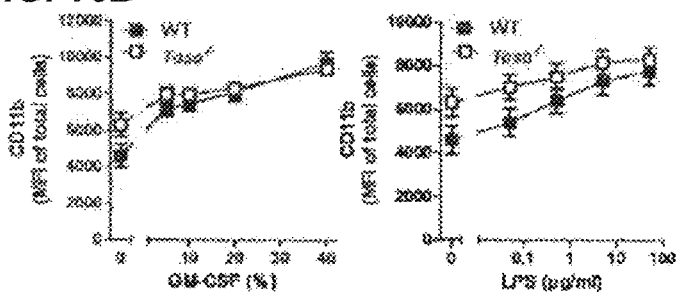
Figure 16C:
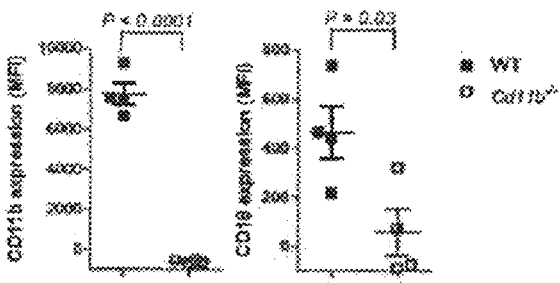
Figure 16D:
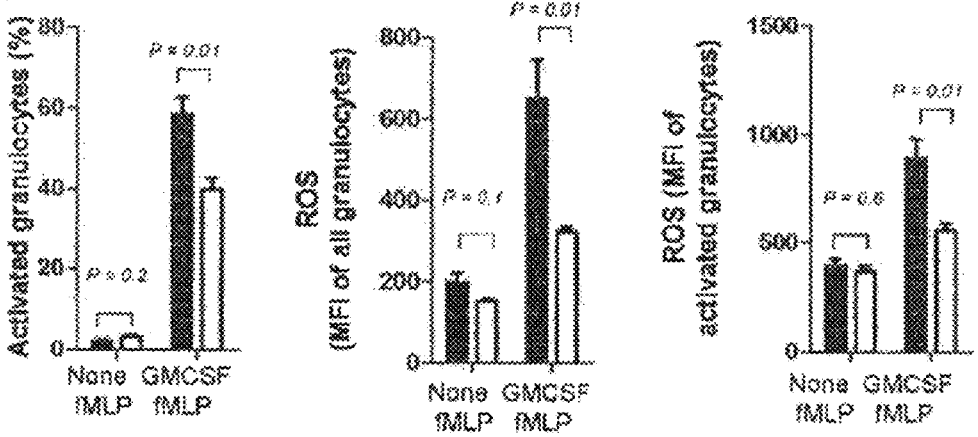

Toso deficient granulocytes display enhanced activation in the blood but reduced effector function of granulocytes in the tissue. This phenotype would fit well to a different expression and/or different signaling of integrins. CD11a, CD11 b and CD18 are important integrins for granulocyte activation. Therefore the expression of CD11a, CD11 b and CD18 was compared in WT and Toso$^{-/-}$ granulocytes. There was a significantly enhanced expression of CD11 b and CD18 on naïve Toso deficient granulocytes (FIG. 16a). Expression of CD11a was not significantly different between WT and Toso$^{-/-}$ granulocytes (FIG. 16a). Upon activation with GM-CSF or LPS, CD11b expression was up-regulated in both WT and Toso$^{-/-}$ granulocytes, however the difference of expression was decreasing with increasing LPS and GM-CSF concentrations (FIG. 16b). LPS and GM-CSF reduced the activation threshold of granulocytes upon fMLP. Therefore the difference in the CD11 b expression between WT and Toso$^{-/-}$ granulocytes could likely explain the different activation threshold. To see if indeed CD11b expression is involved in regulation of the activation threshold, the inventors analyzed the role of CD11 b in the system. As expected, lack of CD11 b led to reduced expression of CD18 (FIG. 16c). Cd11b$^{-/-}$ granulocytes showed reduced activation and ROS production upon treatment with fMLP together with GM-CSF (FIG. 16d). These data show that Toso$^{-/-}$ granulocytes showed enhanced basal expression of CD11 b, an integrin which influences the activation threshold of granulocytes. Those findings linked the enhanced CD11b expression in Toso$^{-/-}$ granulocytes with the reduced activation threshold in the absence of Toso.

Example 10

Toso Plays a Role in Glucose Tolerance and Insulin Sensitivity

Figure 19A:
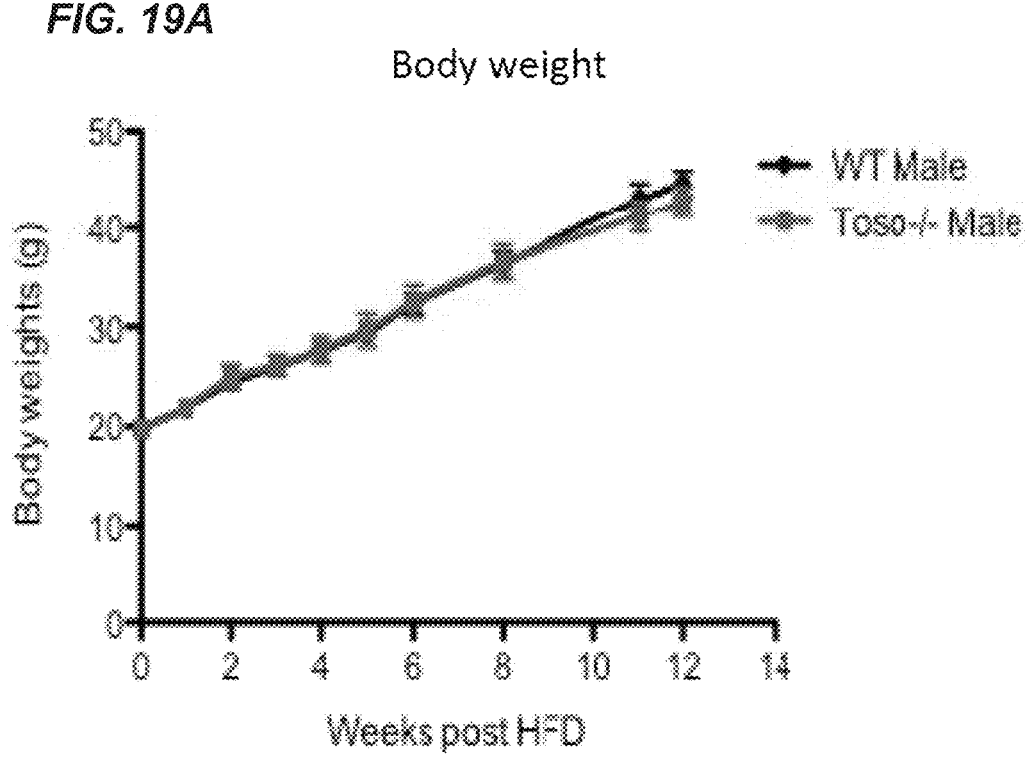
FIG. 19A and FIG. 19B show data from wildtype and Toso$^{-/-}$ mice after initiation of a high fat diet.
Figure 19B:
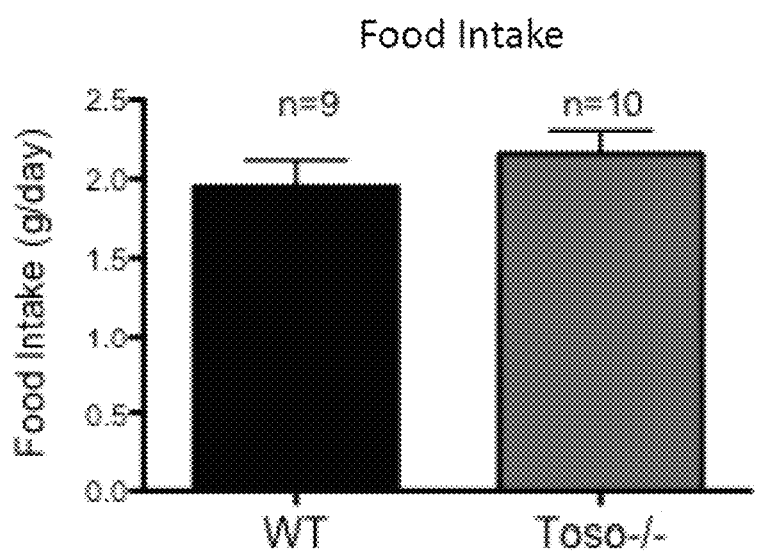

This example demonstrates that Toso plays a role in glucose tolerance and insulin sensitivity. FIG. 19 shows that Toso$^{-/-}$ mice have normal food intake and body weight after initiation of a high fat diet. For the experiments in FIG. 19A, body weights of WT and Toso$^{-/-}$ male mice were monitored since the initiation of high fat diet (starting at 5 weeks of age). For FIG. 19B, food intake was measured at 14 weeks post high fat diet. Food intake was measured by housing animals singly, with determinations of the differences in food weight at the beginning and end of a 2-day period.

Figure 20A:
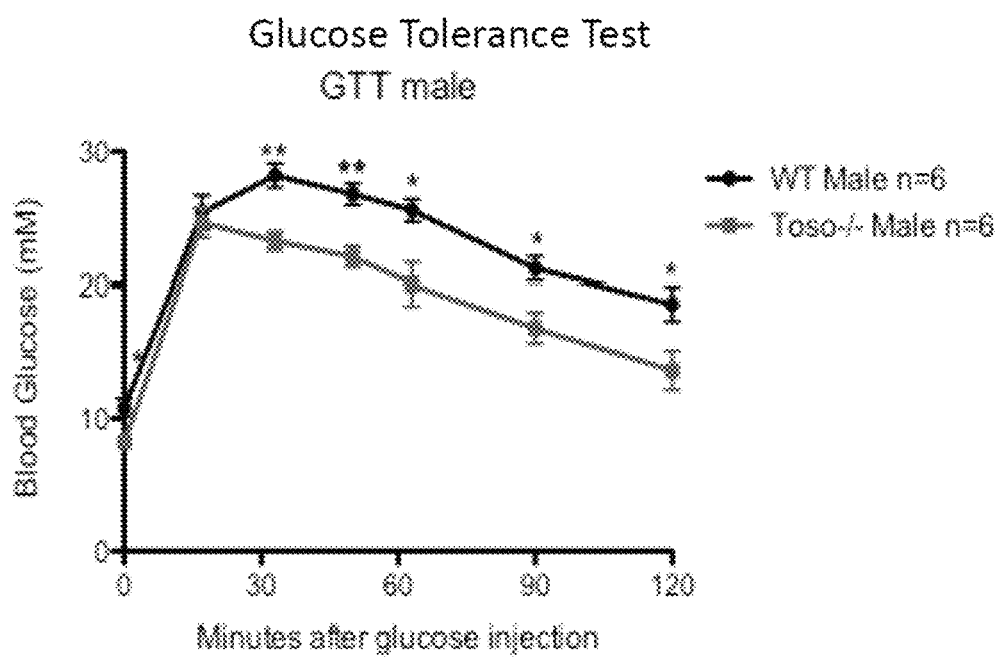
FIG. 20A shows data from a glucose tolerance test from wildtype and Toso$^{-/-}$ mice after initiation of a high fat diet.
Figure 20B:
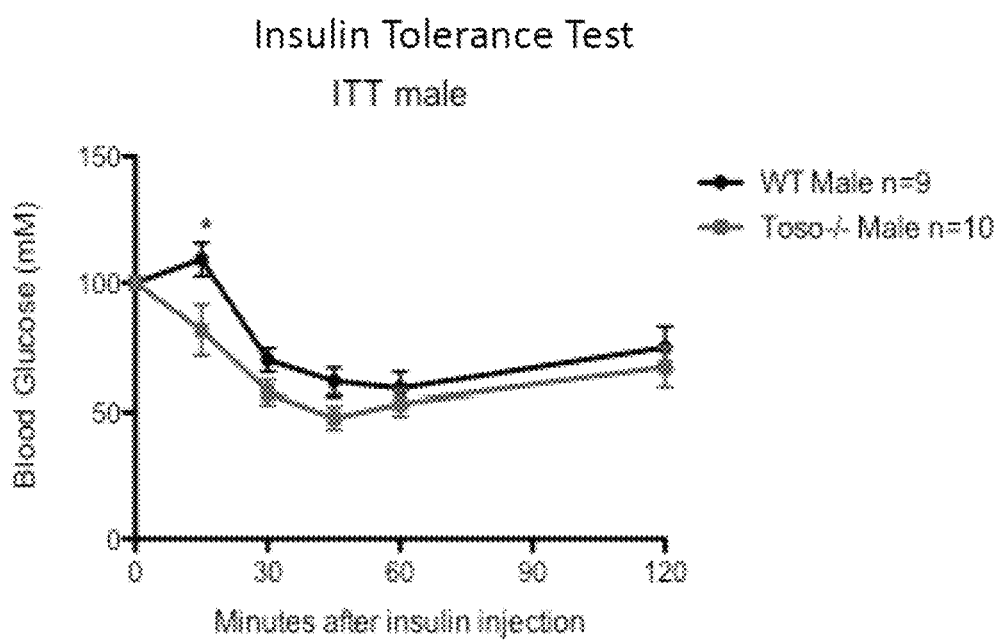
FIG. 20B shows data from an insulin tolerance test from the same set of mice.

As shown in FIG. 20, Toso$^{-/-}$ mice had enhanced glucose tolerance and insulin sensitivity compared to wildtype mice after being on a high fat diet for 10-13 weeks. Glucose Tolerance test was performed with wildtype and Toso$^{-/-}$ mice that were fed with high fat diet for 10-13 weeks since 5 weeks of age (note that similar results were obtained with female mice groups). The Insulin Tolerance test was performed with wildtype and Toso$^{-/-}$ mice that were fed with high fat diet for 10-13 weeks since 5 weeks of age.

Glucose tolerance tests were performed on overnight-fasted animals between 9:30 and 11:30 a.m., utilizing a glucose dose of 1 g/kg of body weight injected intraperitoneally (i.p.) and measurements of glucose levels at 0, 15, 30, 60, and 120 min after the injection.

Insulin tolerance tests were performed on overnight-fasted animals between 9:30 and 11:30 a.m. or 4.5-hour fasted animals between 1:00-3 p.m., utilizing human regular insulin (Humalog) at a dose of 0.5 U/kg body weight, and blood glucose levels were measured at 0, 15, 30, 45, and 60 min after the injection.

Figure 21A:
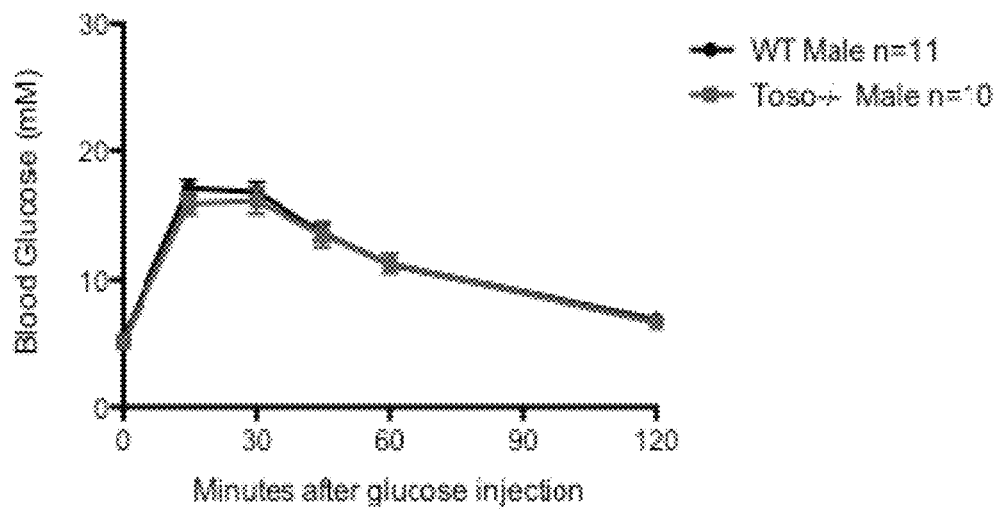
FIG. 21A and FIG. 21B show data illustrating that wildtype and Toso$^{-/-}$ mice maintained on a regular chow (non-high fat) diet display similar levels of glucose tolerance (FIG. 21A) and insulin tolerance (FIG. 21B).
Figure 21B:
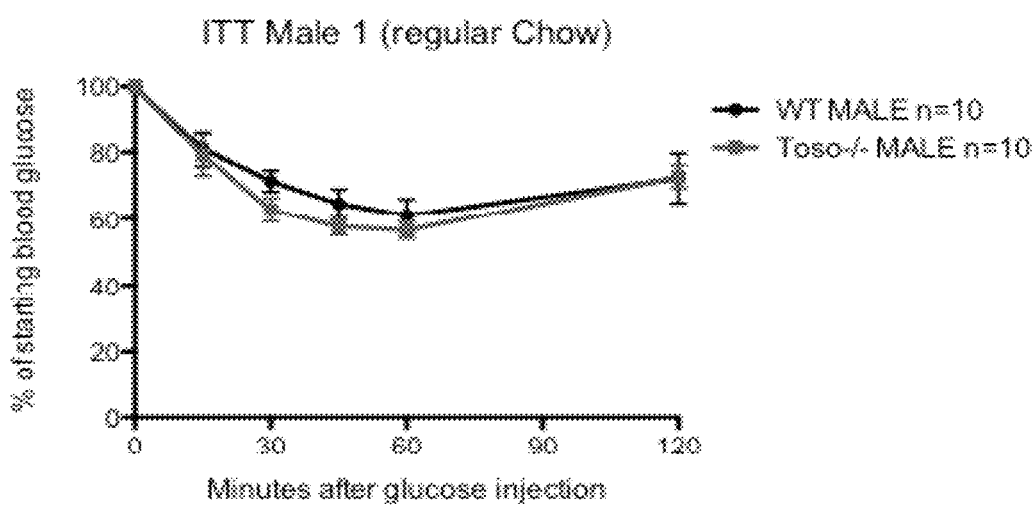

In contrast to the mice fed a high fat diet, FIG. 21A and FIG. 21B show that Toso$^{-/-}$ had similar glucose tolerance and insulin sensitivity to wildtype mice fed when both sets of mice were regular chow for 10-13 weeks. Glucose Tolerance test was performed with wildtype and Toso$^{-/-}$ male mice that were fed with regular chow (15-18 weeks old). Insulin Tolerance test was performed with wildtype and Toso$^{-/-}$ male mice that were fed with regular chow (15-18 weeks old). FIG. 21A and FIG. 21B suggest, without being limited by theory, that the protective effect of Toso-deficiency requires a high fat diet. Glucose tolerance tests were performed on overnight-fasted animals between 9:30 and 11:30 a.m., utilizing a glucose dose of 1 g/kg of body weight injected intraperitoneally (i.p.) and measurements of glucose levels at 0, 15, 30, 60, and 120 min after the injection. Insulin tolerance tests were performed on overnight-fasted animals between 9:30 and 11:30 a.m. or 4.5-hour fasted animals between 1:00-3 p.m., utilizing human regular insulin (Humalog) at a dose of 0.5 U/kg body weight, and blood glucose levels were measured at 0, 15, 30, 45, and 60 min after the injection.

Example 11

Figure 22A:
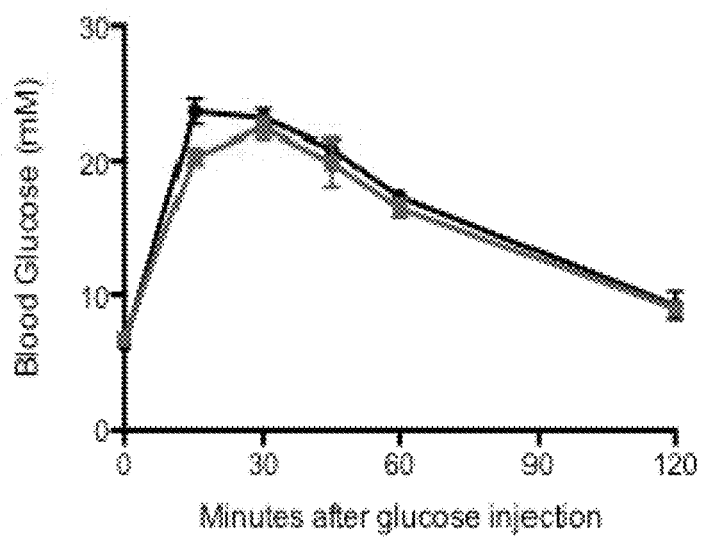
FIG. 22A and FIG. 22B show data on glucose tolerance before treatment of wildtype mice with soluble Toso protein (FIG. 22A) and after treatment (FIG. 22B).
Figure 22B:
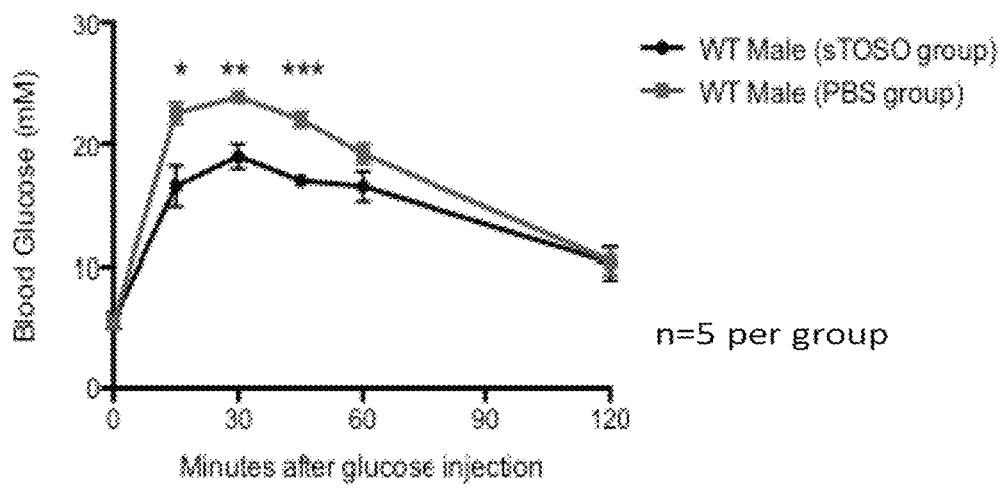

Treatment with Soluble Toso Improves Glucose Tolerance in Wildtype Mice Fed with a High Fat Diet This example demonstrates that treatment with a soluble Toso protein (SEQ ID NO: 5) improved glucose tolerance in wildtype mice fed with a high fat diet for 14 weeks. FIG. 22A shows data from wildtype male mice before soluble Toso treatment. The glucose tolerance test was done with fasted wildtype mice fed with high fat diet (60% fat calories) for 14 weeks since 5 weeks of age. FIG. 22B shows data from wildtype mice after soluble Toso treatment. The mice (high fat diet for 14 weeks) were treated with soluble Toso-hIgG at a dose of 50 μg intraperitoneally on day 0, 2, 5, 7, 9, and 12. Glucose tolerance test was performed on day 14 after overnight fasting. During the course of the soluble Toso protein treatment, the mice were continued with the high fat diet. Glucose tolerance tests were performed on overnight-fasted animals between 9:30 and 11:30 a.m., utilizing a glucose dose of 1 g/kg of body weight injected intraperitoneally (i.p.) and measurements of glucose levels at 0, 15, 30, 60, and 120 min after the injection.

Example 12

Generation of Stable Cell Lines Secreting Human and Mouse Toso-Fc

Toso-Fc encoding cDNAs were transfected into adherent HEK293T cells using Lipofectamine 2000. Single clones were selected in DMEM media supplemented with 10% Fetal Bovine serum and 0.2 mg/ml Zeocin. High expressing clones were expanded to 15 cm dishes, and split 1:2 at confluence. At each split, stable transfectants were cultured in media with successively more serum free Freestyle media, and successively less DMEM/FBS media to condition the cells for serum free growth. (e.g. ~90% DMEM/FBS 10% Freestyle at split 1→100% Freestyle at split 10). Stable transfectants conditioned to grow in serum free media grew in suspension in an orbital shaker incubator (37° C., 8% CO2, 125 rpm) without a loss in viability.

The present specification provides a complete description of the methodologies, systems and/or structures and uses thereof in example aspects of the presently-described technology. Although various aspects of this technology have been described above with a certain degree of particularity, or with reference to one or more individual aspects, those skilled in the art could make numerous alterations to the disclosed aspects without departing from the spirit or scope of the technology hereof. Since many aspects can be made without departing from the spirit and scope of the presently described technology, the appropriate scope resides in the claims hereinafter appended. Other aspects are therefore contemplated. Furthermore, it should be understood that any operations may be performed in any order, unless explicitly claimed otherwise or a specific order is inherently necessitated by the claim language. It is intended that all matter contained in the above description and shown in the accompanying drawings shall be interpreted as illustrative only of particular aspects and are not limiting to the embodiments shown. Unless otherwise clear from the context or expressly stated, any concentration values provided herein are generally given in terms of admixture values or percentages without regard to any conversion that occurs upon or following addition of the particular component of the mixture. To the extent not already expressly incorporated herein, all published references and patent documents referred to in this disclosure are incorporated herein by reference in their entirety for all purposes. Changes in detail or structure may be made without departing from the basic elements of the present technology as defined in the following claims.

What is claimed:

1. A method for treating melanoma in a subject, said method comprising administering to said subject a composition comprising a therapeutically effective amount of a Toso composition, wherein said Toso composition comprises an extracellular Toso domain, an Fc domain and a linker between said extracellular Toso domain and said Fc domain, and said Toso composition does not comprise a full-length Toso protein, and wherein said Toso composition modulates Toso activity.

2. The method of claim 1, wherein said extracellular Toso domain comprises amino acids 1 to 104 of SEQ ID NO: 8.

3. The method of claim 1, wherein said linker is an amino acid linker comprising the sequence according to SEQ ID NO: 25.

4. The method of claim 1, wherein said Toso composition comprises the amino acid sequence according to SEQ ID NO: 5.

5. The method of claim 1, wherein said Toso composition further comprises a signal sequence and wherein the signal sequence is an IL-2 signal sequence.

* * * * *